United States Patent [19]

Okazaki et al.

[11] Patent Number: 5,475,114
[45] Date of Patent: Dec. 12, 1995

[54] PYRAZOLOTRIAZOLE DERIVATIVES

[75] Inventors: Toshio Okazaki; Akira Suga; Toshihiro Watanabe; Kazumi Kikuchi; Osamu Inagaki, all of Ibaraki; Isao Yanagisawa, Tokyo, all of Japan

[73] Assignee: Yamanouchi Pharmaceutical Co., Ltd., Tokyo, Japan

[21] Appl. No.: 199,281

[22] PCT Filed: Aug. 27, 1992

[86] PCT No.: PCT/JP92/01090

§ 371 Date: Mar. 1, 1994

§ 102(e) Date: Mar. 1, 1994

[87] PCT Pub. No.: WO93/05044

PCT Pub. Date: Mar. 18, 1993

[30] Foreign Application Priority Data

Sep. 3, 1991 [JP] Japan .................................. 3-250430
Dec. 2, 1991 [JP] Japan .................................. 3-344012
Apr. 22, 1992 [JP] Japan .................................. 4-129716

[51] Int. Cl.$^6$ .................... C07D 471/08; A61K 31/41
[52] U.S. Cl. ......................................................... 548/253
[58] Field of Search .......................... 548/253; 514/381, 514/382

*Primary Examiner*—David B. Springer
*Attorney, Agent, or Firm*—Burgess, Ryan & Wayne

[57] ABSTRACT

This invention relates to a pyrazolotriazole derivative represented by the general formula:

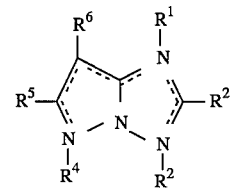

wherein each symbol means as follows;

$R^1$, $R^3$ and $R^4$: one of them represents hydrogen, tetrazolylated biphenylmethyl or lower alkyl, $R^2$: hydrogen, tetrazolylated biphenylmethyl, cycloalkyl or lower alkyl, and $R^5$ and $R^6$: these may be the same or different from each other, and each represents hydrogen, halogen, tetrazolylated biphenylmethyl, formyl, carboxyl, esterified carboxyl, cycloalkyl, lower alkoxy, lower alkoxycarbonyl, or lower alkyl which may be substituted with hydroxyl, formyl or carboxyl, provided that at least one of $R^1$ to $R^6$ is tetrazolylated biphenylmethyl, and the broken lines mean that the pyrazolotriazole ring forms three double bonds, or a pharmaceutically acceptable salt thereof, and to a process for the production thereof, wherein the above compound (I) is useful for treating various diseases caused by the physiological function of angiotensin II.

13 Claims, No Drawings

PYRAZOLOTRIAZOLE DERIVATIVES

TECHNICAL FIELD

This invention relates to novel pyrazolotriazole derivatives or salts thereof which show an angiotensin II (to be referred to as AII hereinafter) antagonism.

BACKGROUND ART

AII, a physiologically active peptide which shows a strong pressor reaction, has been regarded as a causal substance of hypertension in various mammalian species.

There are a few known pathways for the formation of AII in the living body, including a typical pathway in which angiotensin I is formed from angiotensinogen by the action of an enzyme, renin, and then converted into AII by the action of an angiotensin converting enzyme (ACE). Since the compound of the present invention inhibits expression of functions AII by acting on the AII receptor, it is useful as an AII antagonist.

Examples of known AII antagonists include imidazole derivatives disclosed in European Patent No. 253,310.

DISCLOSURE OF THE INVENTION

The inventors of the present invention have created various types of compounds and subjected them to screening and, as the result, found pyrazolotriazole derivatives which have excellent anti-AII activity and whose chemical structure is different from those of the prior art compounds.

The pyrazolotriazole derivative of the present invention is represented by the following general formula.

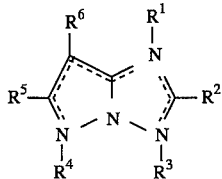
(I)

(Each symbol in the above formula means as follows; $R^1$, $R^3$ and $R^4$: one of them represents a hydrogen atom, a biphenylmethyl group having a tetrazolyl group which may be substituted by aralkyl, or a lower alkyl group, and each of the remaining two has no substituent, $R^2$: a hydrogen atom, a biphenylmethyl group having a tetrazolyl group which may be substituted by aralkyl, a cycloalkyl group, or a lower alkyl group which may be substituted by hydroxyl, lower alkoxy, carboxyl or lower alkoxycarbonyl, and $R^5$ and $R^6$: these may be the same or different from each other, and each represents a hydrogen atom, a halogen atom, a biphenylmethyl group having a tetrazolyl group which may be substituted by aralkyl, a formyl group, a carboxyl group, an esterified carboxyl group, a cycloalkyl group, a lower alkoxy group, or a lower alkyl group which may be substituted by hydroxyl, formyl, carboxyl, lower alkoxy or lower alkoxycarbonyl, provided that at least one of $R^1$ to $R^6$ is a biphenylmethyl group having a tetrazolyl group which may be substituted by aralkyl and the broken lines mean that the pyrazolotriazole ring forms three double bonds.)

The following describes the compound of the present invention in detail.

Unless otherwise indicated, the term "lower" as defined in the general formula means a straight or branched carbon chain having 1 to 6 carbon atoms.

In consequence, illustrative examples of the "lower alkyl group" include methyl, ethyl, propyl, isopropyl, butyl, isobutyl, sec-butyl, tert-butyl, pentyl (amyl), iso-pentyl, neopentyl, tert-pentyl, 1-methylbutyl, 2-methylbutyl, 1,2-dimethylpropyl, hexyl, iso-hexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and the like groups.

The lower alkyl group may be substituted with other substituent group. In the case of $R^2$, such a substituent group is hydroxyl, a lower alkoxy, carboxyl or a lower alkoxycarbonyl.

In the case of $R^5$ and $R^6$, the substituent group is hydroxyl, formyl, carboxyl, a lower alkoxy or a lower alkoxycarbonyl.

An optional position of a lower alkyl group can be substituted with one or two of these substituent groups. Typical examples of substituent-containing lower alkyl groups include methoxymethyl, ethoxymethyl, 1-methoxyethyl, 2-methoxyethyl, 1-ethoxyethyl, 2-ethoxyethyl, methoxycarbonylmethyl, 1-methoxycarbonylethyl, ethoxycarbonylmethyl, 1-ethoxycarbonylethyl, carboxymethyl, 1-carboxyethyl, 2-carboxyethyl, 1-carboxypropyl, 2-carboxypropyl, 3-carboxypropyl, dimethoxymethyl, diethoxymethyl, 2,2-dimethoxyethyl, 2,2-diethoxyethyl, 3,3-dimethoxypropyl, 3,3-diethoxypropyl, 3,3-dipropoxypropyl, 4,4-dimethoxybutyl, 4,4-diethoxybutyl, 4,4-dipropoxybutyl, 5,5-dimethoxypentyl, 5,5-diethoxypentyl, hydroxymethyl, 1-hydroxyethyl, 2-hydroxyethyl, 1-hydroxypropyl, 2-hydroxypropyl, 3-hydroxypropyl, formylmethyl, 1-formylethyl, 2-formylethyl, 1-formylpropyl, 2-formylpropyl, 3-formylpropyl and the like groups.

Examples of the "lower alkoxy group" include methoxy, ethoxy, propoxy, isopropoxy, butoxy, isobutoxy, sec-butoxy, tert-butoxy, pentyloxy (amyloxy), isopentyloxy, tert-pentyloxy, neopentyloxy, 2-methylbutoxy, 1,2-dimethylpropoxy, 1-ethylpropoxy, hexyloxy and the like groups.

The "lower alkoxycarbonyl group" is a group in which a carbonyl group is linked to one of the aforementioned lower alkoxy groups, with its preferred illustrative examples including methoxycarbonyl, ethoxycarbonyl, isopropoxycarbonyl and butoxycarbonyl.

Illustrative examples of the "cycloalkyl group" are those having 3 to 12 carbon atoms, such as cyclopropyl, cyclobutyl, cyclopentyl, cyclohexyl, cycloheptyl, cyclooctyl, cyclononyl, cyclodecyl, cycloundecyl and the like groups.

Examples of the "aralkyl group" include triphenylmethyl, benzyl, phenetyl, 1-phenylethyl and the like groups.

Illustrative examples of the "halogen atom" include iodine, bromine, chlorine, fluorine and the like atoms.

The esterified carboxyl group means a carboxylic acid residue esterified with the aforementioned lower alkyl group, a group represented by a formula

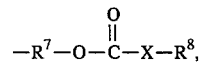

a group represented by a formula

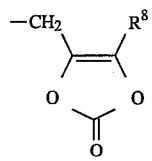

or a group represented by a formula

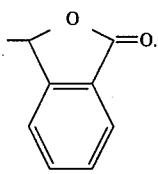

In this instance, $R^7$ in the above formula means a "lower alkylene or lower alkylidene group" of straight or branched carbon chain, and its illustrative examples include methylene, ethylene, propylene, dimethylmethylene, tetramethylene, pentamethylene, hexamethylene, ethylidene, propylidene and the like groups.

Also, $R^8$ means a "cycloalkyl group" or an "alkyl group". Examples of the cycloalkyl group include those described in the foregoing.

Examples of the alkyl group include long and medium chain hydrocarbon radicals having 7 to 12 carbon atoms, as well as the lower alkyl groups described in the foregoing. Preferred examples of the long and medium chain alkyl groups include heptyl, 1,1-diethylpropyl, 1,1-dipropylbutyl and the like groups.

Consequently, when X in the formula $—R^7—OCO—X—R^8$ is a single bond, examples of this type of group include acetoxymethyl, 1-acetoxyethyl, 2-acetoxyethyl, pivaloyloxymethyl, 2,2-dimethylpropanoyloxymethyl, 1-(pivaloyloxy)ethyl, 1-(pivaloyloxy)propyl, 2-(pivaloyloxy)ethyl, 2-(pivaloyloxy)propyl, (pivaloyloxy)propan-2-yl, 2,2-diethylbutanoyloxymethyl, 2,2-dipropylpentanoyloxymethyl, cyclopropylcarbonyloxymethyl, cyclobutylcarbonyloxymethyl, cyclopentylcarbonyloxymethyl, cyclohexylcarbonyloxymethyl and the like groups.

Also, when X in the formula is an oxygen atom, examples of such a type of group include methoxycarbonyloxymethyl, 1-(methoxycarbonyloxy)ethyl, 2-(methoxycarbonyloxy)ethyl, ethoxycarbonyloxymethyl, 1-(ethoxycarbonyloxy)ethyl, 2-(ethoxycarbonyloxy)ethyl, propoxycarbonyloxymethyl, 1-(propoxycarbonyloxy)ethyl, 2-(propoxycarbonyloxy)ethyl, cyclopropyloxycarbonyloxymethyl, 1-(cyclopropyloxycarbonyloxy)ethyl, 2-(cyclopropyloxycarbonyloxy)ethyl, cyclobutyloxycarbonyloxymethyl, 1-(cyclobutyloxycarbonyloxy)ethyl, 2-(cyclobutyloxycarbonyloxy)ethyl, cyclopentyloxycarbonyloxymethyl, 1-(cyclopentyloxycarbonyloxy)ethyl, 2-(cyclopentyloxycarbonyloxy)ethyl, cyclohexyloxycarbonyloxymethyl, 1-(cyclohexyloxycarbonyl)ethyl, 2-(cyclohexyloxycarbonyl)ethyl, cycloheptyloxycarbonyloxymethyl and the like groups.

Typical examples of the group represented by the formula

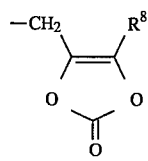

are as follows.

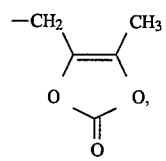

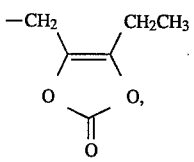

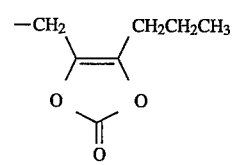

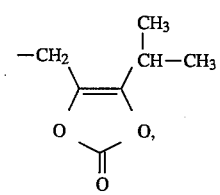

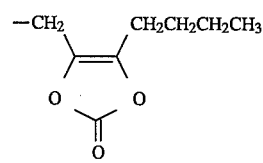

Compound (I) of the present invention forms salts with acids and bases. Examples of its salts with acids include acid addition salts with mineral acids such as hydrochloric acid, hydrobromic acid, hydroiodic acid, sulfuric acid, nitric acid, phosphoric acid and the like or with organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, glutamic acid and the like.

Examples of base salts include those with inorganic bases such as lithium, sodium, potassium, magnesium, calcium, aluminium and the like, organic bases such as methylamine, ethylamine, ethanolamine and the like and basic amino acids such as lysine, ornithine and the like, as well as ammonium salts. In addition, the compound of the present invention may contain asymmetric carbon atom(s) in some cases depending on the type of substituent groups. In consequence, the compound of the present invention includes its various isomers such as geometrical isomers, tautomers, optical isomers and the like, either in the isolated form or as mixtures thereof.

(Production Process)

The compound of the present invention can be produced by employing the following synthetic methods.

First method

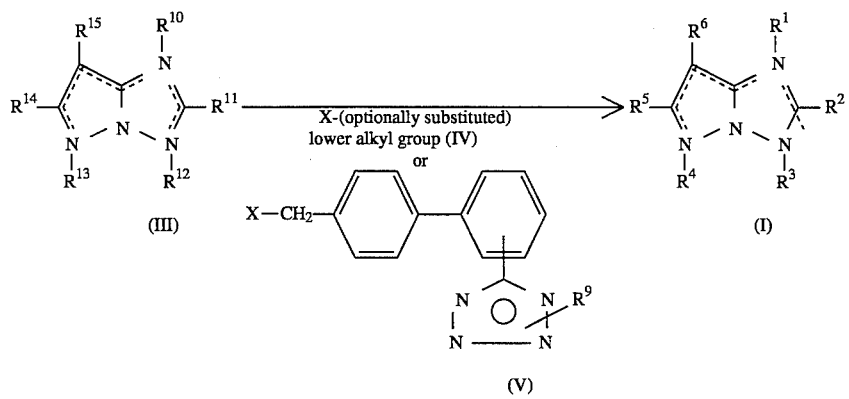

(In these formulae, $R^1$ to $R^6$ are as described in the foregoing,

- $R^{10}$, $R^{12}$ and $R^{13}$: one of them represents a hydrogen atom, and each of the remaining two has no substituent,
- $R^{11}$: a hydrogen atom, a biphenylmethyl group having a tetrazolyl group which may be substituted by aralkyl, a cycloalkyl group, or a lower alkyl group which may be substituted by hydroxyl, lower alkoxy, carboxyl or lower alkoxycarbonyl, and
- $R^{14}$ and $R^{15}$: these may be the same or different from each other, and each represents a hydrogen atom, a halogen atom, a biphenylmethyl group having a tetrazolyl group which may be substituted by aralkyl, a formyl group, a carboxyl group, an esterified carboxyl group, a cycloalkyl group, a lower alkoxy group, a lower alkoxycarbonyl group, or a lower alkyl group which may be substituted by hydroxyl, formyl, carboxyl, lower alkoxy or lower alkoxycarbonyl, provided that the broken lines mean that the pyrazolotriazole ring forms three double bonds, and X represents a halogen atom or a sulfonic acid residue and $R^9$ represents an aralkyl group.)

By allowing a pyrazoloimidazole compound represented by the general formula (III) to react with a lower alkyl halide (or sulfonate) represented by the general formula (IV) or with a biphenylmethyl halide (or sulfonate) represented by the general formula (V), the compound (I) of the present invention can be produced which has at least one more additional lower alkyl or biphenylmethyl group in comparison with the compound (III).

This reaction is effected by stirring the compound (III) with the compound (IV) and/or the compound (V) in corresponding amounts for reaction in an inert solvent at room temperature or with heating.

Preferably, a base may be added to the reaction system to accelerate the reaction.

Examples of the inert solvent include tetrahydrofuran, benzene, chloroform, toluene and the like. With regard to the base, potassium butoxide, potassium carbonate, sodium hydroxide, sodium hydride, metallic sodium, sodium methoxide, pyridine, triethylamine, picoline, lutidine, N,N-dimethylamine and the like may be used.

Second method (de-aralkylation)

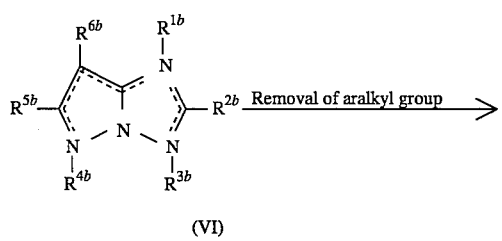

(Each symbol in the above formulae means as follows;

- $R^{1b}$, $R^{3b}$ and $R^{4b}$: one of them represents a hydrogen atom, a biphenylmethyl group having a tetrazolyl group substituted by aralkyl, or a lower alkyl group, and each of the remaining two has no substituent,
- $R^{2b}$: a hydrogen atom, a biphenylmethyl group having a tetrazolyl group substituted by aralkyl, a cycloalkyl group, or a lower alkyl group which may be substituted by hydroxyl, lower alkoxy, carboxyl or lower alkoxycarbonyl,
- $R^{5b}$ and $R^{6b}$: these may be the same or different from each other, and each represents a hydrogen atom, a halogen atom, a biphenylmethyl group having a tetrazolyl group substituted by aralkyl, a formyl group, a carboxyl group, an esterified carboxyl group, a cycloalkyl group, a lower alkoxy group, a lower alkoxycarbonyl group, or a lower alkyl group which may be substituted by hydroxyl, formyl, carboxyl, lower alkoxy or lower alkoxycarbonyl, provided that at least one of $R^{1b}$ to $R^{6b}$ is a biphenylmethyl group having a tetrazolyl group substituted by aralkyl and the broken lines mean that the pyrazolotriazole ring forms three double bonds, $R^{1c}$, $R^{3c}$ and $R^{4c}$: one of them represents a hydrogen atom, a biphenylmethyl group having a tetrazolyl group, or a lower alkyl group, and each of the remaining two has no substituent, $R^{2c}$: a hydrogen atom, a biphenylmethyl group having a tetrazolyl group, a cycloalkyl group, or a lower alkyl group which may be substituted by hydroxyl, lower alkoxy, carboxyl or lower alkoxycarbonyl, and $R^{5c}$ and $R^{6c}$: these may be the same or different from each other, and each represents a hydrogen atom, a halogen atom, a biphenylmethyl group having a tetrazolyl group, a formyl group, a carboxyl group, an esterified carboxyl group, a cycloalkyl group, a lower alkoxy group, a lower alkoxycarbonyl group, or a lower alkyl group which may be substituted by hydroxyl, formyl, carboxyl, lower alkoxy or lower alkoxycarbonyl, provided that at least one of $R^{1c}$ to $R^{6c}$ is a biphenylmethyl group having a tetrazolyl group and the broken lines mean that the pyrazolotriazole ring forms three double bonds.)

Among compounds of the present invention, the compound (VII) whose tetrazolyl group is not substituted by an aralkyl group can be obtained by a catalytic reduction, a liquid ammonia reduction or an acid treatment of the compound (VI) which has an aralkyl-substituted tetrazolyl group. As to the acid, acetic acid, trifluoroacetic acid, trichloroacetic acid, hydrochloric acid, sulfuric acid, hydrobromic acid-acetic acid and the like may be used. This reaction is carried out generally in an organic solvent such as methanol, ethanol, acetone or the like or in water, at room temperature or with heating (under reflux).

Third method

Among compounds of the present invention, a compound whose $R^2$ is a lower alkyl group which may be substituted by a carboxyl group can be obtained by hydrolyzing its corresponding ester compound. Also, a compound in which each of $R^5$ and $R^6$ is a carboxyl group, a lower alkoxycarbonyl group or a lower alkyl group which may be substituted with a carboxyl group can be obtained by oxidizing its corresponding aldehyde compound or hydrolyzing its corresponding ester compound.

(i) Oxidation

Oxidation of an aldehyde compound can be effected in the usual way, for example, by allowing silver oxide to react with sodium hydroxide, potassium hydroxide, barium hydroxide or sodium carbonate in an inert solvent cooled on an ice bath or at room temperature, adding the aldehyde compound to the resulting reaction solution and then effecting the oxidation reaction at room temperature or under reflux. Examples of the inert solvent include distilled water, methanol, acetone and the like.

Also, a corresponding carboxylic acid ester can be obtained by allowing an aldehyde compound of (I), whose $R^5$ and $R^6$ are the same or different from each other and each representing a formyl group, to react with manganese dioxide and sodium cyanide or potassium cyanide in an alcohol such as methanol, ethanol or the like at room temperature or with heating. In that case, it is desirable to add an acid to accelerate the reaction. Examples of useful acids include acetic acid, trifluoroacetic acid, hydrochloric acid, sulfuric acid, hydrobromic acid-acetic acid and the like.

(ii) Hydrolysis

Hydrolysis of an ester compound can be effected in the usual way, for example, by adding the ester compound to a basic inert solvent adjusted with sodium hydroxide, potassium hydroxide or the like and subsequently stirring or refluxing the mixture at room temperature or with heating.

Fourth method

When each of $R^5$ and $R^6$ of the compound of the present invention is a lower alkyl group which may be substituted with hydroxyl group, the compound can be obtained by reducing its corresponding aldehyde compound.

This reduction reaction can be effected in the usual way, for example, by dissolving an aldehyde compound in an inert solvent, adding a reducing agent of metal hydride such as lithium aluminum hydride, sodium borohydride, lithium borohydride, diisobutylaluminum hydride or the like to the resulting solution and then stirring the mixture on an ice bath or at room temperature.

The thus produced compound of the present invention is then isolated and purified in the free form or as a salt thereof.

Isolation and purification of the compound are carried out by employing usual chemical procedures such as extraction, concentration, distillation, crystallization, filtration, various chromatographic techniques and the like.

INDUSTRIAL APPLICABILITY

Since the compound of the present invention has an angiotensin II (AII) antagonism, it is useful for the treatment of various diseases caused by the physiological activity of AII (hypertension, chronic heart failure, cardiac hypertrophy, arteriosclerosis (blood vessel wall hypertrophy), diabetic nephropathy, diabetic retinopathy, chronic glomerulonephritis, proliferative glomerulonephritis, glaucoma, amnesia, anxiety, benign prostatic hypertrophy and difficulty of urination accompanied thereby, peripheral circulatory failure, complicated or secondary hyperaldosteronism, cerebrovascular disorder and the like). In addition, since the compound of the present invention also shows antagonism against AII which is formed without mediation by renin or ACE, more broader hypotensive spectrum than those of ACE inhibitors and renin antagonists is expected.

The AII receptor-blocking activity of the compound of the present invention was measured based on its antagonistic effect (in vitro) on AII contraction of an excised rabbit aorta and its inhibitory effect (in vivo) on AII-caused pressor reaction in a spinal cord-broken rat.

In vitro test:

A portion of rabbit aorta was excised to prepare a spiral strip specimen which was subsequently hung in Krebs-Hensseleit solution. This spiral strip specimen causes a dose-dependent contraction when AII is added to the Krebs-Hensseleit solution. Since a drug having AII receptor-blocking activity causes shifting of the dose-response curve of the AII-based contraction to the high concentration side or reduces maximum contraction by AII, a shifted width of the dose-response curve before and after the addition of each test drug or a maximum contraction inhibiting ratio was calculated.

The AII receptor-blocking activity was expressed by a $pA_2$ value (negative logarithmic value of the concentration of a blocking drug required to shift the dose-response curve to two times higher concentration side) or a $pD_2'$ value (negative logarithmic value of the concentration of a blocking drug required to inhibit 50% of the maximum contraction).

In vivo test:

An in vivo test was carried out by inserting cannulae into an aorta and a vein of a spinal cord-broken rat under artificial respiration. The spinal cord-broken rat shows 50 to 70 mm Hg of continuous increase in the blood pressure by continuous intravenous administration of AII (100 ng/kg/min). Since a drug having AII receptor-blocking activity inhibits the AII-caused continuous blood pressure increase in a dose-dependent manner, the AII antagonistic function of the test drug was examined based on the decreasing width of blood pressure after administration of the test drug. The AII receptor-blocking activity was expressed by an $IC_{30}$ value (a dose which decreases 30 mm Hg of blood pressure after the AII administration).

Results obtained by the above tests are shown in Tables 1 and 2.

TABLE 1

All receptor-blocking activity of the compounds of the present invention measured by the in vitro test

| Examples | in vitro | |
|---|---|---|
| | ($pA_2$ value) | ($pD_2'$ value) |
| Dup 753 (EP 253310, a compound disclosed in Example 89E) | 8.2 | |
| Example 52 (the compound of the present invention) | 8.65 | |
| Example 53 (the compound of the present invention) | 8.50 | |
| Example 57 (the compound of the present invention) | 8.52 | |
| Example 95 (the compound of the present invention) | 8.85 | |
| Example 96 (the compound of the present invention) | 9.16 | |
| Example 98 (the compound of the present invention) | 9.02 | |
| Example 99 (the compound of the present invention) | | 9.31 |
| Example 100 (the compound of the present invention) | 8.81 | |
| Example 101 (the compound of the present invention) | 9.25 | |
| Example 102 (the compound of the present invention) | 9.14 | |
| Example 105 (the compound of the present invention) | | 9.03 |

TABLE 2

All receptor-blocking activity of the compounds of the present invention measured by the in vivo test

| Examples | in vivo ($IC_{30}$ mmHg (mg/kg, iv)) |
|---|---|
| Dup 753 (EP 253310, a compound disclosed in Example 89E) | 0.1 |
| Example 52 (the compound of the present invention) | 0.025 |
| Example 53 (the compound of the present invention) | 0.01 |
| Example 57 (the compound of the present invention) | 0.04 |
| Example 95 (the compound of the present invention) | 0.06 |
| Example 96 (the compound of the present invention) | 0.02 |
| Example 98 (the compound of the present invention) | 0.02 |

Since the compound of the present invention has low toxicity, it is suitable for use as pharmaceutical drugs.

A pharmaceutical preparation containing, as an active ingredient, at least one of the compound (I) or salts thereof according to the present invention is prepared making use of carriers, vehicles and other additives usually used for the preparation of drugs.

Carriers and vehicles for use in the production of the pharmaceutical preparation may be solids or liquids, which include for example lactose, magnesium stearate, starch, talc, gelatin, agar, pectin, gum arabic, olive oil, sesame oil, cacao butter, ethylene glycol and the like, as well as other usually used substances.

The pharmaceutical preparation may be administered either by oral administration in the form of tablets, pills, capsules, granules, powders, solutions or the like or by parenteral administration in the form of injections such as intravenous injection and intramuscular injection or in the form of suppositories, percutaneous preparation, or the like. Though the dose should be optionally decided in each case taking into consideration symptoms, age, sex and the like of the patient to be treated, it may be in the range of from 10 to 1000 mg per day per adult in the case of oral administration, and the daily dose may be used once or by dividing it into 2 to 4.

Next, an example for the production of a pharmaceutical preparation for use in the oral administration of the compound of the present invention is described.

| Preparation example (50 mg/tablet) | |
|---|---|
| Composition | |
| Compound of Example 52 or 100 | 50 mg |
| Lactose | 72 |
| Corn Starch | 18 |
| Hydroxypropyl Cellulose | 5 |
| Carboxymethyl Cellulose Calcium | 4.2 |
| Magnesium Stearate | 0.8 |
| Total | 150 mg |

Making use of a fluid-bed granulation coating machine (Ohgawara Seisaku-sho), 175 g of the compound of Example 52 or 100 was uniformly mixed with 252 g of lactose and 63 g of corn starch. To this was sprayed 175 g of 10% hydroxypropyl cellulose solution to make the mixture into granules. After drying, the granules were passed through a 20 mesh sieve, mixed with 14.7 g of carboxymethyl cellulose calcium and 2.8 g of magnesium stearate and then made into tablets of 150 mg per tablet by a rotary tabletting machine (Hata Tekko-sho) using a mortar stamp system of 7.5 mm×8.4 R.

BEST MODE FOR CARRYING OUT THE INVENTION

The compound of the present invention and its production process described in the foregoing are further illustrated in detail by the following examples.

Since some of the starting compounds used in the Examples are novel compounds, their production processes are shown as Reference Examples.

Reference Example 1 (Starting compound of Example 1)

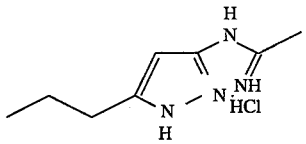

(A) N-(5-Propyl-1H-pyrazol-3-yl)acetamidine hydrochloride

A 11.5 g portion of 3-amino-5-propyl-1H-pyrazole was dissolved in 60 ml of acetonitrile, and 12.8 g of ethyl acetimidate hydrochloride was added to the above solution with cooling on an ice bath. The resulting mixture was stirred for 1 hour at the same temperature and then overnight at room temperature.

After removing insoluble materials by filtration, the filtrate was concentrated under a reduced pressure, and the resulting residue was subjected to silica gel column chromatography. Elution with methanol-chloroform (1:9–1:4, v/v) gave 9.89 g of the title compound.

(1) Nuclear magnetic resonance spectrum (DMSO-$d_6$, TMS) δ (ppm):
  0.89 (3H, t), 1.61 (2H, m), 2.39 (3H, s), 2.60 (2H, t), 5.99 (1H, s)

(2) Mass spectrometric data (EI): 166 ($M^+$)

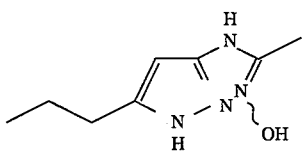

(B) N-(5-Propyl-1H-pyrazol-3-yl)acetamidoxime

A 1.71 g portion of sodium was added to 60 ml of methanol to prepare a sodium methoxide solution. A 4.96 g portion of hydroxylamine hydrochloride was added to the above solution and the thus formed sodium chloride was removed by filtration to prepare a methanol solution of hydroxylamine. On the other hand, 9.87 g of N-(5-propyl-1H-pyrazol-3-yl)acetamidine hydrochloride was dissolved in 50 ml of methanol and cooled on an ice bath.

To this was added dropwise the methanol solution of hydroxylamine prepared above, followed by overnight stirring at room temperature. The reaction mixture was concentrated to a ⅓ to ¼ volume under a reduced pressure, and the salts formed were removed by filtration and washed with a small volume of methanol. Thereafter, the combined methanol solution was concentrated under a reduced pressure and the thus obtained residue was subjected to silica gel column chromatography. Elution with methanol-chloroform (1:9–1:4, v/v) gave 5.42 g of the title compound in the form of colorless solid.

(1) Nuclear magnetic resonance spectrum (DMSO-$d_6$, TMS) δ (ppm):
  0.89 (3H, t), 1.57 (2H, m), 1.91 (3H, s), 2.48 (2H, t), 5.71 (1H, s)

(2) Mass spectrometric data (EI): 182 ($M^+$)

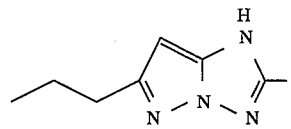

(C) 2-Methyl-6-propyl-1H-pyrazolo[1,5-b][1,2,4]triazole

A 5.38 g portion of N-(5-propyl-1H-pyrazol-3-yl)acetamidoxime was dissolved in 45 ml of N,N-dimethylacetamide. With cooling on an ice bath, to this were added 2.39 ml of pyridine and 5.63 g of p-toluenesulfonic acid chloride, followed by 30 minutes of stirring at the same temperature and additional 3 hours of stirring at room temperature. The resulting reaction mixture was added to 350 ml of water and extracted with chloroform. After distilling off chloroform from the organic layer under a reduced pressure, the thus obtained residue was dissolved in 135 ml of methanol, mixed with 2.39 ml of pyridine and then heated under reflux for 2 hours.

The reaction mixture was concentrated under a reduced pressure, and the resulting residue was subjected to silica gel column chromatography and elution was conducted with methanol-chloroform (1:19, v/v). Thereafter, fractions containing the compound of interest were concentrated under a reduced pressure, and the thus formed colorless crystals were dispersed in diisopropyl ether and collected by filtration to give 2.51 g of the title compound. This compound was used in Example 1 and Reference Example 9.

(1) Melting point: 196°–197° C.

(2) Nuclear magnetic resonance spectrum (DMSO-$d_6$, TMS) δ (ppm):
  0.91 (3H, t), 1.62 (2H, m), 2.37 (3H, s), 2.53 (2H, t), 5.53 (1H, s), 12.24 (1H, brs)

(3) Mass spectrometric data (EI): 164 ($M^+$)

Reference Example 2 (Starting compound of Example 3)

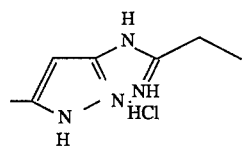

(A) N-(5-Methyl-1H-pyrazol-3-yl)propionamidine hydrochloride

A 13.8 g portion of 3-amino-5-methyl-1H-pyrazole was dissolved in 52 ml of acetonitrile, and 22.0 g of ethyl propionimidate hydrochloride was added to the above solution with cooling on an ice bath. The resulting mixture was stirred for 1 hour at the same temperature and then overnight at room temperature.

The solid material formed was collected by filtration and dissolved in a methanol-chloroform (1:4, v/v) mixed solvent. After removing insoluble materials by filtration, the resulting filtrate was concentrated under a reduced pressure, and the thus obtained colorless solid material was dispersed in an acetonitrile-diisopropyl ether (1:1, v/v) mixed solvent and collected by filtration to give 15.1 g of the title compound.

(1) Nuclear magnetic resonance spectrum (DMSO-$d_6$, TMS) δ (ppm):
  1.29 (3H, t), 2.27 (3H, s), 2.69 (2H, q), 6.03 (1H, s)
(2) Mass spectrometric data (EI): 152 (M$^+$)

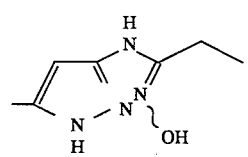

(B) N-(5-Methyl-1H-pyrazol-3-yl)propionamidoxime

In the same manner as the procedure of the step B of Reference Example 1, 7.57 g of the title compound was obtained from 9.86 g of N-(5-methyl-1H-pyrazol-3-yl)propionamidine hydrochloride.

(1) Nuclear magnetic resonance spectrum (DMSO-$d_6$, TMS) δ (ppm):
  0.95 (3H, t), 2.15 (3H, s), 2.39 (2H, q), 5.69 (1H, s)
(2) Mass spectrometric data (EI): 168 (M$^+$)

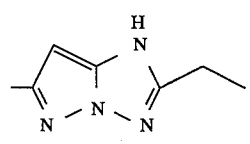

(C) 2-Ethyl-6-methyl-1H-pyrazolo[1,5-b][1,2,4]triazole

In the same manner as the procedure of the step C of Reference Example 1, 2.12 g of the title compound was obtained in the form of yellow solid from 7.55 g of N-(5-methyl-1H-pyrazol-3-yl)propionamidoxime. This compound was used in Example 3 without further purification.

(1) Nuclear magnetic resonance spectrum (DMSO-$d_6$, TMS) δ (ppm):
  1.26 (3H, t), 2.22 (3H, s), 2.73 (2H, q), 5.51 (1H, s), 12.24 (1H, brs)
(2) Mass spectrometric data (EI): 150 (M$^+$)

Reference Example 3 (Starting compound of Example 4)

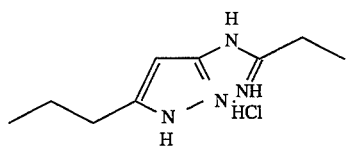

(A) N-(5-Propyl-1H-pyrazol-3-yl)propionamidine hydrochloride

In the same manner as the procedure of the step A of Reference Example 1, 4.20 g of the title compound was obtained from 4.32 g of 3-amino-5-propyl-1H-pyrazole and 5.37 g of ethyl propionimidate hydrochloride.

(1) Nuclear magnetic resonance spectrum (DMSO-$d_6$, TMS) δ (ppm):
  0.90 (3H, t), 1.28 (3H, t), 1.62 (2H, m), 2.53–2.78 (4H, m), 6.02 (1H, s)
(2) Mass spectrometric data (EI): 180 (M$^+$)

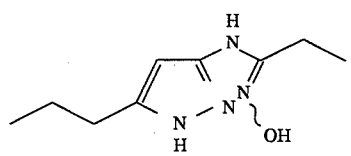

(B) N-(5-Propyl-1H-pyrazol-3-yl)propionamidoxime

In the same manner as the procedure of the step B of Reference Example 1, 3.58 g of the title compound was obtained from 4.19 g of N-(5-propyl-1H-pyrazol-3-yl)propionamidine hydrochloride.

(1) Nuclear magnetic resonance spectrum (DMSO-$d_6$, TMS) δ (ppm):
  0.89 (3H, t), 0.94 (3H, t), 1.57 (2H, m), 5.70 (1H, s)
(2) Mass spectrometric data (EI): 196 (M$^+$)

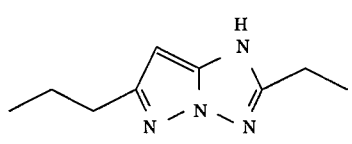

(C) 2-Ethyl-6-propyl-1H-pyrazolo[1,5-b][1,2,4]triazole

In the same manner as the procedure of the step C of Reference Example 1, 0.51 g of the title compound was obtained in the form of colorless crystals from 3.56 g of N-(5-propyl-1H-pyrazol-3-yl)propionamidoxime.

(1) Melting point: 161°–163° C.
(2) Nuclear magnetic resonance spectrum (DMSO-d₆, TMS) δ (ppm):
0.91 (3H, t), 1.26 (3H, t), 1.61 (2H, m), 2.53 (2H, t), 2.72 (2H, q), 5.52 (1H, s), 12.26 (1H, brs)
(3) Mass spectrometric data (EI): 178 (M⁺)

Reference Example 4 (Starting compound of Example 5)

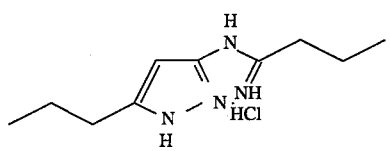

(A) N-(5-Propyl-1H-pyrazol-3-yl)butylamidine hydrochloride

In the same manner as the procedure of the step A of Reference Example 1, 4.30 g of the title compound was obtained from 4.02 g of 3-amino-5-propyl-1H-pyrazole and 5.50 g of ethyl butylimidate hydrochloride.
(1) Nuclear magnetic resonance spectrum (DMSO-d₆, TMS) δ (ppm):
0.83–1.02 (6H, m), 1.45–1.96 (4H, m), 2.48–2.72 (4H, m), 6.02 (1H, s)
(2) Mass spectrometric data (EI): 194 (M⁺)

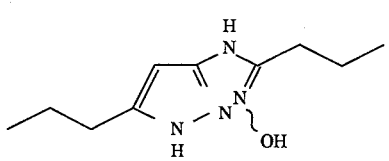

(B) N-(5-Propyl-1H-pyrazol-3-yl)butylamidoxime

In the same manner as the procedure of the step B of Reference Example 1, 3.47 g of the title compound was obtained in the form of colorless solid from 4.21 g of N-(5-propyl-1H-pyrazol-3-yl)butylamidine hydrochloride.
(1) Nuclear magnetic resonance spectrum (DMSO-d₆, TMS) δ (ppm):
0.76–0.96 (6H, m), 1.24–1.77 (4H, m), 2.29–2.56 (4H, m), 5.71 (1H, s)
(2) Mass spectrometric data (EI): 210 (M⁺)

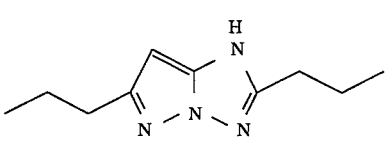

(C) 2,6-Dipropyl-1H-pyrazolo[1,5-b][1,2,4]triazole

In the same manner as the procedure of the step C of Reference Example 1, 0.88 g of the title compound was obtained in the form of colorless crystals from 3.42 g of N-(5-propyl-1H-pyrazol-3-yl)butylamidoxime.
(1) Melting point: 126°–128° C.

(2) Nuclear magnetic resonance spectrum (DMSO-d₆, TMS) δ (ppm):
0.91 (3H, t), 0.94 (3H, t), 1.41–1.83 (4H, m), 2.45–2.75 (4H, m), 5.52 (1H, s), 12.24 (1H, brs)
(3) Mass spectrometric data (EI): 192 (M⁺)

Reference Example 5 (Starting compound of Example 6)

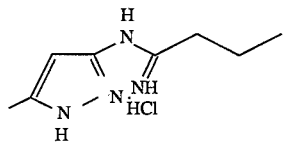

(A) N-(5-Methyl-1H-pyrazol-3-yl)butylamidine hydrochloride

In the same manner as the procedure of the step A of Reference Example 1, 24.4 g of the title compound was obtained from 15.9 g of 3-amino-5-methyl-1H-pyrazole and 28.1 g of ethyl butylimidate hydrochloride.
(1) Nuclear magnetic resonance spectrum (DMSO-d₆, TMS) δ (ppm):
0.94 (3H, t), 1.74 (2H, m), 2.26 (3H, s) 2.62 (2H, t), 6.00 (mH, s)
(2) Mass spectrometric data (FAB): 167 (MH⁺)

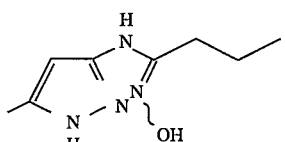

(B) N-(5-Methyl-1H-pyrazol-3-yl)butylamidoxime

In the same manner as the procedure of the step B of Reference Example 1, 21.7 g of the title compound was obtained from 24.3 g of N-(5-methyl-1H-pyrazol-3-yl)butylamidine hydrochloride.
(1) Nuclear magnetic resonance spectrum (DMSO-d₆, TMS) δ (ppm):
0.83 (3H, t), 1.40 (2H, m), 2.16 (3H, s), 2.37 (2H, t), 5.69 (1H, s)
(2) Mass spectrometric data (FAB): 183 (MH⁺)

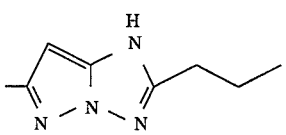

(C) 6-Methyl-2-propyl-1H-pyrazolo[1,5-b][1,2,4]triazole

In the same manner as the procedure of the step C of Reference Example 1, 2.64 g of the title compound was obtained in the form of orange solid from 21.6 g of N-(5-methyl-1H-pyrazol-3-yl)butylamidoxime. This compound was used in Example 6 and Reference Example 10 without further purification.

(1) Nuclear magnetic resonance spectrum (DMSO-d$_6$, TMS) δ (ppm):
0.93 (3H, t), 1.71 (2H, m), 2.22 (3H, s), 2.67 (2H, t), 5.51 (1H, s), 12.22 (1H, brs)

(2) Mass spectrometric data (EI): 164 (M$^+$)

Reference Example 6 (Starting compound of Example 7)

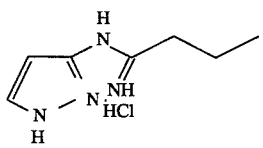

(A) N-(1H-Pyrazol-3-yl)butylamidine hydrochloride

In the same manner as the procedure of the step A of Reference Example 1, 13.8 g of the title compound was obtained from 10.3 g of 3-amino-1H-pyrazole and 21.2 g of ethyl butylimidate hydrochloride.

(1) Nuclear magnetic resonance spectrum (DMSO-d$_6$, TMS) δ (ppm):
0.95 (3H, t), 1.76 (2H, m), 2.63 (2H, t), 6.23 (1H, s), 7.88 (1H, s)

(2) Mass spectrometric data (EI): 152 (M$^+$)

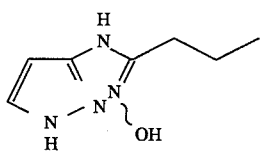

(B) N-(1H-Pyrazol-3-yl)butylamidoxime

In the same manner as the procedure of the step B of Reference Example 1, 3.33 g of the title compound was obtained in the form of colorless solid from 7.11 g of N-(1H-pyrazol-3-yl)butylamidine hydrochloride.

(1) Nuclear magnetic resonance spectrum (DMSO-d$_6$, TMS) δ (ppm):
0.82 (3H, t), 1.39 (2H, m), 5.93 (1H, s), 7.54 (1H, s)

(2) Mass spectrometric data (FAB): 169 (MH$^+$)

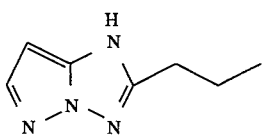

(c) 2-Propyl-1H-pyrazolo[1,5-b][1,2,4]triazole

In the same manner as the procedure of the step C of Reference Example 1, 0.92 g of the title compound was obtained in the form of colorless crystals from 3.33 g of N-(1H-pyrazol-3-yl)butylamidoxime. This compound was used as the starting compound of Example 7.

(1) Melting point: 145°–147° C.

(2) Nuclear magnetic resonance spectrum (DMSO-d$_6$, TMS) δ (ppm):

0.94 (3H, t), 1.74 (2H, m), 2.71 (2H, t), 5.74 (1H, d), 7.40 (1H, d), 12.44 (1H, brs)

(3) Mass spectrometric data (EI): 150 (M$^+$)

Reference Example 7 (Starting compound of Example 8)

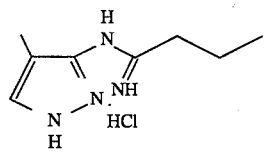

(A) N-(4-Methyl-1H-pyrazol-3-yl)butylamidine hydrochloride

In the same manner as the procedure of the step A of Reference Example 1, 6.72 g of the title compound was obtained from 5.13 g of 3-amino-4-methyl-1H-pyrazole and 9.07 g of ethyl butylimidate hydrochloride.

(1) Nuclear magnetic resonance spectrum (DMSO-d$_6$, TMS) δ (ppm):
0.97 (3H, t), 1.77 (2H, m), 2.09 (3H, d), 2.75 (2H, t), 7.67 (1H, q)

(2) Mass spectrometric data (EI): 166 (M$^+$)

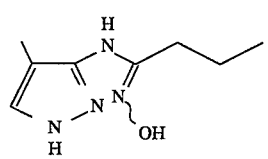

(B) N-(4-Methyl-1H-pyrazol-3-yl)butylamidoxime

In the same manner as the procedure of the step B of Reference Example 1, 6.52 g of the title compound was obtained from 6.69 g of N-(4-methyl-1H-pyrazol-3-yl)butylamidine hydrochloride.

(1) Nuclear magnetic resonance spectrum (DMSO-d$_6$, TMS) δ (ppm):
0.76 (3H, t), 1.30 (2H, m), 1.88 (3H, d), 2.17 (2H, t), 7.41 (1H, q)

(2) Mass spectrometric data (FAB): 183 (MH$^+$)

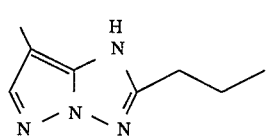

(C) 7-Methyl-2-propyl-1H-pyrazolo[1,5-b][1,2,4]triazole

In the same manner as the procedure of the step C of Reference Example 1, 1.54 g of the title compound was obtained in the form of colorless crystals from 6.50 g of N-(4-methyl-1H-pyrazol-3-yl)butylamidoxime. This compound was used as the starting compound of Example 8.

(1) Melting point: 212°–214° C.

(2) Nuclear magnetic resonance spectrum (DMSO-d$_6$,

TMS) δ (ppm):
0.94 (3H, t), 1.72 (2H, m), 2.08 (3H, d), 2.69 (2H, t), 7.18 (1H, q), 12.30 (1H, brs)

(3) Mass spectrometric data (EI): 164 (M⁺)

Reference Example 8 (Starting compound of Example 9)

(A) 3-Amino-4-methyl-5-propyl-1H-pyrazole

A two liter capacity three neck flask was cooled using a dry ice-acetone mixture and then charged with about 600 ml of liquid ammonia. With mechanical vigorous agitation, 21.2 g of sodium amide was added at once and, after 5 minutes thereof, 36.4 ml of propionitrile was added dropwise spending 5 minutes, followed by 5 minutes of reaction.

To this was added dropwise 29.2 ml of methyl butanoate spending 5 minutes, followed by 1 hour of reaction at the same temperature. In a stream of argon, the reaction vessel was heated on a water bath of about 40° C. to distill off ammonia. To the thus obtained white solid material were added 30 ml of ether and 150 ml of ice water, followed by the adjustment of the resulting mixture to strong acidity with 6N hydrochloric acid aqueous solution.

The resulting organic layer was collected and mixed with 70 ml of ethanol and 22.0 ml of hydrazine monohydrate, ether was removed from the mixture by distillation under normal pressure and then the thus obtained ethanol solution was heated overnight under reflux.

The reaction solution was concentrated under a reduced pressure, and the resulting residue was subjected to silica gel column chromatography. Elution with methanol-chloroform (1:19, v/v) gave 25.0 g of the title compound in the form of oily material.

(1) Nuclear magnetic resonance spectrum (DMSO-$d_6$, TMS) δ (ppm):
0.93 (3H, t), 1.59 (2H, m), 1.85 (3H, s), 2.47 (2H, t)

(2) Mass spectrometric data (EI): 139 (M⁺)

(B) N-(4-Methyl-5-propyl-1H-pyrazol-3-yl)acetamidine hydrochloride

In the same manner as the procedure of the step A of Reference Example 1, 19.0 g of the title compound was obtained from 24.6 g of 3-amino-4-methyl-5-propyl-1H-pyrazole and 24.7 g of ethyl acetimidate hydrochloride.

(1) Nuclear magnetic resonance spectrum (DMSO-$d_6$, TMS) δ (ppm):
0.87 (3H, t), 1.58 (2H, m), 2.01 (3H, s), 2.46 (3H, s), 2.55 (2H, t)

(2) Mass spectrometric data (FAB): 181 (MH⁺)

(C) N-(4-Methyl-5-propyl-1H-pyrazol-3-yl)acetamidoxime

In the same manner as the procedure of the step B of Reference Example 1, 16.2 g of the title compound was obtained from 18.9 g of N-(4-methyl-5-propyl-1H-pyrazol-3-yl)acetamidine hydrochloride.

(1) Nuclear magnetic resonance spectrum (DMSO-$d_6$, TMS) δ (ppm):
0.87 (3H, t), 1.55 (2H, m), 1.72 (3H, s), 1.80 (3H, s), 2.47 (2H, t)

(2) Mass spectrometric data (FAB): 197 (MH⁺)

(D) 2,7-Dimethyl-6-propyl-1H-pyrazolo[1,5-b][1,2,4]triazole

In the same manner as the procedure of the step C of Reference Example 1, 7.97 g of the title compound was obtained in the form of colorless crystals from 16.1 g of N-(4-methyl-5-propyl-1H-pyrazol-3-yl)acetamidoxime. This was used as the starting compound of Example 9.

(1) Melting point: 194°–195° C.
(2) Nuclear magnetic resonance spectrum (DMSO-$d_6$, TMS) δ (ppm):
0.90 (3H, t), 1.58 (2H, m), 2.01 (3H, s), 2.35 (3H, s), 2.50 (2H, t), 12.15 (1H, brs)

(3) Mass spectrometric data (EI): 178 (M⁺)

Reference Example 9 (Starting compound of Example 10)

7-Chloro-2-methyl-6-propyl-1H-pyrazolo[1,5-b]-[1,2,4]triazole

A 677 mg portion of 2-methyl-6-propyl-1H-pyrazolo-[1,5-b][1,2,4]triazole was dissolved in a mixed solvent consisting of 40 ml of tetrahydrofuran and 80 ml of dichloromethane. A 550 mg portion of N-chlorosuccinimide was added to the thus prepared solution and stirred at room temperature for 20 minutes, and the reaction mixture was washed twice with sodium bicarbonate aqueous solution and then once with water.

The resulting organic layer was dried over anhydrous magnesium sulfate and the solvent was removed by distillation under a reduced pressure. Thereafter, the thus formed crystals were dispersed in diisopropyl ether and collected by filtration to give 671 mg of the title compound in the form of colorless crystals. This compound was used later in Example 10.

(1) Melting point: 198°–199° C.
(2) Nuclear magnetic resonance spectrum (DMSO-$d_6$, TMS) δ (ppm):
   0.91 (3H, t), 1.63 (2H, m), 2.39 (3H, s), 2.55 (2H, t), 12.91 (1H, brs)
(3) Mass spectrometric data (EI): 198 ($M^+$)

Reference Example 10 (Starting compound of Example 11)

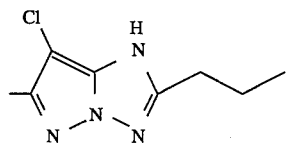

7-Chloro-6-methyl-2-propyl-1H-pyrazolo[1,5-b]-[1,2,4]triazole

In the same manner as the procedure of Reference Example 9, 556 mg of the title compound was obtained in the form of orange solid from 600 mg of 6-methyl-2-propyl-1H-pyrazolo[1,5-b][1,2,4]triazole. This compound was used in Example 11 without further purification.

(1) Nuclear magnetic resonance spectrum (DMSO-$d_6$, TMS) δ (ppm):
   0.93 (3H, t), 1.72 (2H, m), 2.20 (3H, s), 2.70 (2H, t), 12.87 (1H, brs)
(2) Mass spectrometric data (EI): 198 ($M^+$)

Example 1

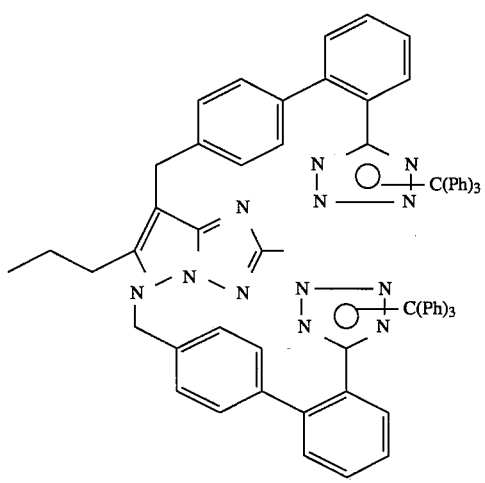

(1a)

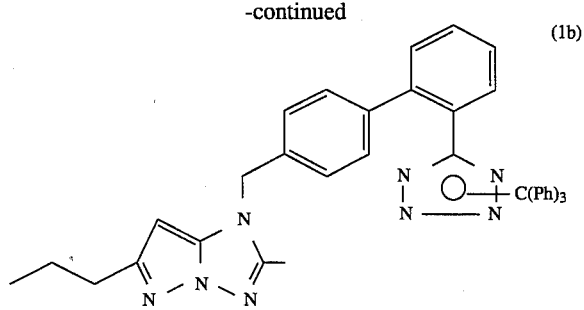

(1b)

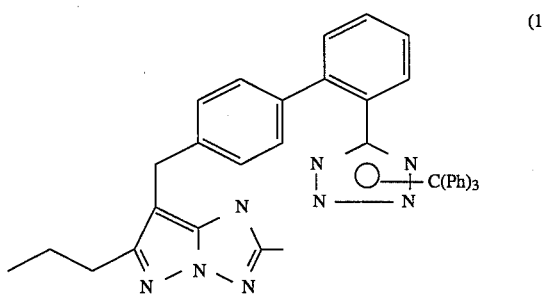

(1c)

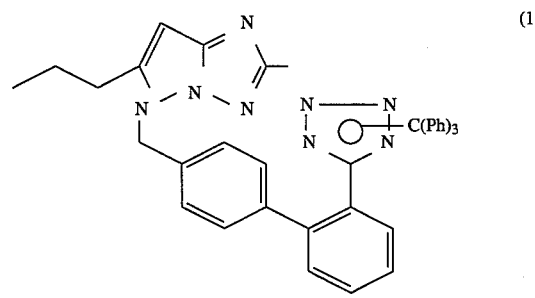

(1d)

mixture

A 1.75 g portion of 2-methyl-6-propyl-1H-pyrazolo[1,5-b][1,2,4]triazole was dissolved in 70 ml of N,N-dimethylformamide, 1.19 g of potassium t-butoxide was added to the solution, and the mixture was stirred for 30 minutes at room temperature. The resulting reaction mixture was cooled on an ice bath and mixed with 6.52 g of N-triphenylmethyl-5-[2-(4'-bromomethyl-biphenylyl)]tetrazole, and the mixture was stirred for 1 hour at the same temperature and then overnight at room temperature.

After removing the solvent by distillation under a reduced pressure, the thus obtained residue was mixed with ethyl acetate and washed twice with water. The resulting ethyl acetate layer was dried over anhydrous magnesium sulfate and concentrated under a reduced pressure, and the thus obtained residue was subjected to silica gel column chromatography. Elution with ethyl acetate-n-hexane (7:13–4:1, v/v) gave 0.38 g of 5,7-bis[[2'-(N-triphenylmethyl-tetrazol-5-yl)biphenyl-4-yl]methyl]-2-methyl-6-propyl-5H-pyrazolo[1,5-b][1,2,4]triazole (compound 1a), 2.91 g of 2-methyl-6-propyl-1-[[2'-(N-triphenylmethyl-tetrazol-5-yl)biphenyl-4-yl]methyl]-1H-pyrazolo[1,5-b][1,2,4]triazole (compound 1b), 0.20 g of 2-methyl-6-propyl-7-[[2'-(N-triphenylmethyl-tetrazol-5-yl)biphenyl-4-yl]methyl]-1H-pyrazolo[1,5-b][1,2,4]triazole (compound 1c) and 1.89 g of a mixture (about 3:1) of 2-methyl-6-propyl-5-[[2'-(N-triphenylmethyl-tetrazol-5-yl)biphenyl-4-yl]methyl]-5H-pyrazolo[1,5-b][1,2,4]triazole (compound 1d) and 2-methyl-6-propyl-1H-pyrazolo[1,5-b][1,2,4]triazole.

Compound 1a;

(1) Nuclear magnetic resonance spectrum (CDCl₃, TMS) δ (ppm):

0.82 (3H, t), 1.38 (2H, m), 2.44 (2H, t), 2.48 (3H, s), 3.85 (2H, s), 5.21 (2H, s)

(2) Mass spectrometric data (FAB): 1117 (MH⁺)

Compound 1b;

(1) Nuclear magnetic resonance spectrum (CDCl₃, TMS) δ (ppm):

0.95 (3H, t), 1.67 (2H, m), 2.32 (3H, 2.63 (2H, t), 4.92 (2H, s), 5.27 (1H, s)

(2) Mass spectrometric data (FAB): 641 (MH⁺)

Compound 1c;

(1) Nuclear magnetic resonance spectrum (CDCl₃, TMS) δ (ppm):

1.04 (3H, t) , 1.79 (2H, m), 1.86 (3H, s), 2.72 (2H, t), 3.82 (2H, s)

(2) Mass spectrometric data (FAB): 641 (MH⁺)

Example 2

The following compounds were obtained from 2.60 g of 2,6-dimethyl-1H-pyrazolo[1,5-b][1,2,4]triazole in the same manner as described in Example 1: 0.90 g of 5,7-bis[[2'-(N-triphenylmethyl-tetrazol- 5-yl)biphenyl-4-yl]methyl]-2,6 -dimethyl-5H-pyrazolo[1,5-b][1,2,4]triazole (compound 2a), 3.90 g of 2,6-dimethyl-1-[[2'-(N-triphenylmethyl-tetrazol-5 -yl)biphenyl-4-yl]methyl]-1H-pyrazolo[1,5-b][1,2,4]triazole (compound 2b) (colorless crystals), 0.43 g of 2,6-dimethyl-7 -[[2'-(N-triphenylmethyl-tetrazol-5-yl)biphenyl-4-yl]methyl] -1H-pyrazolo[1,5-b][1,2,4]triazole (compound 2c) and 2.92 g of 2,6-dimethyl-5-[[2'-(N-triphenylmethyl-tetrazol-5 -yl)biphenyl-4-yl]methyl]-5H-pyrazolo[1,5-b][1, 2,4]triazole (compound 2d) (colorless crystals).

Compound 2a;

(1) Nuclear magnetic resonance spectrum (CDCl₃, TMS) δ (ppm):

2.00 (3H, s), 2.48 (3H, s), 3.81 (2H, s), 5.18 (2H, s)

(2) Mass spectrometric data (FAB): 1089 (MH⁺)

Compound 2b;

(1) Melting point: 182°–183° C. (decomposition)

(2) Nuclear magnetic resonance spectrum (CDCl₃, TMS) δ (ppm):

2.31 (3H, s), 2.33 (3H, s), 4.91 (2H, s), 5.23 (1H, s)

(3) Mass spectrometric data (FAB): 613 (MH⁺)

Compound 2c;

(1) Nuclear magnetic resonance spectrum (CDCl₃, TMS) δ (ppm):

1.87 (3H, s), 2.38 (3H, s), 3.79 (2H, s)

(2) Mass spectrometric data (FAB): 613 (MH⁺)

Compound 2d;

(1) Melting point: 192°–193° C. (decomposition)

(2) Nuclear magnetic resonance spectrum (CDCl₃, TMS) δ (ppm):

2.20 (3H, s), 2.46 (3H, s), 5.26 (2H, s), 5.89 (1H, s)

(3) Mass spectrometric data (FAB): 613 (MH⁺)

Example 3

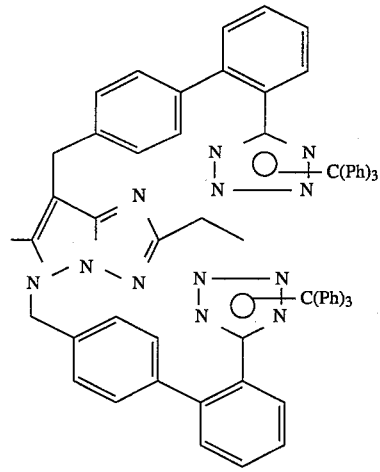

(3a)

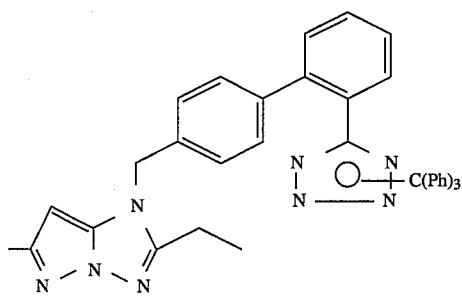

(3b)

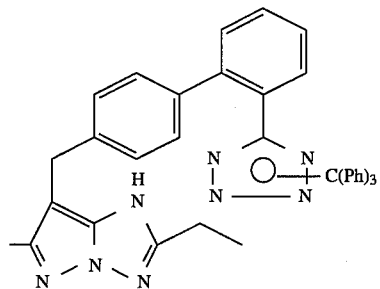

(3c)

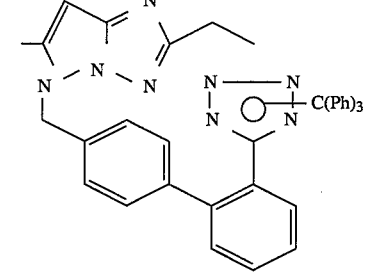

(3d)

The following compounds were obtained from 524 mg of 2-ethyl-6-methyl-1H-pyrazolo[1,5-b][1,2,4]triazole in the same manner as described in Example 1: 193 mg of 5,7-bis [[2' -(N-triphenylmethyl-tetrazol- 5-yl)biphenyl-4-yl]methyl]-2 -ethyl-6-methyl-5H-pyrazolo[1,5-b][1,2,4]triazole (compound 3a), 610 mg of 2-ethyl-6-methyl-1-[[2'-(N-triphenylmethyl-tetrazol- 5-yl)biphenyl-4-yl]methyl]-1H-pyrazolo[ 1,5-b][1,2,4]triazole (compound 3b), 45 mg of 2 -ethyl-6-methyl-7-[[2'-(N-triphenylmethyl-tetrazol-5 -yl)biphenyl-4-yl]methyl]-1H-pyrazolo[1,5-b][1,2,4]triazole (compound 3c) and 649 mg of 2-ethyl-6-methyl-5-[[2'-(N-triphenylmethyl-tetrazol- 5-yl)biphenyl-4-yl]methyl]-5H- pyrazolo[1,5-b][1,2,4]triazole (compound 3d).

Compound 3a;
(1) Nuclear magnetic resonance spectrum (CDCl₃, TMS) δ (ppm):
1.39 (3H, t), 1.99 (3H, brs), 2.87 (2H, brs), 3.85 (2H, brs), 5.19 (2H, s)
(2) Mass spectrometric data (FAB): 1103 (MH⁺)

Compound 3b;
(1) Nuclear magnetic resonance spectrum (CDCl₃, TMS) δ (ppm):
1.31 (3H, t), 2.31 (3H, s), 2.66 (2H, q), 4.92 (2H, s), 5.19 (1H, s)
(2) Mass spectrometric data (FAB): 627 (MH⁺)

Compound 3c;
(1) Nuclear magnetic resonance spectrum (CDCl₃, TMS) δ (ppm):
0.95 (3H, t), 2.25 (2H, q), 2.37 (3H, s), 3.79 (2H, s)
(2) Mass spectrometric data (FAB): 627 (MH⁺)

Compound 3d;
(1) Nuclear magnetic resonance spectrum (CDCl₃, TMS) δ (ppm):
1.36 (3H, t), 2.19 (3H, s), 2.81 (2H, q), 5.27 (2H, s), 5.89 (1H, s)
(2) Mass spectrometric data (FAB): 627 (MH⁺)

Example 4

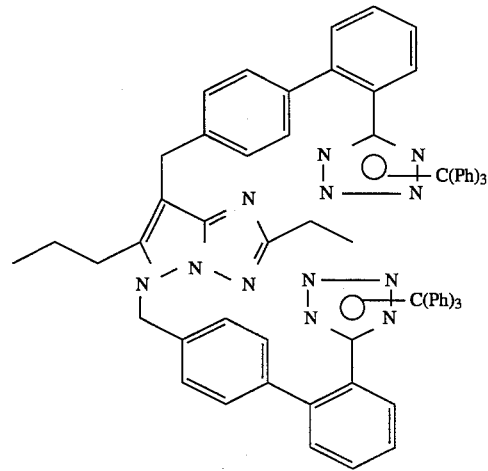
(4a)

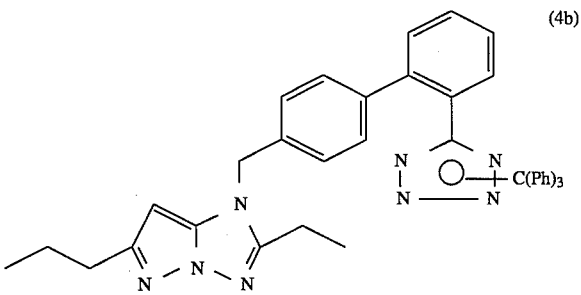
(4b)

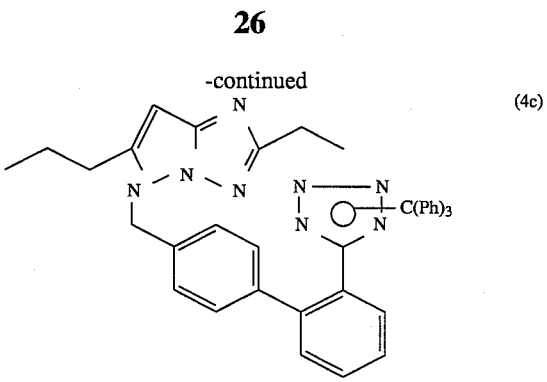
(4c)

A 421 mg portion of 2-ethyl-6-n-propyl-1H-pyrazolo[1,5-b][1,2,4]triazole used as the starting material was treated in the same manner as described in Example 1, and the resulting residue was subjected to silica gel column chromatography. Elution with ethyl acetate-n-hexane (7:13–1:1, v/v) gave 144 mg of 5,7-bis[[2'-(N-triphenylmethyl-tetrazol-5-yl)biphenyl-4-yl]methyl]-2-ethyl-6-propyl-5H-pyrazolo[1,5-b][1,2,4]triazole (compound 4a), 504 mg of 2-ethyl-6-propyl-1-[[2'-(N-triphenylmethyl-tetrazol-5-yl)biphenyl-4-yl]methyl]-1H-pyrazolo[1,5-b][1,2,4]triazole (compound 4b) and 435 mg of 2-ethyl-6-propyl-5-[[2'-(N-triphenylmethyl-tetrazol-5-yl)biphenyl-4-yl]methyl]-5H-pyrazolo[1,5-b][1,2,4]triazole (compound 4c).

Compound 4a;
(1) Nuclear magnetic resonance spectrum (CDCl₃ TMS) δ (ppm):
0.80 (3H, t), 1.36 (3H, t), 2.39 (2H, t), 2.83 (2H, q), 3.85 (2H, s), 5.20 (2H, s)
(2) Mass spectrometric data (FAB): 1131 (MH⁺)

Compound 4b;
(1) Nuclear magnetic resonance spectrum (CDCl₃, TMS) δ (ppm):
0.95 (3H, t), 1.30 (3H, t), 1.67 (2H, m), 2.61–2.67 (4H, m), 4.92 (2H, s), 5.24 (1H, s)
(2) Mass spectrometric data (FAB): 655 (MH⁺)

Compound 4c;
(1) Nuclear magnetic resonance spectrum (CDCl₃, TMS) δ (ppm):
0.93 (3H, t), 1.36 (3H, t), 1.63 (2H, m), 2.48 (2H, t), 2.80 (2H, q), 5.28 (2H, s), 5.90 (1H, s)
(2) Mass spectrometric data (FAB): 655 (MH⁺)

Example 5

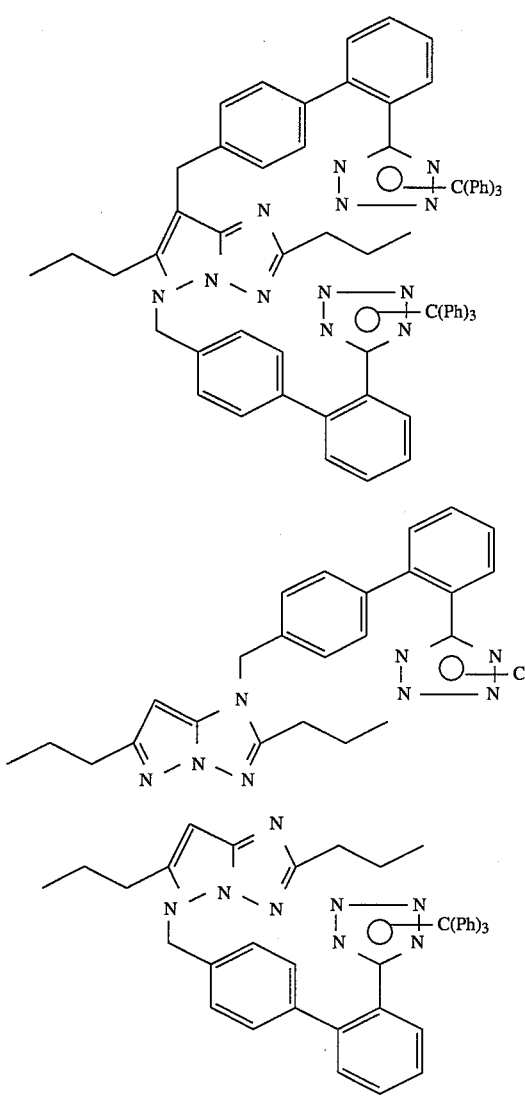

The following compounds were obtained from 420 mg of 2,6-dipropyl-1H-pyrazolo[1,5-b][1,2,4]triazole in the same manner as described in Example 4: 112 mg of 5,7-bis[[2'-(N-triphenylmethyl-tetrazol- 5-yl)biphenyl-4-yl]methyl]-2,6 -dipropyl-5H-pyrazolo[1,5-b][1,2,4]triazole (compound 5a), 456 mg of 2,6-dipropyl-1-[[2'-(N-triphenylmethyl-tetrazol-5 -yl)biphenyl-4-yl]methyl]-1H-pyrazolo[1,5-b][1,2,4]triazole (compound 5b) and 370 mg of 2,6-dipropyl-5-[[2'-(N-triphenylmethyl-tetrazol- 5-yl)biphenyl-4-yl]methyl]-5H-pyrazolo[ 1,5-b][1,2,4]triazole (compound 5c).

Compound 5a;
(1) Nuclear magnetic resonance spectrum (CDCl$_3$, TMS) δ (ppm):
0.80 (3H, t), 1.00 (3H, t), 1.35 (2H, m), 1.83 (2H, m), 2.40 (2H, t), 2.80 (2H, t), 3.85 (2H, s), 5.20 (2H, s)
(2) Mass spectrometric data (FAB): 1145 (MH$^+$)

Compound 5b;
(1) Nuclear magnetic resonance spectrum (CDCl$_3$, TMS) δ (ppm):
0.93–1.00 (6H, m), 1.67 (2H, m), 1.76 (2H, m), 2.60–2.64 (4H, m), 4.93 (2H, s), 5.22 (1H, s)
(2) Mass spectrometric data (FAB): 669 (MH$^+$)

Compound 5c;
(1) Nuclear magnetic resonance spectrum (CDCl$_3$, TMS) δ (ppm):
0.94 (3H, t), 0.99 (3H, t), 1.82 (2H, m), 2.48 (2H, t), 2.74 (2H, t), 5.28 (2H, s), 5.91 (1H, s)
(2) Mass spectrometric data (FAB): 669 (MH$^+$)

Example 6

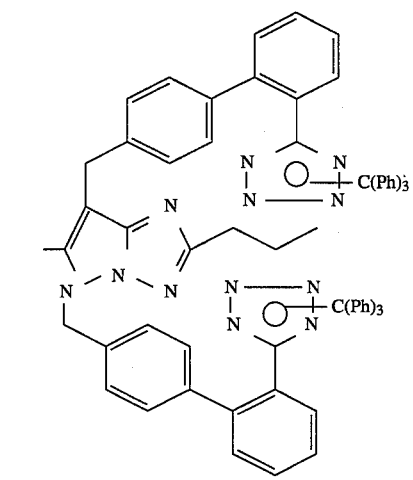

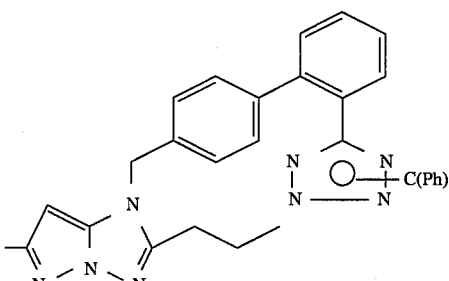

The following compounds were obtained from 316 mg of 6-methyl-2-propyl-1H-pyrazolo[1,5-b][1,2,4]triazole in the same manner as described in Example 4: 157 mg of 5,7-bis[[2' -(N-triphenylmethyl-tetrazol-5-yl)biphenyl-4-yl]methyl]-6 -methyl-2-propyl-5H-pyrazolo[1,5-b][1,2,4]triazole (compound 6a), 316 mg of 6-methyl-2-propyl-1-[[2'-(N-triphenylmethyl-tetrazol- 5-yl)biphenyl-4-yl]methyl]-1H-pyrazolo[ 1,5-b][1,2,4]triazole (compound 6b) and 368 mg of a mixture (about 2:1) consisting of 6-methyl-2-propyl-5-[[2' -(N-triphenylmethyl-tetrazol-5-yl)biphenyl-4-yl-]methyl]-5H-pyrazolo[ 1,5-b][1,2,4]triazole (compound 6c) and 6-methyl-2 -propyl-1H-pyrazolo[1,5-b][1,2,4]triazole.

Compound 6a;
(1) Nuclear magnetic resonance spectrum (CDCl$_3$, TMS) δ (ppm):

1.01 (3H, t), 1.84 (2H, m), 1.96 (3H, s), 2.78 (2H, t), 3.81 (2H, s), 5.17 (2H, s)

Compound 6b;

(1) Nuclear magnetic resonance spectrum (CDCl₃, TMS) δ (ppm):

0.99 (3H, t), 1.77 (2H, m), 2.30 (3H, s), 2.63 (2H, t), 4.92 (2H, s), 5.17 (1H, s)

(2) Mass spectrometric data (FAB): 641 (MH⁺)

Example 7

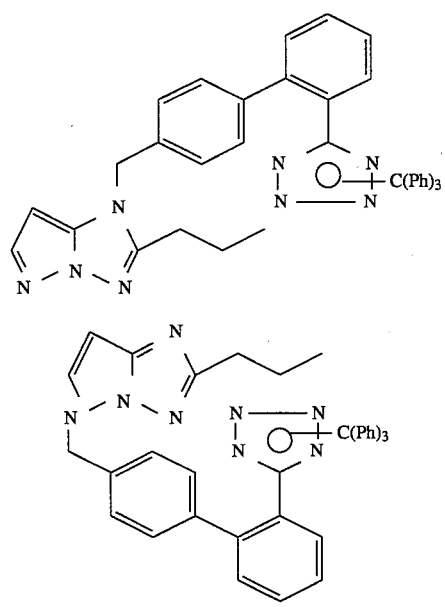

A 0.53 g portion of 2-propyl-1H-pyrazolo[1,5-b][1,2,4]triazole was treated in the same manner as described in Example 1, and the resulting residue was subjected to silica gel column chromatography. Elution with ethyl acetate-n-hexane (2:3–1:1, v/v) gave 1.00 g of 2-propyl-1-[[2'-(N-triphenylmethyl-tetrazol-5-yl)biphenyl-4-yl]methyl]-1H-pyrazolo[1,5-b][1,2,4]triazole (compound 7a) and 0.59 g of 2-propyl-5-[[2'-(N-triphenylmethyl-tetrazol-5-yl)biphenyl-4-yl]methyl]-5H-pyrazolo[1,5-b][1,2,4]triazole (compound 7b).

Compound 7a;

(1) Nuclear magnetic resonance spectrum (CDCl₃, TMS) δ (ppm):

1.01 (3H, t), 1.80 (2H, m), 2.66 (2H, t), 4.97 (2H, s), 5.37 (1H, d)

(2) Mass spectrometric data (FAB): 627 (MH⁺)

Compound 7b;

(1) Nuclear magnetic resonance spectrum (CDCl₃, TMS) δ (ppm):

1.02 (3H, t), 1.85 (2H, m), 2.80 (2H, t), 5.20 (2H, s), 6.01 (1H, d)

(2) Mass spectrometric data (FAB): 627 (MH⁺)

Example 8

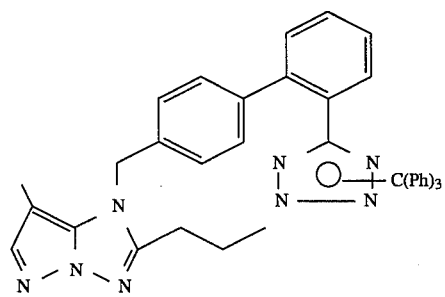

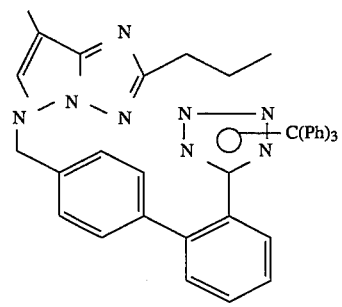

A 307 mg portion of 7-methyl-2-propyl-1H-pyrazolo[1,5-b][1,2,4]triazole was treated in the same manner as described in Example 1, and the resulting residue was subjected to silica gel column chromatography. Elution with ethyl acetate-n-hexane (1:1–11:9, v/v) gave 148 mg of 7-methyl-2-propyl-1-[[2'-(N-triphenylmethyl-tetrazol-5-yl)biphenyl-4-yl]methyl]-1H-pyrazolo[1,5-b][1,2,4]triazole (compound 8a) and 790 mg of 7-methyl-2-propyl-5-[[2'-(N-triphenylmethyl-tetrazol-5-yl)biphenyl-4-yl]methyl]-5H-pyrazolo[1,5-b][1,2,4]triazole (compound 8b).

Compound 8a;

(1) Nuclear magnetic resonance spectrum (CDCl₃, TMS) δ (ppm):

0.97 (3H, t), 1.75 (2H, m), 1.87 (3H, s), 2.60 (2H, t), 5.07 (2H, s), 5.20 (1H, s)

(2) Mass spectrometric data (FAB): 641 (MH⁺)

Compound 8b;

(1) Nuclear magnetic resonance spectrum (CDCl₃, TMS) δ (ppm):

1.02 (3H, t), 1.87 (2H, m), 2.12 (3H, s), 2.83 (2H, t), 5.11 (2H, s) (2) Mass spectrometric data (FAB): 641 (MH⁺)

Example 9

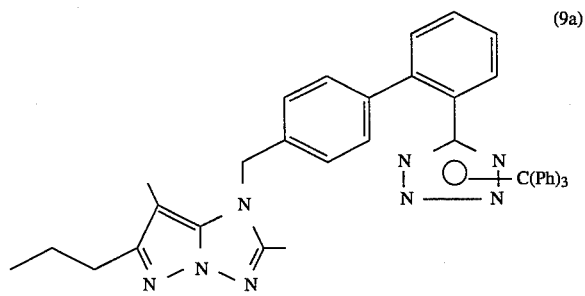

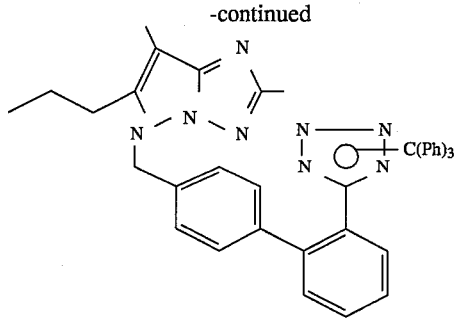

A 2.55 g portion of 2,7-dimethyl-6-propyl-1H-pyrazolo[1,5-b][1,2,4]triazole was treated in the same manner as described in Example 1, and the resulting residue was subjected to silica gel column chromatography. Elution with ethyl acetate-n-hexane (2:3–1:1, v/v) gave 1.15 g of 2,7-dimethyl-6-propyl-1-[[2'-(N-triphenylmethyl-tetrazol-5-yl)biphenyl-4-yl]methyl]-1H-pyrazolo[1,5-b][1,2,4]triazole (compound 9a) and 2.65 g of 2,7-dimethyl-6-propyl-5-[[2'-(N-triphenylmethyl-tetrazol-5-yl)biphenyl-4-yl]methyl]-5H-pyrazolo[1,5-b][1,2,4]triazole (compound 9b).

Compound 9a;

(1) Nuclear magnetic resonance spectrum (CDCl$_3$, TMS) δ (ppm):
0.97 (3H, t), 1.68 (2H, m), 1.88 (3H, s), 2.25 (3H, s), 2.59 (2H, t), 5.01 (2H, s)

(2) Mass spectrometric data (FAB): 655 (MH$^+$)

Compound 9b;

(1) Nuclear magnetic resonance spectrum (CDCl$_3$, TMS) δ (ppm):
0.90 (3H, t), 1.52 (2H, m), 2.14 (3H, s), 2.46 (3H, s), 2.48 (2H, t), 5.22 (2H, s)

(2) Mass spectrometric data (FAB): 655 (MH$^+$)

Example 10

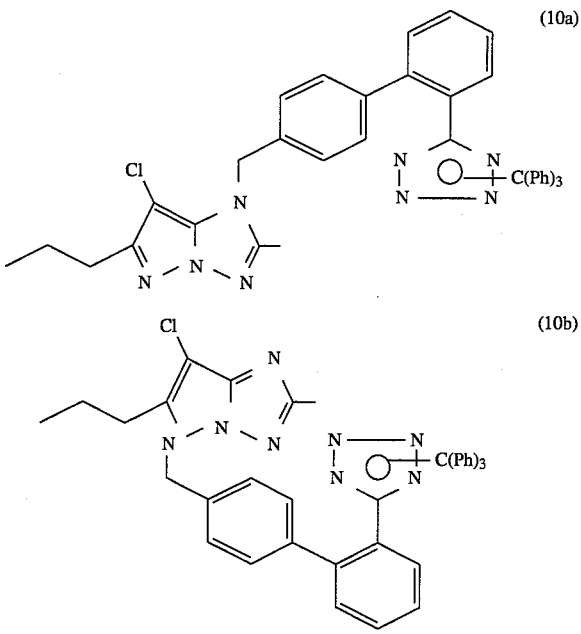

A 651 mg portion of 7-chloro-2-methyl-6-propyl-1H-pyrazolo[1,5-b][1,2,4]triazole was treated in the same manner as described in Example 1, and the resulting residue was subjected to silica gel column chromatography. Elution with ethyl acetate-n-hexane (7:13, v/v) gave 603 mg of 7-chloro-2-methyl-6-propyl-1-[[2'-(N-triphenylmethyl-tetrazol-5-yl)biphenyl-4-yl]methyl]-1H-pyrazolo[1,5-b][1,2,4]triazole (compound 10a) and 225 mg of 7-chloro-2-methyl-6-propyl-5-[[2'-(N-triphenylmethyl-tetrazol-5-yl)biphenyl-4-yl]methyl]-5H-pyrazolo[1,5-b][1,2,4]triazole (compound 10b).

Compound 10a;

(1) Nuclear magnetic resonance spectrum (CDCl$_3$, TMS) δ (ppm):
1.00 (3H, t), 1.76 (2H, m), 2.24 (3H, s), 2.69 (2H, t), 5.07 (2H, s)

(2) Mass spectrometric data (FAB): 674 (MH$^+$)

Compound 10b;

(1) Nuclear magnetic resonance spectrum (CDCl$_3$, TMS) δ (ppm):
0.94 (3H, t), 1.59 (2H, m), 2.50 (3H, s ), 2.61 (2H, t), 5.29 (2H, s)

(2) Mass spectrometric data (FAB): 675 (MH$^+$)

Example 11

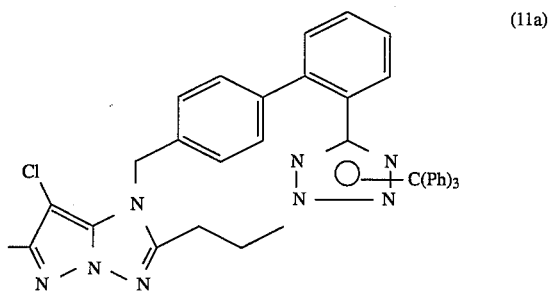

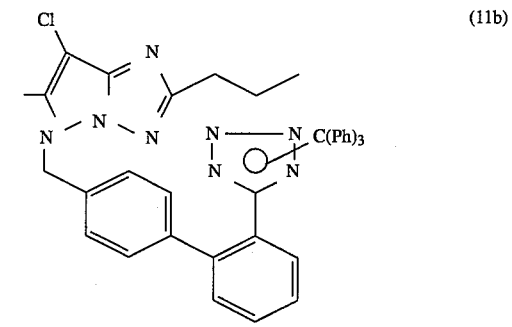

A 500 mg portion of 7-chloro-6-methyl-2-propyl-1H-pyrazolo[1,5-b][1,2,4]triazole was treated in the same manner as described in Example 10 to give 460 mg of 7-chloro-6-methyl-2-propyl-1-[[2'-(N-triphenylmethyl-tetrazol-5-yl)biphenyl-4-yl]methyl]-1H-pyrazolo[1,5-b][1,2,4]triazole (compound 11a) and 776 mg of 7-chloro-6-methyl-2-propyl-5-[[2'-(N-triphenylmethyl-tetrazol-5-yl)biphenyl-4-yl]methyl]-5H-pyrazolo[1,5-b][1,2,4]triazole (compound 11b).

Compound 11a;

(1) Nuclear magnetic resonance spectrum (CDCl$_3$, TMS) δ (ppm):
0.94 (3H, t), 1.71 (2H, m), 2.34 (3H, s), 2.53 (2H, t), 5.08 (2H, s)

(2) Mass spectrometric data (FAB): 674 (M$^+$)

Compound 11b;

(1) Nuclear magnetic resonance spectrum (CDCl$_3$, TMS) δ (ppm):
0.99 (3H, t), 1.83 (2H, m), 2.19 (3H, s), 2.76 (2H, t), 5.26 (2H, s)

(2) Mass spectrometric data (FAB): 675 (MH$^+$)

Example 12

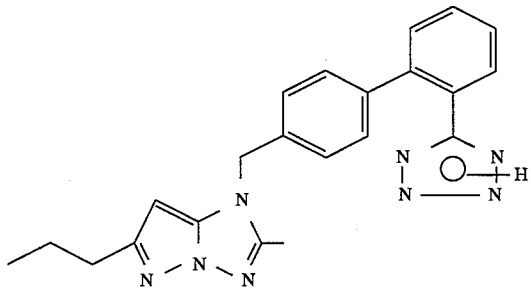

A mixture consisting of 1.00 g of 2-methyl-6-propyl-1-[[2'-(N-triphenylmethyl-tetrazol-5-yl)biphenyl-4-yl]methyl]-1H-pyrazolo[1,5-b][1,2,4]triazole (compound 1b), 54 ml of methanol and 6 ml of acetic acid was heated under reflux for 3 hours.

After removing the solvent by distillation under a reduced pressure, the resulting residue was mixed with toluene and again subjected to distillation under a reduced pressure. By adding ethyl acetate to the resulting residue for crystallization, 0.58 g of 2-methyl-6-propyl-1-[[2'-(tetrazol-5-yl)biphenyl-4-yl]methyl]-1H-pyrazolo[1,5-b][1,2,4]triazole was obtained in the form of colorless crystals.

(1) Melting point: 233°–234° C.

(2) Elemental analysis data (for C$_{22}$H$_{22}$N$_8$)

|  | C (%) | H (%) | N (%) |
|---|---|---|---|
| calculated: | 66.31 | 5.56 | 28.12 |
| found: | 66.14 | 5.68 | 28.03 |

(3) Nuclear magnetic resonance spectrum (DMSO-d$_6$, TMS) δ (ppm):
0.90 (3H, t), 1.59 (2H, m), 2.45 (3H, s), 2.51 (2H, t), 5.20 (2H, s), 5.34 (1H, s), 7.12 (2H, d), 7.28 (2H, d)

(4) Mass spectrometric data (FAB): 399 (MH$^+$)

Example 13

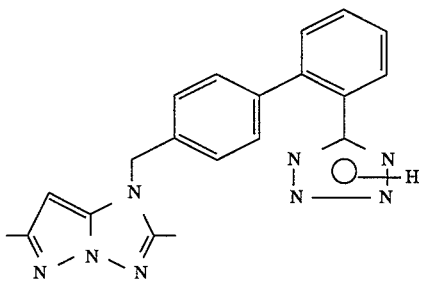

A 1.00 g portion of 2,6-dimethyl-1-[[2'-(N-triphenylmethyl-tetrazol-5-yl)biphenyl-4-yl]methyl]-1H-pyrazolo[1,5-b][1,2,4]triazole (compound 2b) was treated in the same manner as described in Example 12 to give 0.56 g of 2,6-dimethyl-1-[[2'-(tetrazol-5-yl)biphenyl-4-yl]methyl]-1H-pyrazolo[1,5-b][1,2,4]triazole in the form of colorless crystals.

(1) Melting point: 239°–241° C. (decomposition)

(2) Elemental analysis data (for C$_{20}$H$_{18}$N$_8$)

|  | C (%) | H (%) | N (%) |
|---|---|---|---|
| calculated: | 64.85 | 4.90 | 30.25 |
| found: | 64.79 | 4.95 | 29.97 |

(3) Nuclear magnetic resonance spectrum (DMSO-d$_6$, TMS) δ (ppm):
2.20 (3H, s), 2.45 (3H, s), 5.19 (2H, s), 5.27 (1H, S), 7.12 (2H, d), 7.27 (2H, d)

(4) Mass spectrometric data (FAB): 371 (MH$^+$)

Example 14

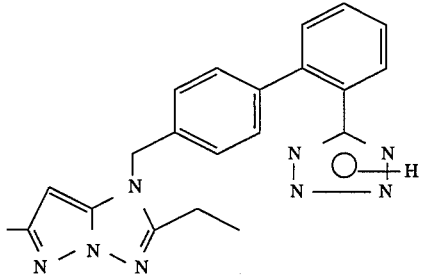

A 589 mg portion of 2-ethyl-6-methyl-1-[[2'-(N-triphenylmethyl-tetrazol-5-yl)biphenyl-4-yl]methyl]-1H-pyrazolo[1,5-b][1,2,4]triazole (compound 3b) was treated in the same manner as described in Example 12 to give 317 mg of 2-ethyl-6-methyl-1-[[2'-(tetrazol-5-yl)biphenyl-4-yl]methyl]-1H-pyrazolo[1,5-b][1,2,4]triazole in the form of colorless crystals.

(1) Melting point: 204°–206° C. (decomposition)

(2) Elemental analysis data (for C$_{21}$H$_{20}$N$_8$·0.2CH$_3$COOCH$_2$CH$_3$)

|  | C (%) | H (%) | N (%) |
|---|---|---|---|
| calculated: | 65.12 | 5.41 | 27.87 |
| found: | 65.23 | 5.33 | 27.93 |

(3) Nuclear magnetic resonance spectrum (DMSO-d$_6$, TMS) δ (ppm):
1.24 (3H, t), 2.20 (3H, s), 2.82 (2H, q), 5.20 (2H, s), 5.26 (1H, s), 7.11 (2H, d), 7.25 (2H, d)

(4) Mass spectrometric data (FAB): 385 (MH$^+$)

Example 15

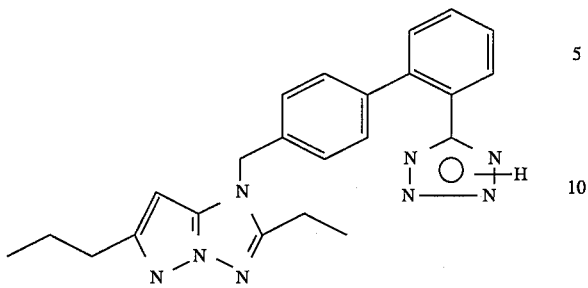

A 484 mg portion of 2-ethyl-6-propyl-1-[[2'-(N-triphenyl-methyl-tetrazol- 5-yl)biphenyl-4-yl]methyl]-1H-pyrazolo[1,5-b][1,2,4]triazole (compound 4b) was treated in the same manner as described in Example 12, and the resulting residue was subjected to silica gel column chromatography. Elution was conducted with a gradient from chloroform only to methanol-chloroform (3:17, v/v) to give 290 mg of 2-ethyl-6 -propyl-1-[[2'-(tetrazol-5-yl)biphenyl-4-yl]methyl]-1H-pyrazolo[ 1,5-b][1,2,4]triazole in the form of colorless amorphous foamy substance.

(1) Nuclear magnetic resonance spectrum (DMSO-$d_6$, TMS) δ (ppm):
  0.90 (3H, t), 1.24 (3H, t), 1.59 (2H, m), 2.82 (2H, q), 5.20 (2H, s), 5.32 (1H, s), 7.11 (2H, d), 7.24 (2H, d)

(2) Mass spectrometric data (FAB): 413 (MH$^+$)

Example 16

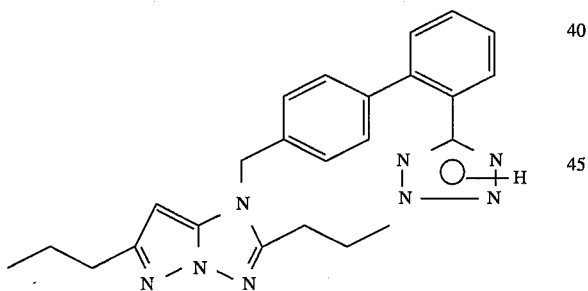

A 423 mg portion of 2,6-dipropyl-1-[[2'-(N-triphenylmethyl-tetrazol- 5-yl)biphenyl-4-yl]methyl]-1H-pyrazolo-[1,5-b][1,2,4]triazole (compound 5b) was treated in the same manner as described in Example 15 to give 154 mg of 2,6-dipropyl-1-[[2'-(tetrazol-5-yl)biphenyl-4-yl]methyl]-1H-pyrazolo[ 1,5-b][1,2,4]triazole in the form of colorless amorphous foamy substance.

(1) Nuclear magnetic resonance spectrum (DMSO-$d_6$, TMS) δ (ppm):
  0.90 (3H, t), 0.97 (3H, t), 1.59 (2H, m), 1.69 (2H, m), 2.78 (2H, t), 5.21 (2H, s), 5.33 (1H, s), 7.11 (2H, d), 7.22 (2H, d)

(2) Mass spectrometric data (FAB): 427 (MH$^+$)

Example 17

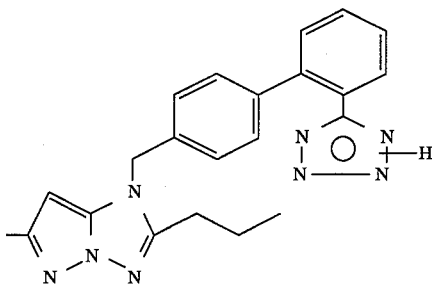

A 310 mg portion of 6-methyl-2-propyl-1-[[2'-(N-triphenylmethyl-tetrazol- 5-yl)biphenyl-4-yl]methyl]-1H-pyrazolo[ 1,5-b][1,2,4]triazole (compound 6b) was treated in the same manner as described in Example 12 to give 136 mg of 6-methyl-2-propyl-1-[[2'-(tetrazol-5-yl)biphenyl-4-yl]methyl]-1H-pyrazolo[1,5-b][1,2,4]triazole in the form of colorless crystals.

(1) Melting point: 156°–157° C.

(2) Elemental analysis data (for $C_{22}H_{22}N_8$)

|  | C (%) | H (%) | N (%) |
|---|---|---|---|
| calculated: | 66.31 | 5.56 | 28.12 |
| found: | 66.36 | 5.74 | 27.74 |

(3) Nuclear magnetic resonance spectrum (DMSO-$d_6$, TMS) δ (ppm):
  0.96 (3H, t), 1.68 (2H, m), 2.20 (3H, s), 2.78 (2H, t), 5.21 (2H, s), 5.26 (1H, s), 7.11 (2H, d), 7.24 (2H, d)

(4) Mass spectrometric data (FAB): 399 (MH$^+$)

Example 18

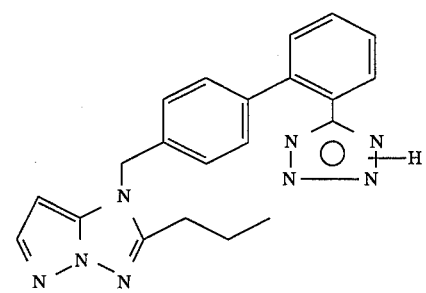

A 940 mg portion of 2-propyl-1-[[2'-(N-triphenylmethyl-tetrazol- 5-yl)biphenyl-4-yl]methyl]-1H-pyrazolo[ 1,5-b][1,2,4]triazole (compound 7b) was treated in the same manner as described in Example 12 to give 473 mg of 2-propyl-1-[[2'-(tetrazol-5-yl)biphenyl-4-yl]methyl]-1H-pyrazolo[ 1,5-b][1,2,4]triazole in the form of colorless crystals.

(1) Melting point: 103°–105° C.

(2) Elemental analysis data (for $C_{21}H_{20}N_8 \cdot 0.2CH_3COOCH_2CH_3$)

|  | C (%) | H (%) | N (%) |
|---|---|---|---|
| calculated: | 65.12 | 5.41 | 27.87 |
| found: | 65.27 | 5.41 | 28.06 |

(3) Nuclear magnetic resonance spectrum (DMSO-$d_6$, TMS) δ (ppm):

0.97 (3H, t), 1.70 (2H, m), 2.81 (2H, t), 5.26 (2H, s), 5.51 (1H, d), 7.11 (2H, d), 7.26 (2H, d), 7.38 (1H, d)

(4) Mass spectrometric data (FAB): 385 (MH$^+$)

Example 19

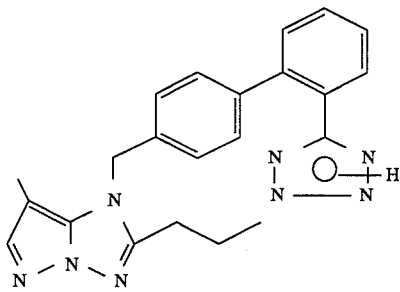

A 143 mg portion of 7-methyl-2-propyl-1-[[2'-(N-triphenylmethyl-tetrazol- 5-yl)biphenyl-4-yl]methyl]-1H-pyrazolo[ 1,5-b][1,2,4]triazole (compound 8a) was treated in the same manner as described in Example 12, and the resulting residue was crystallized from acetonitrile to give 63 mg of 7-methyl-2-propyl-1-[[2'-(tetrazol-5-yl)biphenyl-4-yl]methyl]-1H-pyrazolo[1,5-b][1,2,4]triazole in the form of colorless crystals.

(1) Melting point: 230°–231.5° C. (decomposition)

(2) Elemental analysis data (for $C_{22}H_{22}N_8$)

|  | C (%) | H (%) | N (%) |
|---|---|---|---|
| calculated: | 66.31 | 5.56 | 28.12 |
| found: | 66.28 | 5.64 | 28.18 |

(3) Nuclear magnetic resonance spectrum (DMSO-$d_6$, TMS) δ (ppm):

0.96 (3H, t), 1.68 (2H, m), 1.82 (3H, s), 2.78 (2H, t), 5.33 (2H, s), 7.10 (2H, d), 7.13 (2H, d), 7.18 (1H, s)

(4) Mass spectrometric data (FAB): 399 (MH$^+$)

Example 20

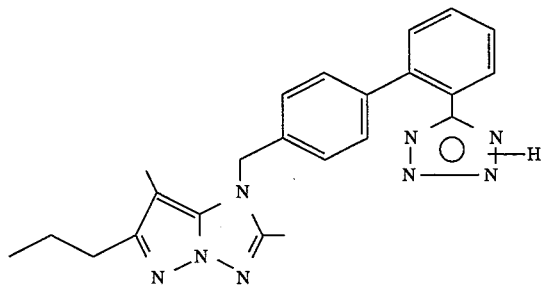

A 940 mg portion of 2,7-dimethyl-6-propyl-1-[[2' -(N-triphenylmethyl-tetrazol-5-yl)biphenyl-4-yl]methyl]-1H-pyrazolo[ 1,5-b][1,2,4]triazole (compound 9a) was treated in the same manner as described in Example 12 to give 512 mg of 2,7-dimethyl-6-propyl-1-[[2'-(tetrazol-5-yl)biphenyl-4-yl] methyl]-1H-pyrazolo[1,5-b][1,2,4]triazole in the form of colorless crystals.

(1) Melting point: 231°–232° C. (decomposition)

(2) Elemental analysis data (for $C_{23}H_{24}N_8$)

|  | C (%) | H (%) | N (%) |
|---|---|---|---|
| calculated: | 66.97 | 5.86 | 27.16 |
| found: | 66.91 | 5.90 | 27.06 |

(3) Nuclear magnetic resonance spectrum (DMSO-$d_6$, TMS) δ (ppm):

0.95 (3H, t), 1.64 (2H, m), 1.93 (3H, s), 2.43 (3H, s), 2.55 (2H, t), 5.21 (2H, s), 7.12 (2H, d), 7.15 (2H, d)

(4) Mass spectrometric data (FAB): 413 (MH$^+$)

Example 21

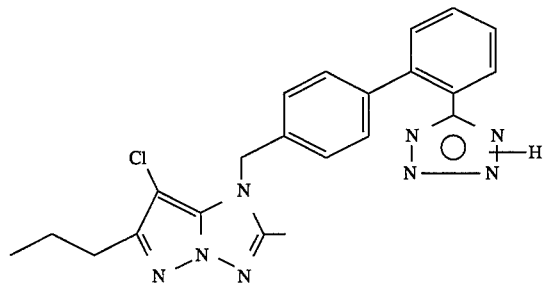

A 560 mg portion of 7-chloro-2-methyl-6-propyl-1 -[[2'-(N-triphenylmethyl-tetrazol-5-yl)biphenyl-4-yl]methyl] -1H-pyrazolo[1,5-b][1,2,4]triazole (compound 10a) was treated in the same manner as described in Example 15 to give 300 mg of 7-chloro-2-methyl-6-propyl-1-[[2'-(tetrazol-5-yl)biphenyl- 4-yl]methyl]-1H-pyrazolo[1,5-b][1,2,4]triazole in the form of colorless amorphous foamy substance.

(1) Nuclear magnetic resonance spectrum (DMSO-d$_6$, TMS) δ (ppm):
0.92 (3H, t), 1.63 (2H, m), 2.44 (3H, s), 2.54 (2H, t), 5.30 (2H, s), 7.12 (2H, d), 7.21 (2H, d)

(2) Mass spectrometric data (FAB): 433 (MH$^+$)

Example 22

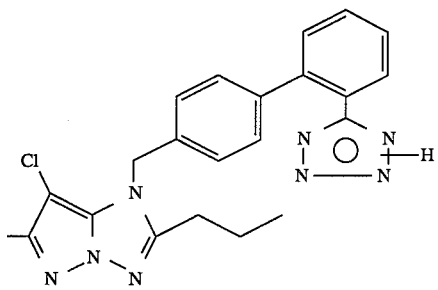

A 420 mg portion of 7-chloro-6-methyl-2-propyl-1 -[[2'-(N-triphenylmethyl-tetrazol-5-yl)biphenyl-4-yl]methyl] -1H-pyrazolo[1,5-b][1,2,4]triazole (compound 11a) was treated in the same manner as described in Example 19 to give 218 mg of 7-chloro-6-methyl-2-propyl-1-[[2'-(tetrazol-5-yl)biphenyl-4-yl]methyl]-1H-pyrazolo[1,5-b][1,2,4]triazole in the form of colorless crystals.

(1) Melting point: 213°–214.5° C.

(2) Elemental analysis data (for C$_{22}$H$_{21}$ClN$_8$)

|  | C (%) | H (%) | N (%) | Cl (%) |
|---|---|---|---|---|
| calculated: | 61.04 | 4.89 | 25.88 | 8.19 |
| found: | 60.92 | 5.03 | 25.97 | 8.24 |

(3) Nuclear magnetic resonance spectrum (DMSO-d$_6$, TMS) δ (ppm):
0.93 (3H, t), 1.63 ( 2H, m), 2.20 ( 3H, s ), 2.75 (2H, t), 5.32 (2H, s), 7.11 (2H, d), 7.19 (2H, d)

(4) Mass spectrometric data (FAB): 433 (MH$^+$)

Example 23

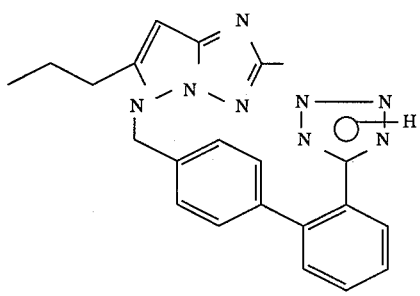

A 1.66 g portion of the mixed product obtained in Example 1 consisting (about 3:1) of 2-methyl-6-propyl-5-[ [2' -(N-triphenylmethyl-tetrazol-5-yl)biphenyl-4-yl]methyl] -5 H-pyrazolo[1,5-b][1,2,4]triazole (compound 1d) and 2-methyl-6 -propyl-1H-pyrazolo[1,5-b][1,2,4]triazole was treated in the same manner as described in Example 12, the resulting residue was subjected to silica gel column chromatography. Elution was conducted with a gradient from chloroform only to methanol-chloroform (3:17, v/v) and then the eluted product was crystallized from ethyl acetate to give 0.44 g of 2-methyl-6-propyl-5-[[2'-(tetrazol-5-yl)biphenyl-4 -yl]methyl]-5H-pyrazolo[1,5-b][1,2,4]triazole in the form of colorless crystals.

(1) Melting point: 169.5°–171° C.

(2) Elemental analysis data (for C$_{22}$H$_{22}$N$_8$·0.1CH$_3$COOCH$_2$CH$_3$)

|  | C (%) | H (%) | N (%) |
|---|---|---|---|
| calculated: | 66.06 | 5.64 | 27.51 |
| found: | 66.08 | 5.53 | 27.74 |

(3) Nuclear magnetic resonance spectrum (DMSO-d$_6$, TMS) δ (ppm):
0.93 (3H, t), 1.61 (2H, m), 2.28 (3H, s), 2.69 (2H, t), 5.48 (2H, s), 6.06 (1H, s), 7.06 (4H, s)

(4) Mass spectrometric data (FAB): 399 (MH$^+$)

Example 24

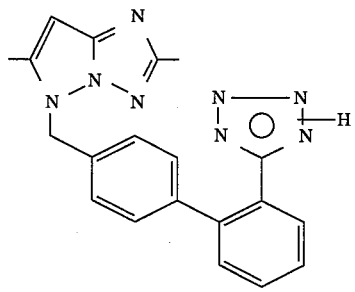

A 1.00 g portion of 2,6-dimethyl-5-[[2'-(N-triphenylmethyl-tetrazol- 5-yl)biphenyl-4-yl]methyl]-5H-pyrazolo[ 1,5-b][1,2,4]triazole (compound 2d) was treated in the same manner as described in Example 12 to give 0.59 g of 2,6-dimethyl-5-[[2'-(tetrazol-5-yl)biphenyl-4-yl]methyl]-5H-pyrazolo[ 1,5-b][1,2,4]triazole in the form of colorless crystals.

(1) Melting point: 225°–228° C.

(2) Elemental analysis data (for C$_{20}$H$_{18}$N$_8$·0.1CH$_3$COOCH$_2$CH$_3$)

|  | C (%) | H (%) | N (%) |
|---|---|---|---|
| calculated: | 64.61 | 5.00 | 29.55 |
| found: | 64.39 | 5.02 | 29.41 |

(3) Nuclear magnetic resonance spectrum (DMSO-d$_6$, TMS) δ (ppm):
2.27 (3H, s), 2.39 (3H, s), 5.47 (2H, s), 6.04 (1H, s), 7.07 (2H, d), 7.10 (2H, d)

(4) Mass spectrometric data (FAB): 371 (MH$^+$)

Example 25

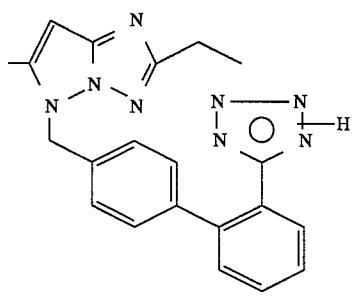

A 610 mg portion of 2-ethyl-6-methyl-5-[[2'-(N-triphenylmethyl-tetrazol- 5-yl)biphenyl-4-yl]methyl]-5H-pyrazolo[ 1,5-b][1,2,4]triazole (compound 3d) was treated in the same manner as described in Example 12 to give 316 mg of 2-ethyl-6-methyl-5-[[2'-(tetrazol-5-yl)biphenyl-4-yl]methyl] -5H-pyrazolo[1,5-b][1,2,4]triazole in the form of colorless crystals.

(1) Melting point: 206°–207.5° C. (decomposition)

(2) Elemental analysis data (for $C_{21}H_{20}N_8$)

|  | C (%) | H (%) | N (%) |
|---|---|---|---|
| calculated: | 65.61 | 5.24 | 29.15 |
| found: | 65.41 | 5.18 | 28.85 |

(3) Nuclear magnetic resonance spectrum (DMSO-$d_6$, TMS) δ (ppm):
1.21 (3H, t), 2.38 (3H, s), 2.63 (2H, q), 5.47 (2H, s), 6.03 (1H, s), 7.06 (2H, d), 7.10 (2H, d)

(4) Mass spectrometric data (FAB): 385 (MH$^+$)

Example 26

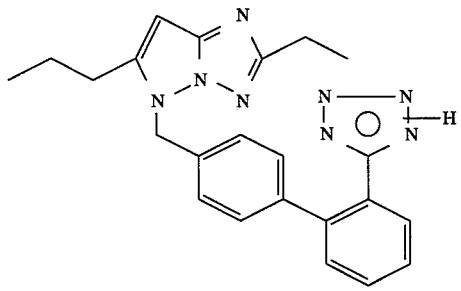

A 417 mg portion of 2-ethyl-6-propyl-5-[[2'-(N-triphenylmethyl-tetrazol- 5-yl)biphenyl-4-yl]methyl]-5H-pyrazolo[ 1,5-b][1,2,4]triazole (compound 4c) was treated in the same manner as described in Example 12 to give 180 mg of 2-ethyl-6-propyl-5-[[2'-(tetrazol-5-yl)biphenyl-4-yl]methyl] -5H-pyrazolo[1,5-b][1,2,4]triazole in the form of colorless crystals.

(1) Melting point: 172°–173.5° C.

(2) Elemental analysis data (for $C_{23}H_{24}N_8$)

|  | C (%) | H (%) | N (%) |
|---|---|---|---|
| calculated: | 66.97 | 5.86 | 27.16 |
| found: | 66.80 | 5.87 | 27.12 |

(3) Nuclear magnetic resonance spectrum (DMSO-$d_6$, TMS) δ (ppm):
0.93 (3H, t), 1.21 (3H, t), 1.61 (2H, m), 2.60–2.70 (4H, m), 5.48 (2H, s), 6.06 (1H, s), 7.06 (4H, d)

(4) Mass spectrometric data (FAB): 413 (MH$^+$)

Example 27

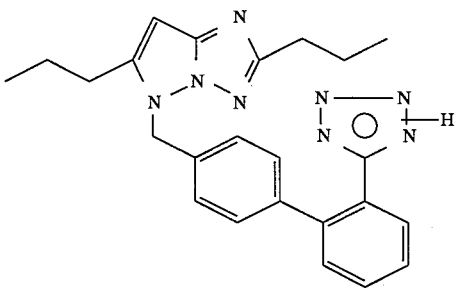

A 347 mg portion of 2,6-dipropyl-5-[[2'-(N-triphenylmethyl-tetrazol- 5-yl)biphenyl-4-yl]methyl]-5H-pyrazolo[ 1,5-b][1,2,4]triazole (compound 5c) was treated in the same manner as described in Example 12 to give 187 mg of 2,6-dipropyl-5-[[2'-(tetrazol-5-yl)biphenyl-4-yl]methyl]-5H-pyrazolo[ 1,5-b][1,2,4]triazole in the form of colorless crystals.

(1) Melting point: 172°–174° C.

(2) Elemental analysis data (for $C_{24}H_{26}N_8$)

|  | C (%) | H (%) | N (%) |
|---|---|---|---|
| calculated: | 67.58 | 6.14 | 26.27 |
| found: | 67.52 | 6.30 | 26.21 |

(3) Nuclear magnetic resonance spectrum (DMSO-$d_6$, TMS) δ (ppm):
0.88–0.95 (6H, m), 1.58–1.70 (4H, m), 2.58 (2H, t), 2.68 (2H, t), 5.48 (2H, s), 6.06 (1H, s), 7.06 (4H, s)

(4) Mass spectrometric data (FAB): 427 (MH$^+$)

Example 28

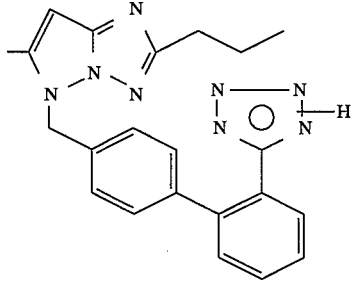

A 359 mg portion of the mixed product obtained in Example 6 consisting (about 2:1) of 6-methyl-2-propyl-5-[[2'-(N-triphenylmethyl-tetrazol-5-yl)biphenyl-4-yl]methyl]-5H-pyrazolo[1,5-b][1,2,4]triazole (compound 6c) and 6-methyl-2-propyl-1H-pyrazolo[1,5-b][1,2,4]triazole was treated in the same manner as described in Example 23 to give 126 mg of 6-methyl-2-propyl-5-[[2'-(tetrazol-5-yl)biphenyl-4-yl] methyl]-5H-pyrazolo[1,5-b][1,2,4]triazole in the form of colorless crystals.

(1) Melting point: 175°–177.5° C.

(2) Elemental analysis data (for $C_{22}H_{22}N_8 \cdot 0.6H_2O$)

|  | C (%) | H (%) | N (%) |
| --- | --- | --- | --- |
| calculated: | 64.56 | 5.71 | 27.38 |
| found: | 64.48 | 5.61 | 27.38 |

(3) Nuclear magnetic resonance spectrum (DMSO-$d_6$, TMS) δ (ppm):

0.90 (3H, t), 1.67 (2H, m), 2.38 (3H, s), 2.58 (2H, t), 5.46 (2H, s), 6.02 (1H, s), 7.06 (2H, d), 7.09 (2H, d)

(4) Mass spectrometric data (FAB): 399 (MH⁺)

Example 29

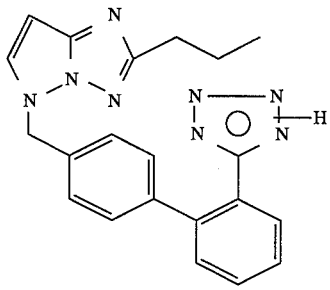

A 568 mg portion of 2-propyl-5-[[2'-(N-triphenylmethyl-tetrazol-5-yl)biphenyl-4-yl]methyl]-5H-pyrazolo[1,5-b][1,2,4]triazole (compound 7b) was treated in the same manner as described in Example 12 to give 165 mg of 2-propyl-5-[[2'-(tetrazol-5-yl)biphenyl-4-yl]methyl]-5H-pyrazolo[1,5-b][1,2,4]triazole in the form of colorless crystals.

(1) Melting point: 109°–111° C.

(2) Elemental analysis data (for $C_{21}H_{20}N_8 \cdot 0.2H_2O$)

|  | C (%) | H (%) | N (%) |
| --- | --- | --- | --- |
| calculated: | 65.00 | 5.30 | 28.88 |
| found: | 65.07 | 5.14 | 28.81 |

(3) Nuclear magnetic resonance spectrum (DMSO-$d_6$, TMS) δ (ppm):

0.90 (3H, t), 1.67 (2H, m), 2.59 (2H, t), 5.46 (2H, s), 6.20 (1H, d), 7.07 (2H, d), 7.20 (2H, d), 7.92 (1H, d)

(4) Mass spectrometric data (FAB): 385 (MH⁺)

Example 30

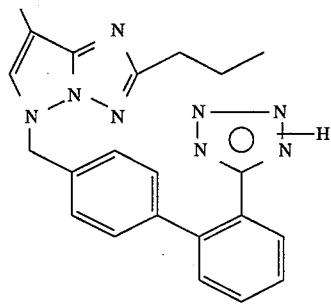

A 783 mg portion of 7-methyl-2-propyl-5-[[2'-(N-triphenylmethyl-tetrazol-5-yl)biphenyl-4-yl]methyl]-5H-pyrazolo[1,5-b][1,2,4]triazole (compound 8b) was treated in the same manner as described in Example 19 to give 412 mg of 7-methyl-2-propyl-5-[[2'-(tetrazol-5-yl)biphenyl-4-yl] methyl]-5H-pyrazolo[1,5-b][1,2,4]triazole in the form of colorless crystals.

(1) Melting point: 193°–196° C. (decomposition)

(2) Elemental analysis data (for $C_{22}H_{22}N_8$)

|  | C (%) | H (%) | N (%) |
| --- | --- | --- | --- |
| calculated: | 66.31 | 5.56 | 28.12 |
| found: | 66.13 | 5.57 | 28.04 |

(3) Nuclear magnetic resonance spectrum (DMSO-$d_6$, TMS) δ (ppm):

0.90 (3H, t), 1.67 (2H, m), 2.09 (3H, s), 2.58 (2H, t), 5.35 (2H, s), 7.05 (2H, d), 7.18 (2H, d)

(4) Mass spectrometric data (FAB): 399 (MH⁺)

Example 31

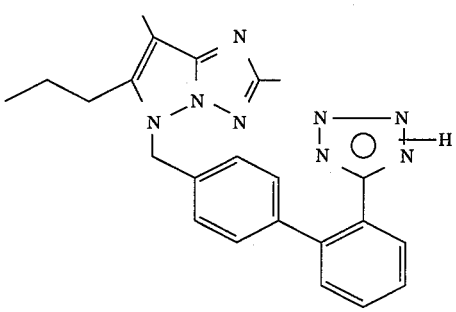

A 2.45 g portion of 2,7-dimethyl-6-propyl-5-[[2'-(N-triphenylmethyl-tetrazol-5-yl)biphenyl-4-yl]methyl]-5H-pyrazolo[1,5-b][1,2,4]triazole (compound 9b) was treated in the same manner as described in Example 12 to give 1.45 g of 2,7-dimethyl-6-propyl-5-[[2'-(tetrazol-5-yl)biphenyl-4-yl] methyl]-5H-pyrazolo[1,5-b][1,2,4]triazole in the form of colorless crystals.

(1) Melting point: 198°–200° C. (decomposition)

(2) Elemental analysis data (for $C_{22}H_{24}N_8 \cdot 0.1CH_3COOCH_2CH_3$)

|  | C (%) | H (%) | N (%) |
|---|---|---|---|
| calculated: | 66.71 | 5.93 | 26.60 |
| found: | 66.95 | 5.98 | 26.34 |

(3) Nuclear magnetic resonance spectrum (DMSO-$d_6$, TMS) δ (ppm):
0.88 (3H, t), 1.47 (2H, m), 2.06 (3H, s), 2.27 (3H, s), 2.69 (2H, t), 5.41 (2H, s), 7.02 (2H, d), 7.05 (2H, d)

(4) Mass spectrometric data (FAB): 413 (MH$^+$)

Example 32

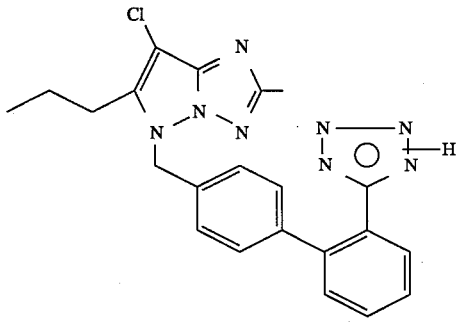

A 198 mg portion of 7-chloro-2-methyl-6-propyl-5 -[[2'-(N-triphenylmethyl-tetrazol-5-yl)biphenyl-4-yl]methyl]-5H-pyrazolo[1,5-b][1,2,4]triazole (compound 10b) was treated in the same manner as described in Example 12 to give 81 mg of 7-chloro-2-methyl-6-propyl-5-[[2'-(tetrazol-5-yl)biphenyl- 4-yl]methyl]-5H-pyrazolo[1,5-b][1,2,4]triazole in the form of colorless crystals.

(1) Melting point: 185°–187.5° C. (decomposition)

(2) Elemental analysis data (for $C_{22}H_{21}ClN_8$)

|  | C (%) | H (%) | N (%) | Cl (%) |
|---|---|---|---|---|
| calculated: | 61.04 | 4.89 | 25.88 | 8.19 |
| found: | 61.09 | 4.92 | 25.88 | 8.34 |

(3) Nuclear magnetic resonance spectrum (DMSO-$d_6$, TMS) δ (ppm):
0.90 (3H, t), 1.52 (2H, m), 2.30 (3H, s), 2.79 (2H, t), 5.54 (2H, s), 7.07 (2H, d), 7.10 (2H, d)

(4) Mass spectrometric data (FAB): 433 (MH$^+$)

Example 33

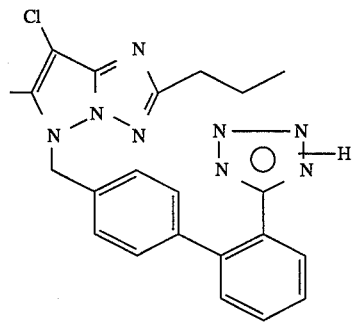

A 740 mg portion of 7-chloro-6-methyl-2-propyl-5 -[[2'-(N-triphenylmethyl-tetrazol-5-yl)biphenyl-4-yl]methyl]-5H-pyrazolo[1,5-b][1,2,4]triazole (compound 11b) was treated in the same manner as described in Example 12 to give 414 mg of 7-chloro-6-methyl-2-propyl-5-[[2'-(tetrazol-5-yl)biphenyl-4-yl]methyl]-5H-pyrazolo[1,5-b][1,2,4]triazole in the form of colorless crystals.

(1) Melting point: 120°–122° C.

(2) Elemental analysis data (for $C_{22}H_{21}N_8 \cdot 0.4CH_3COOCH_2CH_3$)

|  | C (%) | H (%) | N (%) | Cl (%) |
|---|---|---|---|---|
| calculated: | 60.55 | 5.21 | 23.94 | 7.57 |
| found: | 60.53 | 5.24 | 23.60 | 7.55 |

(3) Nuclear magnetic resonance spectrum (DMSO-$d_6$, TMS) δ (ppm):
0.90 (3H, t), 1.68 (2H, m), 2.41 (3H, s), 2.61 (2H, t), 5.52 (2H, s), 7.07 (2H, d), 7.15 (2H, d)

(4) Mass spectrometric data (FAB): 433 (MH$^+$)

Example 34

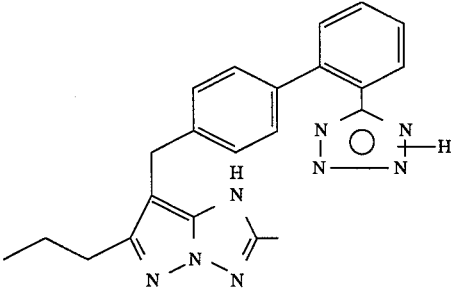

A 183 mg portion of 2-methyl-6-propyl-7-[[2'-(N-triphenylmethyl-tetrazol- 5-yl)biphenyl-4-yl]methyl]-1H-pyrazolo[ 1,5-b][1,2,4]triazole (compound 1c) was treated in the same manner as described in Example 12, the resulting residue was dissolved in ethyl acetate with heating and then the solution was cooled to collect the thus formed precipitate by filtration, thereby giving 85 mg of 2-methyl- 6-propyl-7-[[2'-(tetrazol-5-yl)biphenyl-4-yl]methyl]-1 H-pyrazolo[1,5-b][1,2,4]triazole in the form of colorless amorphous solid.

(1) Elemental analysis data (for $C_{22}H_{22}N_8 \cdot 0.5CH_3COOCH_2CH_3$)

|  | C (%) | H (%) | N (%) |
|---|---|---|---|
| calculated: | 65.14 | 5.92 | 25.32 |
| found: | 65.07 | 5.80 | 25.56 |

(2) Nuclear magnetic resonance spectrum (DMSO-$d_6$, TMS) δ (ppm):

0.87 (3H, t), 1.53 (2H, m), 2.36 (3H, s), 3.78 (2H, s), 6.99 (2H, d), 7.12 (2H, d), 12.20 (1H, s)

(3) Mass spectrometric data (FAB): 399 (MH$^+$)

Example 35

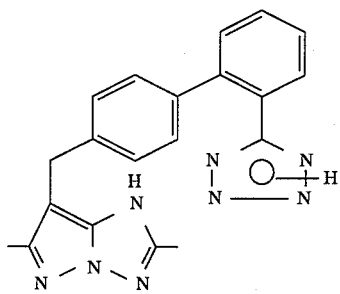

A 226 mg portion of 2,6-dimethyl-7-[[2'-(N-triphenylmethyl-tetrazol- 5-yl)biphenyl-4-yl]methyl]-1H-pyrazolo[1,5-b][1,2,4]triazole (compound 2c) was treated in the same manner as described in Example 34 to give 105 mg of 2,6-dimethyl-7-[[2'-(tetrazol-5-yl)biphenyl-4-yl]methyl]-1H-pyrazolo[ 1,5-b][1,2,4]triazole in the form of colorless amorphous solid.

(1) Elemental analysis data (for $C_{22}H_{18}N_8 \cdot 0.4CH_3COOCH_2CH_3$)

|  | C (%) | H (%) | N (%) |
|---|---|---|---|
| calculated: | 63.95 | 5.27 | 27.62 |
| found: | 63.63 | 5.16 | 27.77 |

(2) Nuclear magnetic resonance spectrum (DMSO-$d_6$, TMS) δ (ppm):

2.15 (3H, s), 2.36 (3H, s), 3.77 (2H, s), 6.99 (2H, d), 7.12 (2H, d), 12.22 (1H, s)

(3) Mass spectrometric data (FAB): 371 (MH$^+$)

Example 36

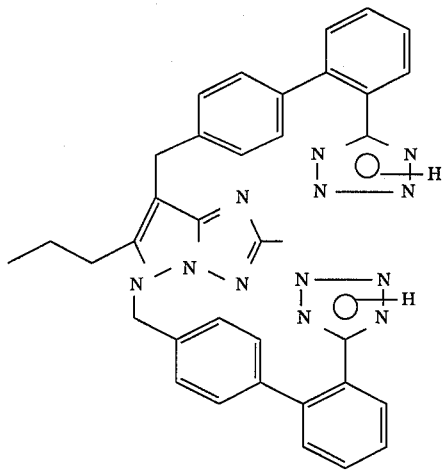

A 342 mg portion of 5,7-bis[[2'-(N-triphenylmethyl-tetrazol- 5-yl)biphenyl-4-yl]methyl]-2-methyl-6-propyl-5H-pyrazolo[ 1,5-b][1,2,4]triazole (compound 1a) was treated in the same manner as described in Example 12, the resulting residue was mixed with toluene and heated under reflux and then the solution was cooled spontaneously to collect the thus formed precipitate by filtration, thereby giving 182 mg of 5,7-bis[[2'-(tetrazol-5-yl)biphenyl-4-yl]methyl]-2-methyl- 6-propyl-5H-pyrazolo[1,5-b][1,2,4]triazole in the form of colorless amorphous solid.

(1) Nuclear magnetic resonance spectrum (DMSO-$d_6$, TMS) δ (ppm):

0.86 (3H, t), 1.40 (2H, m), 2.27 (3H, s), 2.74 (2H, t), 3.87 (2H, s), 5.45 (2H, s)

(2) Mass spectrometric data (FAB): 632 (M$^+$)

Example 37

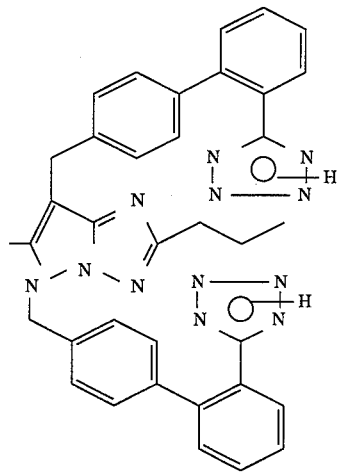

A 153 mg portion of 5,7-bis[[2'-(N-triphenylmethyl-tetrazol- 5-yl)biphenyl-4-yl]methyl]-6-methyl-2-propyl-5H-pyrazolo[ 1,5-b][1,2,4]triazole (compound 6a) was treated in the same manner as described in Example 36 to give 69 mg of 5,7-bis[[2'-(tetrazol-5-yl)biphenyl-4-yl]methyl]-6-methyl-2-propyl-5H-pyrazolo[1,5-b][1,2,4]triazole in the form of light yellow amorphous solid.

(1) Nuclear magnetic resonance spectrum (DMSO-$d_6$, TMS) $\delta$ (ppm):
0.90 (3H, t), 1.66 (2H, m), 2.37 (3H, s), 2.57 (2H, t), 3.85 (2H, s), 5.44 (2H, s)

(2) Mass spectrometric data (FAB): 633 (MH$^+$)

Reference Example 11 (Starting compound for use in Example 38)

(A) With cooling at −78° C., ammonia gas was blown into a three neck flask to yield 600 ml of liquid ammonia. At −78° C., 19.0 g of sodium amide was added to the flask and stirred for 10 minutes at the same temperature, followed by gradual addition of 40 ml of n-butyronitrile in a dropwise manner and subsequent 10 minutes of stirring at −78° C. A 40 ml portion of ethyl formate was gradually added in a dropwise manner to the above reaction solution and the mixture was stirred for 1 hour at −78° C. With stirring, the reaction solution was warmed on a 40° C. water bath to distill off ammonia. The resulting residue was added to 150 ml of ice water and adjusted to a pH value of less than 1 with 6N hydrochloric acid. After extracting twice with 30 ml of ethyl ether, the resulting ether layers were combined and mixed with 100 ml of ethanol. A 23 ml portion of hydrazine monohydrate was added to the resulting solution at room temperature, and the mixture was heated at 80° C. to distill off ethyl ether and then subjected to over night reflux with heating. After distilling off the solvent under a reduced pressure, the resulting residue was subjected to silica gel column chromatography. Elution with 1:20 methanol-chloroform gave 12.8 g of 3-amino-4-ethyl-1H-pyrazole.

(1) Nuclear magnetic resonance spectrum (CDCl$_3$, TMS) $\delta$ (ppm):
1.16 (3H, t), 2.31 (2H, q), 7.10 (1H, s)

(2) Mass spectrometric data (EI): 111 (M$^+$)

(B) A 7.9 g portion of triethyl orthopropionate was added to 5.0 g of 3-amino-4-ethyl-1H-pyrazole and the mixture was heated at 120° C. to distill off the thus formed ethanol. After 3 hours of the reaction, the reaction solution was cooled down to room temperature and mixed with 30 ml of methanol, 3.2 g of hydroxylamine hydrochloride and 4.6 g of triethylamine in that order, followed by 3 hours of heating under reflux. After distilling off the solvent under a reduced pressure, the resulting residue was mixed with 150 ml of ethyl acetate and washed twice with water, and the ethyl acetate layer was dried over anhydrous magnesium sulfate and concentrated under a reduced pressure. Thereafter, the thus obtained residue was subjected to silica gel column chromatography. Elution with methanol-chloroform (1:20, v/v) gave 3.9 g of N-(4-ethyl-1H-pyrazol-3-yl)propionamidoxime.

(1) Nuclear magnetic resonance spectrum (CDCl$_3$, TMS) $\delta$ (ppm):
1.02 (3H, t), 1.18 (3H, t), 2.39 (2H, q), 2.41 (2H, q), 7.32 (1H, s)

(2) Mass spectrometric data (EI): 182 (M$^+$)

(C) A 3.9 g portion of N-(4-ethyl-1H-pyrazol-3-yl)propionamidoxime was dissolved in 20 ml of N,N-dimethylacetamide. With cooling on an ice bath, to this were added 2.2 ml of pyridine and 4.1 g of p-toluenesulfonic acid chloride, followed by 30 minutes of stirring at the same temperature and additional 3 hours of stirring at room temperature. The resulting reaction mixture was added to 100 ml of water and extracted with chloroform. After distilling off chloroform from the organic layer under a reduced pressure, the thus obtained residue was dissolved in 100 ml of methanol, mixed with 2.2 ml of pyridine and then heated under reflux for 2 hours.

After distilling off the solvent under a reduced pressure, the resulting residue was mixed with 100 ml of ethyl acetate and washed with water. Thereafter, the organic layer was dried over anhydrous magnesium sulfate and concentrated under a reduced pressure, and the resulting residue was subjected to silica gel column chromatography. By carrying out elution with methanol-chloroform (1:20, v/v), 1.60 g of 2,7-diethyl-1H-pyrazolo[1,5-b][1,2,4]triazole was obtained in the form of light yellow crystals.

(1) Nuclear magnetic resonance spectrum (DMSO-$d_6$, TMS) $\delta$ (ppm):
1.19 (3H, t), 1.28 (3H, t), 2.50 (2H, q), 2.74 (2H, q), 7.21 (1H, s)

(2) Mass spectrometric data (EI): 164 (M$^+$)

Reference Example 12 ( Starting compound for use in Example 39)

(A) In the same manner as described in the step (B) of Reference Example 11, 730 mg of N-(4-ethyl-1H-pyrazol-3-yl)acetamidoxime was obtained from 3.0 g of 3-amino-4-methyl-1H-pyrazole and 4.4 g of triethyl orthoacetate.

(1) Nuclear magnetic resonance spectrum (DMSO-$d_6$, TMS) $\delta$ (ppm):
1.09 (3H, t), 1.71 (3H, s), 2.31 (2H, q), 7.41 (1H, s)

(2) Mass spectrometric data (EI): 168 (M$^+$)

(B) In the same manner as the procedure of the step (C) of Reference Example 11, 580 mg of 7-ethyl-2-methyl-1H-pyrazolo[1,5-b][1,2,4]triazole was obtained from 2.8 g of N-(4-ethyl-1H-pyrazol-3-yl)acetamidoxime.

(1) Nuclear magnetic resonance spectrum (DMSO-$d_6$, TMS) $\delta$ (ppm):
1.19 (3H, t), 2.45 (3H, s), 2.50 (2H, q), 7.19 (1H, s)

(2) Mass spectrometric data (EI): 150 (M$^+$)

Reference Example 13 (Starting compound for use in Example 40)

(A) In the same manner as described in the step (A) of Reference Example 11, 17.2 g of 3-amino-4-n-propyl-1H-pyrazole was obtained from 40 ml of n-valeronitrile.

(1) Nuclear magnetic resonance spectrum (CDCl$_3$, TMS) $\delta$ (ppm):
0.93 (3H, t), 1.37 (2H, m), 2.34 (2H, t), 7.09 (1H, s)

(2) Mass spectrometric data (EI): 125 (M$^+$)

(B) In the same manner as described in the step (B) of Reference Example 11, 5.0 g of N-(4-n-propyl-1H-pyrazol-3-yl)propionamidoxime was obtained from 9.0 g of 3-amino-4-n-propyl-1H-pyrazole and 13 g of triethyl orthopropionate.

(1) Nuclear magnetic resonance spectrum (CDCl$_3$, TMS) $\delta$ (ppm):
0.93 (3H, t), 1.00 (3H, t), 1.36–1.76 (2H, m), 2.21–2.50 (4H, m), 7.31 (1H, s)

(2) Mass spectrometric data (EI): 182 (M$^+$)

(C) In the same manner as the procedure of the step (C) of Reference Example 11, 1.9 g of 2-ethyl-7-n-propyl-1H-pyrazolo[1,5-b][1,2,4]triazole was obtained from 5.0 g of N-(4-n-propyl-1H-pyrazol-3-yl)propionamidoxime.

(1) Nuclear magnetic resonance spectrum (DMSO-$d_6$, TMS) $\delta$ (ppm):
0.90 (3H, t), 1.28 (3H, t), 1.37–1.80 (2H, m) 2.46 (2H, t), 2.75 (2H, q), 7.20 (1H, s)

(2) Mass spectrometric data (EI): 178 ($M^+$)

Reference Example 14 (Starting compound for use in Example 41)

(A) In the same manner as described in the step (B) of Reference Example 11, 4.5 g of N-(4-n-propyl-1 H-pyrazol-3-yl)acetamidoxime was obtained from 7.2 g of 3-amino-4-n-propyl-1H-pyrazole and 9.3 g of triethyl orthoacetate.

(1) Nuclear magnetic resonance spectrum (CDCl$_3$, TMS) $\delta$ (ppm):
0.88 (3H, t), 1.49 (2H, m), 1.71 (3H, s), 2.28 (2H, t), 7.40 (1H, s)

(2) Mass spectrometric data (EI): 182 ($M^+$)

(B) In the same manner as the procedure of the step (C) of Reference Example 11, 1.5 g of 2-methyl-7-n-propyl-1H-pyrazolo[1,5-b][1,2,4]triazole was obtained from 4.5 g of N-(4-n-propyl-1H-pyrazol-3-yl)acetamidoxime.

(1) Nuclear magnetic resonance spectrum (DMSO-$d_6$, TMS) $\delta$ (ppm):
0.90 (3H, t), 1.59 (2H, m), 2.45 (2H, t), 2.93 (3H, s), 7.20 (2H, s)

(2) Mass spectrometric data (EI): 164 ($M^+$)

Reference Example 15 (Starting compound for use in Example 42)

(A) In the same manner as described in the step (A) of Reference Example 11, 10.1 g of 3-amino-4-n-butyl-1H-pyrazole was obtained from 50 ml of n-capronitrile.

(1) Nuclear magnetic resonance spectrum (CDCl$_3$, TMS) $\delta$ (ppm):
0.92 (3H, t), 1.17–1.67 (4H, m), 2.30 (2H, t), 7.10 (1H, s)

(2) Mass spectrometric data (EI): 139 ($M^+$)

(B) In the same manner as described in the step (B) of Reference Example 11, 3.5 g of N-(4-n-butyl-1H-pyrazol-3-yl) propionamidoxime was obtained from 6.2 g of 3-amino-4-n-butyl-1H-pyrazole and 7.8 g of triethyl orthopropionate.

(1) Nuclear magnetic resonance spectrum (CDCl$_3$, TMS) $\delta$ (ppm):
0.88 (6H, t), 1.24–1.56 (4H, m), 2.08–2.38 (4H, m), 7.39 (1H, s)

(2) Mass spectrometric data (EI): 210 ($M^+$)

(C) In the same manner as the procedure of the step (C) of Reference Example 11, 500 mg of 7-n-butyl-2-ethyl-1H-pyrazolo[1,5-b][1,2,4]triazole was obtained from 3.5 g of N-(4-n-butyl-1H-pyrazol-3-yl)propionamidoxime.

(1) Nuclear magnetic resonance spectrum (DMSO-$d_6$, TMS) $\delta$ (ppm):
0.90 (3H, t), 1.28 (3H, t), 1.19–1.65 (4H, m), 2.47 (2H, t), 2.74 (2H, q), 7.19 (2H, s)

(2) Mass spectrometric data (EI): 192 ($M^+$)

Reference Example 16 (Starting compound for use in Example 43)

(A) In the same manner as described in the step (A) of Reference Example 11, 10.1 g of 3-amino-4-isopropyl-1H-pyrazole was obtained from 42 ml of isobutyronitrile.

(1) Nuclear magnetic resonance spectrum (CDCl$_3$, TMS) $\delta$ (ppm):
1.18 (6H, d), 2.68 (1H, m), 7.10 (1H, s)

(2) Mass spectrometric data (EI): 125 ($M^+$)

(B) In the same manner as described in the step (B) of Reference Example 11, 3.6 g of N-(4-isopropyl-1H-pyrazol-3-yl)propionamidoxime was obtained from 5 g of 3-amino-4-isopropyl-1H-pyrazole and 7.0 g of triethyl orthopropionate.

(1) Nuclear magnetic resonance spectrum (CDCl$_3$, TMS) $\delta$ (ppm):
1.03 (3H, t), 1.20 (6H, d), 2.41 (2H, q), 2.81 (1H, m), 7.30 (1H, s)

(2) Mass spectrometric data (EI): 196 ($M^+$)

(C) In the same manner as the procedure of the step (C) of Reference Example 11, 1.6 g of 2-ethyl-7-isopropyl-1H-pyrazolo[1,5-b][1,2,4]triazole was obtained from 3.6 g of N-(4-isopropyl-1H-pyrazol-3-yl)propionamidoxime.

(1) Nuclear magnetic resonance spectrum (DMSO-$d_6$, TMS) $\delta$ (ppm):
1.20–1.37 (9H, m), 2.37–3.02 (3H, m), 7.21 (1H, s)

(2) Mass spectrometric data (EI): 178 ($M^+$)

Reference Example 17 (Starting compound for use in Example 44)

(A) A 8.06 g portion of 3-amino-4-methyl-1H-pyrazole was dissolved in 30 ml of acetonitrile and, with cooling on an ice bath, 12.9 g of ethyl propionimidate hydrochloride was added to the solution. The resulting mixture was stirred for 1 hour at the same temperature and then overnight at room temperature. After removing insoluble materials by filtration, the resulting filtrate was concentrated under a reduced pressure, and the thus obtained residue was subjected to silica gel column chromatography. Elution with methanol-chloroform (1:9–3:7, v/v) gave 8.40 g of N-(4-methyl-1H-pyrazol-3-yl)propionamidine hydrochloride.

(1) Nuclear magnetic resonance spectrum (DMSO-$d_6$, TMS) $\delta$ (ppm):
1.30 (3H, t), 2.10 (3H, s), 2.81 (1H, q), 7.66 (1H, s)

(2) Mass spectrometric data (EI): 152 ($M^+$)

(B) A 1.45 g portion of sodium was added to 50 ml of methanol to prepare a sodium methoxide solution. A 4.22 g portion of hydroxylamine hydrochloride was added to the above solution and the thus formed sodium chloride was removed by filtration to prepare a methanol solution of hydroxylamine. On the other hand, 8.39 g of N-(4-methyl-1H-pyrazol-3-yl)propionamidine hydrochloride was dissolved in 50 ml of methanol and cooled on an ice bath.

To this was added dropwise the methanol solution of hydroxylamine prepared above, followed by overnight stirring at room temperature. The reaction mixture was concentrated under a reduced pressure, and the thus obtained residue was subjected to silica gel column chromatography. Elution with methanol-chloroform (1:9, v/v) gave 6.73 g of N-(4-methyl-1 H-pyrazol-3-yl)propionamidoxime.

(1) Nuclear magnetic resonance spectrum (DMSO-$d_6$, TMS) $\delta$ (ppm):
0.87 (3H, t), 1.89 (3H, s), 2.20 (2H, q), 7.39 (1H, s)

(2) Mass spectrometric data (EI): 168 ($M^+$)

(C) In the same manner as the procedure of the step (C) of Reference Example 11, 3.38 g of 2-ethyl-7-methyl-1H-pyrazolo[1,5-b][1,2,4]triazole was obtained from 6.61 g of N-(4-methyl-1H-pyrazol-3-yl)propionamidoxime.

(1) Nuclear magnetic resonance spectrum (DMSO-$d_6$, TMS) $\delta$ (ppm):

1.27 (3H, t), 2.08 (3H, s), 2.74 (2H, q), 7.19 (1H, s), 12.31 (1H, brs)

(2) Mass spectrometric data (EI): 150 (M⁺)

Reference Example 18 (Starting compound for use in Example 45)

(A) A 10.7 g portion of 3-amino-4-methyl-1H-pyrazole was dissolved in 40 ml of acetonitrile and, with cooling on an ice bath, 15.4 g of ethyl acetimidate hydrochloride was added to the solution. The resulting mixture was stirred for 1 hour at the same temperature and then overnight at room temperature. The solid material thus formed was collected by filtration and dissolved in a mixed solvent of methanol-chloroform (3:17, v/v).

After removing insoluble materials by filtration, the resulting filtrate was concentrated under a reduced pressure, and the thus obtained residue was subjected to silica gel column chromatography. Elution with methanolchloroform (¼–⅗, v/v) gave 7.31 g of N-(4-methyl-1 -H-pyrazol-3-yl)acetamidine hydrochloride.

(1) Nuclear magnetic resonance spectrum (DMSO-$d_6$, TMS) δ (ppm):
 2.09 (3H, s), 2.48 (3H, s), 7.65 (1H, s)

(2) Mass spectrometric data (FAB): 139 (MH⁺)

(B) In the same manner as described in the step (B) of Reference Example 17, 5.45 g of N-(4-methyl-1 H-pyrazol-3-yl)acetamidoxime was obtained from 7.20 g of N-(4-methyl-1H-pyrazol-3-yl)acetamidine hydrochloride.

(1) Nuclear magnetic resonance spectrum (DMSO-$d_6$, TMS) δ (ppm):
 1.72 (3H, s), 1.89 (3H, s), 7.39 (1H, s)

(2) Mass spectrometric data (EI): 154 (M⁺)

(C) In the same manner as the procedure of the step (C) of Reference Example 11, 2.14 g of 2,7-dimethyl-1H-pyrazolo[ 1,5-b][1,2,4]triazole was obtained from 5.38 g of N-(4-methyl-1H-pyrazol-3-yl)acetamidoxime.

(1) Nuclear magnetic resonance spectrum (DMSO-$d_6$, TMS) δ (ppm):
 2.07 (3H, s), 2.38 (3H, s), 7.19 (1H, s), 12.35 (1H, brs)

(2) Mass spectrometric data (EI): 136 (M⁺)

Reference Example 19 (Starting compound for use in Example 46)

(A) A 5.28 g portion of 3-amino-4-ethyl-1H-pyrazole was dissolved in 30 ml of acetonitrile and, with cooling on an ice bath, 8.20 g of ethyl isobutylimidate hydrochloride was added to the solution. The resulting mixture was stirred for 1 hour at the same temperature and then overnight at room temperature. The solid material thus formed was collected by filtration and dissolved in a mixed solvent of methanol-chloroform (1/4, v/v). After removing insoluble materials by filtration, the resulting filtrate was concentrated under a reduced pressure to give 7.29 g of N-(4 -ethyl-1H-pyrazol-3-yl)isobutylamidine hydrochloride.

(1) Nuclear magnetic resonance spectrum (DMSO-$d_6$, TMS) δ (ppm):
 1.12 (3H, t), 1.33 (6H, d), 3.32 (1H, m), 7.71 (1H, s)

(2) Mass spectrometric data (EI): 180 (M⁺)

(B) In the same manner as described in the step (B) of Reference Example 17, 6.10 g of N-(4-ethyl-1H-pyrazol-3-yl)isobutylamidoxime was obtained from 7.21 g of N-(4-ethyl-1H-pyrazol-3-yl)isobutylamidine hydrochloride.

(1) Nuclear magnetic resonance spectrum (DMSO-$d_6$, TMS) δ (ppm):
 0.97 (6H, d), 1.10 (3H, t), 2.31 (2H, q), 2.86 (1H, m), 7.41 (1H, s)

(2) Mass spectrometric data (EI): 196 (M⁺)

(C) In the same manner as the procedure of the step (C) of Reference Example 11, 2.52 g of 7-ethyl-2 -isopropyl-1H-pyrazolo[1,5-b][1,2,4]triazole was obtained from 5.98 g of N-(4-ethyl-1H-pyrazol-3-yl)isobutylamidoxime.

(1) Nuclear magnetic resonance spectrum (DMSO-$d_6$, TMS) δ (ppm):
 1.20 (3H, t), 1.32 (6H, d), 1.51 (2H, q), 3.07 (1H, m), 7.22 (1H, s), 12.28 (1H, br)

(2) Mass spectrometric data (EI): 178 (M⁺)

Reference Example 20 (Starting compound for use in Example 47)

(A) In the same manner as described in the step (A) of Reference Example 18, 15.8 g of N-(5-ethyl-1H-pyrazol-3-yl)butylamidine hydrochloride was obtained from 13.7 g of 3-amino-5-ethyl-1H-pyrazole and 21.1 g of ethyl butylimidate hydrochloride.

(1) Nuclear magnetic resonance spectrum (DMSO-$d_6$, TMS) δ (ppm):
 0.95 (3H, t), 1.20 (3H, t), 1.77 (2H, m), 2.61– 2.69 (4H, m), 6.05 (1H, s)

(2) Mass spectrometric data (EI): 180 (M⁺)

(B) In the same manner as described in the step (B) of Reference Example 17, 12.0 g of N-(5-ethyl-1H-pyrazol-3-yl)butylamidoxime was obtained from 15.7 g of N-(5-ethyl- 1H-pyrazol-3-yl)butylamidine hydrochloride.

(1) Nuclear magnetic resonance spectrum (DMSO-$d_6$, TMS) δ (ppm):
 0.83 (3H, t), 1.15 (3H, t), 1.40 (2H, m), 2.52 (2H, q), 5.70 (1H, s)

(2) Mass spectrometric data (EI): 196 (M⁺)

(C) In the same manner as the procedure of the step (C) of Reference Example 11, 3.87 g of 6-ethyl-2-propyl-1H-pyrazolo[1,5-b][1,2,4]triazole was obtained from 12.0 g of N-(5-ethyl-1H-pyrazol-3-yl)butylamidoxime.

(1) Nuclear magnetic resonance spectrum (DMSO-$d_6$, TMS) δ (ppm):
 0.94 (3H, t), 1.19 (3H, t), 1.71 (2H, m), 2.59 (2H, q), 2.68 (2H, t), 5.54 (1H, s), 12.28 (1H, brs)

(2) Mass spectrometric data (EI): 178 (M⁺)

Reference Example 21 (Starting compound for use in Example 48)

(A) In the same manner as described in the step (A) of Reference Example 17, 14.3 g of N-(5-ethyl-1H-pyrazol-3-yl)propionamidine hydrochloride was obtained from 13.5 g of 3-amino-5-ethyl-1H-pyrazole and 18.9 g of ethyl propionimidate hydrochloride.

(1) Nuclear magnetic resonance spectrum (DMSO-$d_6$, TMS) δ (ppm):
 1.20 (3H, t), 1.28 (3H, t), 2.55–2.81 (4H, m), 6.03 (1H, s)

(2) Mass spectrometric data (EI): 166 (M⁺)

(B) In the same manner as described in the step (B) of Reference Example 17, 10.3 g of N-(5-ethyl-1H-pyrazol-3-yl)propionamidoxime was obtained from 14.2 g of N-(5-ethyl- 1H-pyrazol-3-yl)propionamidine hydrochloride.

(1) Nuclear magnetic resonance spectrum (DMSO-$d_6$, TMS) δ (ppm):

0.96 (3H, t), 1.16 (3H, t), 2.31–2.65 (4H, m), 5.73 (1H, s)

(2) Mass spectrometric data (EI): 182 (M⁺)

(C) In the same manner as the procedure of the step (C) of Reference Example 11, 4.38 g of 2,6-diethyl-1H-pyrazolo[1,5-b][1,2,4]triazole was obtained from 10.2 g of N-(5-ethyl-1H-pyrazol-3-yl)propionamidoxime.

(1) Nuclear magnetic resonance spectrum (DMSO-d₆, TMS) δ (ppm):
  1.19 (3H, t), 1.27 (3H, t), 2.48–2.85 (4H, m), 5.55 (1H, s), 12.28 (1H, brs)

(2) Mass spectrometric data (EI): 164 (M⁺)

Reference Example 22 (Starting compound for use in Example 49)

(A) In the same manner as described in the step (A) of Reference Example 19, 9.97 g of N-(5-ethyl-1H-pyrazol-3-yl)acetamidine hydrochloride was obtained from 12.9 g of 3-amino-5-ethyl-1H-pyrazole and 16.3 g of ethyl acetimidate hydrochloride.

(1) Nuclear magnetic resonance spectrum (DMSO-d₆, TMS) δ (ppm):
  1.19 (3H, t), 2.41 (3H, s), 2.64 (2H, q), 6.00 (1H, s)

(2) Mass spectrometric data (EI): 152 (M⁺)

(B) In the same manner as described in the step (B) of Reference Example 17, 8.28 g of N-(5-ethyl-1H-pyrazol-3-yl)acetamidoxime was obtained from 13.3 g of N-(5-ethyl-1H-pyrazol-3-yl)acetamidine hydrochloride.

(1) Nuclear magnetic resonance spectrum (DMSO-d₆, TMS) δ (ppm):
  1.93 (3H, s), 2.52 (2H, q), 5.73 (1H, s)

(2) Mass spectrometric data (EI): 168 (M⁺)

(C) In the same manner as the procedure of the step (C) of Reference Example 11, 2.04 g of 6-ethyl-2-methyl-1H-pyrazolo[1,5-b][1,2,4]triazole was obtained from 8.18 g of N-(5-ethyl-1H-pyrazol-3-yl)acetamidoxime.

(1) Nuclear magnetic resonance spectrum (DMSO-d₆, TMS) δ (ppm):
  1.19 (3H, t), 2.37 (3H, s), 2.58 (2H, q), 5.53 (1H, s), 12.27 (1H, brs)

(2) Mass spectrometric data (EI): 150 (M⁺)

Reference Example 23 (Starting compound for use in Example 50)

(A) In the same manner as described in the step (A) of Reference Example 18, 14.5 g of N-(5-butyl-1H-pyrazol-3-yl)propionamidine hydrochloride was obtained from 14.9 g of 3-amino-5-butyl-1H-pyrazole and 16.6 g of ethyl propionimidate hydrochloride.

(1) Nuclear magnetic resonance spectrum (DMSO-d₆, TMS) δ (ppm):
  0.89 (3H, t), 1.06–1.74 (7H, m), 2.54–2.80 (4H, m), 6.02 (1H, s)

(2) Mass spectrometric data (EI): 194 (M⁺)

(B) In the same manner as described in the step (B) of Reference Example 17, 11.0 g of N-(5-butyl-1H-pyrazol-3-yl)propionamidoxime was obtained from 14.4 g of N-(5-butyl-1H-pyrazol-3-yl)propionamidine hydrochloride.

(1) Nuclear magnetic resonance spectrum (DMSO-d₆, TMS) δ (ppm):
  0.87 (3H, t), 0.95 (3H, t), 5.72 (1H, s)

(2) Mass spectrometric data (EI): 210 (M⁺)

(C) In the same manner as the procedure of the step (C) of Reference Example 11, 3.08 g of 6-butyl-2-ethyl-1H-pyrazolo[1,5-b][1,2,4]triazole was obtained from 10.9 g of N-(5-butyl-1H-pyrazol-3-yl)propionamidoxime.

(1) Nuclear magnetic resonance spectrum (DMSO-d₆, TMS) δ (ppm):
  0.89 (3H, t), 1.27 (3H, t), 1.33 (2H, m), 1.59 (2H, m), 2.56 (2H, t), 2.73 (2H, q), 5.53 (1H, s), 12.29 (1H, brs)

(2) Mass spectrometric data (EI): 192 (M⁺)

Reference Example 24 (Starting compound for use in Example 51)

(A) In the same manner as described in the step (A) of Reference Example 17, 10.9 g of N-(1H-pyrazol-3-yl)propionamidine hydrochloride was obtained from 10.2 g of 3-aminopyrazole and 19.0 g of ethyl propionimidate hydrochloride.

(1) Nuclear magnetic resonance spectrum (DMSO-d₆, TMS) δ (ppm):
  1.31 (3H, t), 2.73 (2H, q), 6.29 (1H, brs), 7.89 (1H, brs)

(2) Mass spectrometric data (EI): 138 (M⁺)

(B) In the same manner as described in the step (B) of Reference Example 17, 8.41 g of N-(1H-pyrazol-3-yl)propionamidoxime was obtained from 10.7 g of N-(1H-pyrazol-3-yl)propionamidine hydrochloride.

(1) Nuclear magnetic resonance spectrum (DMSO-d₆, TMS) δ (ppm):
  0.95 (3H, t), 2.41 (2H, q), 5.94 (1H, d), 7.53 (1H, d)

(2) Mass spectrometric data (EI): 154 (M⁺)

(C) In the same manner as the procedure of the step (C) of Reference Example 11, 1.39 g of 2-ethyl-1H-pyrazolo[1,5-b][1,2,4]triazole was obtained from 8.30 g of N-(1H-pyrazol-3-yl)propionamidoxime.

(1) Nuclear magnetic resonance spectrum (DMSO-d₆, TMS) δ (ppm):
  1.28 (3H, t), 2.77 (2H, q), 5.74 (1H, d), 7.40 (1H, d), 12.43 (1H, brs)

(2) Mass spectrometric data (EI): 136 (M⁺)

Example 38

(38a)

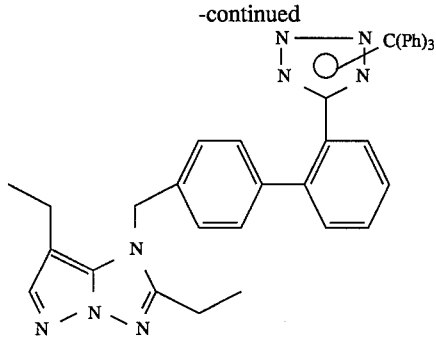

(38b)

A 1.67 g portion of 2,7-diethyl-1H-pyrazolo[1,5-b][1,2,4]triazole was dissolved in 30 ml of N,N-dimethylformamide, and 1.3 g of potassium t-butoxide was added to the solution. After stirring for 10 minutes at room temperature, the reaction mixture was cooled on an ice bath and mixed with 6.8 g of N-triphenylmethyl-5-[2-(4'-bromomethyl-biphenylyl)]tetrazole, and the mixture was stirred for 30 minutes at the same temperature and then overnight at room temperature. After removing the solvent by distillation under a reduced pressure, the thus obtained residue was mixed with ethyl acetate and washed with water.

The resulting ethyl acetate layer was dried over anhydrous magnesium sulfate and concentrated under a reduced pressure, and the thus obtained residue was subjected to silica gel column chromatography. Elution with ethyl acetate-n-hexane (1:1–7:3, v/v) gave 5.8 g of 2,7-diethyl- 5-[[2'-(N-triphenylmethyl-tetrazol-5-yl)biphenyl-4 -yl]methyl]-5H-pyrazolo[1,5-b][1,2,4]triazole (compound 38a) and 310 mg of 2,7-diethyl-1-[[2'-(N-triphenylmethyl-tetrazol-5-yl)biphenyl-4-yl]methyl]-1H-pyrazolo[1,5-b][1,2,4]triazole (compound 38b).

Compound 38a;

(1) Melting point: 157°–158.5° C. (decomposition)
(2) Nuclear magnetic resonance spectrum (CDCl$_3$, TMS) δ (ppm):
  1.21 (3H, t), 1.40 (3H, t), 2.55 (2H, q), 2.87 (2H, q), 5.10 (2H, s)
(3) Mass spectrometric data (FAB): 641 (MH$^+$)

Compound 38b;

(1) Melting point: 178°–179° C. (decomposition)
(2) Nuclear magnetic resonance spectrum (CDCl$_3$, TMS) δ (ppm):
  1.04 (3H, t), 1.28 (3H, t), 2.31 (2H, q), 2.59 (2H, q), 5.06 (2H, s)
(3) Mass spectrometric data (FAB): 641 (MH$^+$)

Example 39

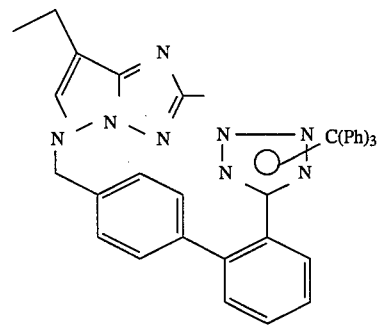

In the same manner as described in Example 38, 1.1 g of 7-ethyl-2-methyl-5-[[2'-(N-triphenylmethyl-tetrazol-5 -yl)biphenyl-4-yl]methyl]-5H-pyrazolo[1,5-b][1,2,4]triazole was obtained from 540 mg of 7-ethyl-2-methyl-1H-pyrazolo[1,5-b][1,2,4]triazole.

(1) Nuclear magnetic resonance spectrum (CDCl$_3$, TMS) δ (ppm):
  1.22 (3H, t), 2.50 (3H, s), 2.53 (2H, q), 5.08 (2H, s)
(2) Mass spectrometric data (FAB): 627 (MH$^+$)

Example 40

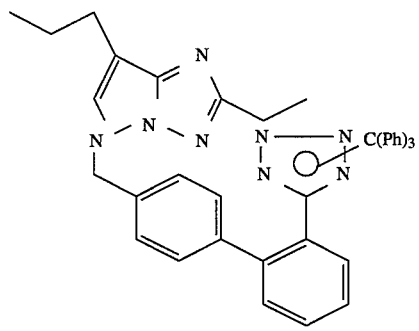

In the same manner as described in Example 38, 1.5 g of 2-ethyl-7-n-propyl-5-[[2'-(N-triphenylmethyl-tetrazol- 5-yl)biphenyl-4-yl]methyl]-5H-pyrazolo[1,5-b][1,2,4]triazole was obtained from 500 mg of 2-ethyl-7-n-propyl-1H-pyrazolo[1,5-b][1,2,4]triazole.

(1) Nuclear magnetic resonance spectrum (CDCl$_3$, TMS) δ (ppm):
  0.92 (3H, t), 1.40 (3H, t), 1.61–1.68 (2H, m) 2.48 (2H, t), 2.88 (2H, q), 5.11 (2H, s)

(2) Mass spectrometric data (FAB): 655 (MH⁺)

Example 41

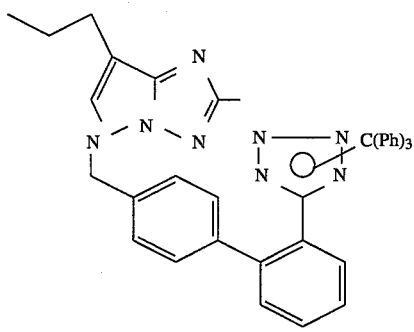

In the same manner as described in Example 38, 1.7 g of 2-methyl-7-n-propyl-5-[[2'-(N-triphenylmethyl-tetrazol-5-yl)biphenyl-4-yl]methyl]-5H-pyrazolo[1,5-b][1,2,4]triazole was obtained from 500 mg of 2-methyl-7-n-propyl-1H-pyrazolo[1,5-b][1,2,4]triazole.

(1) Nuclear magnetic resonance spectrum (CDCl₃, TMS) δ (ppm):
0.92 (3H, t), 1.67 (2H, m), 2.49 (2H, t), 2.55 (3H, s), 5.13 (2H, s)

(2) Mass spectrometric data (FAB): 641 (MH⁺)

Example 42

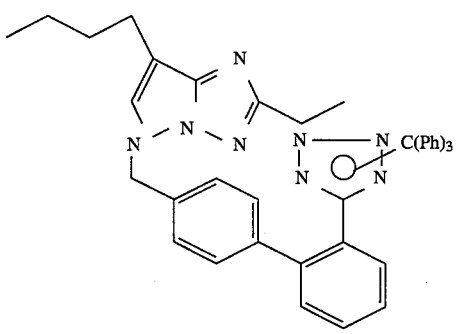

In the same manner as described in Example 38, 660 mg of 7-n-butyl-2-ethyl-5-[[2'-(N-triphenylmethyl-tetrazol-5-yl)biphenyl-4-yl]methyl]-5H-pyrazolo[1,5-b][1,2,4]triazole was obtained from 490 mg of 7-n-butyl-2-ethyl-1H-pyrazolo[1,5-b][1,2,4]triazole.

(1) Nuclear magnetic resonance spectrum (CDCl₃, TMS) δ (ppm):
0.89 (3H, t), 1.34 (2H, m), 1.41 (3H, t), 1.61 (2H, m), 2.53 (2H, t), 2.91 (2H, q), 5.13 (2H, s)

(2) Mass spectrometric data (FAB): 669 (MH⁺)

Example 43

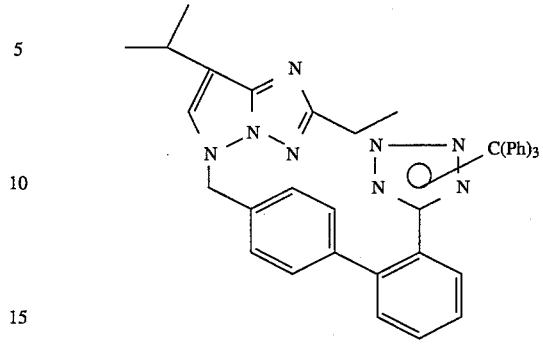

In the same manner as described in Example 38, 1.2 g of 2-ethyl-7-isopropyl-5-[[2'-(N-triphenylmethyl-tetrazol-5-yl)biphenyl-4-yl]methyl]-5H-pyrazolo[1,5-b][1,2,4]triazole was obtained from 500 mg of 2-ethyl-7-isopropyl-1H-pyrazolo[1,5-b][1,2,4]triazole.

(1) Nuclear magnetic resonance spectrum (CDCl₃, TMS) δ (ppm):
1.26–1.29 (6H, m), 1.41 (3H, t), 2.91 (2H, q), 2.96 (1H, m), 5.13 (2H, s)

(2) Mass spectrometric data (FAB): 655 (MH⁺)

Example 44

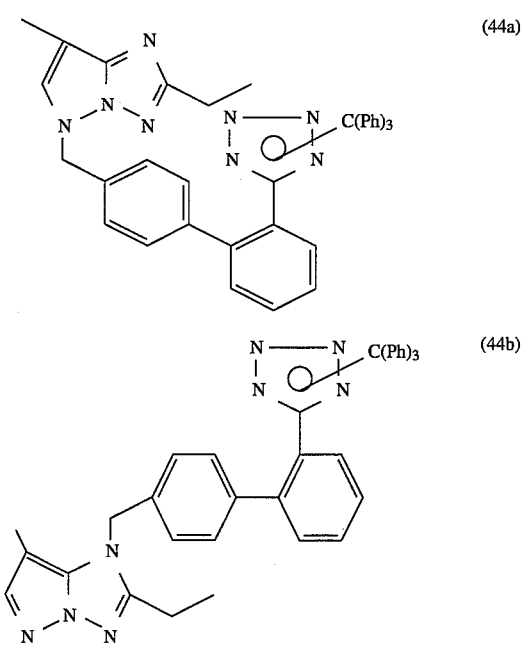

In the same manner as described in Example 38, 1.5 g of 2-ethyl-7-methyl-5-[[2'-(N-triphenylmethyl-tetrazol- 5-yl)biphenyl-4-yl]methyl]-5H-pyrazolo[1,5-b][1,2,4]triazole (compound 44a) and 330 mg of 2-ethyl-7-methyl-1-[[2'-(N-triphenylmethyl-tetrazol- 5-yl)biphenyl-4-yl]methyl]-1H-pyrazolo[1,5-b][1,2,4]triazole (compound 44b) were obtained from 500 mg of 2-ethyl-7-methyl-1H-pyrazolo[1,5-b][1,2,4]triazole.

Compound 44a;

(1) Nuclear magnetic resonance spectrum (CDCl₃, TMS)

δ (ppm):

1.40 (3H, t), 2.11 (3H, s), 2.87 (2H, q), 5.09 (2H, s)

(2) Mass spectrometric data (FAB): 627 (MH⁺)

Compound 44b;

(1) Nuclear magnetic resonance spectrum (CDCl₃, TMS)

δ (ppm):

1.29 (3H, t), 1.91 (3H, s), 2.61 (2H, q), 5.05 (2H, s)

(2) Mass spectrometric data (FAB): 627 (MH⁺)

Example 45

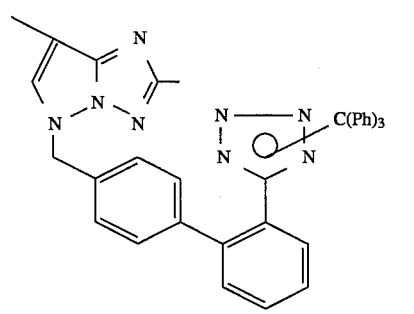

(44a)

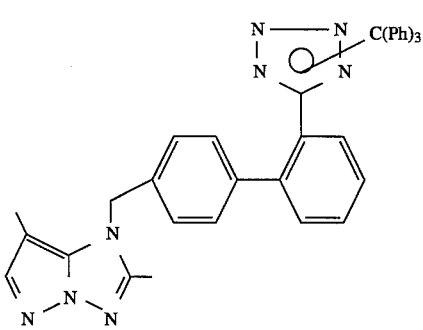

(44b)

In the same manner as described in Example 38, 1.5 g of 2,7-dimethyl-5-[[2'-(N-triphenylmethyl-tetrazol-5 -yl)biphenyl-4-yl]methyl]-5H-pyrazolo[1,5-b][1,2,4]triazole (compound 45a) and 560 mg of 2,7-dimethyl-1-[[2'-(N-triphenylmethyl-tetrazol- 5-yl)biphenyl-4-yl]methyl]-1 H-pyrazolo[1,5-b][1,2,4]triazole (compound 45b) were obtained from 500 mg of 2,7-dimethyl-1H-pyrazolo[1,5-b][1,2,4]triazole.

Compound 45a;

(1) Nuclear magnetic resonance spectrum (CDCl₃, TMS)

δ (ppm):

2.11 (3H, s), 2.52 (3H, s), 5.09 (2H, s)

(2) Mass spectrometric data (FAB): 613 (MH⁺)

Compound 45b;

(1) Nuclear magnetic resonance spectrum (CDCl₃, TMS)

δ (ppm):

1.94 (3H, s), 2.30 (3H, s), 5.07 (2H, s)

(2) Mass spectrometric data (FAB): 613 (MH⁺)

Example 46

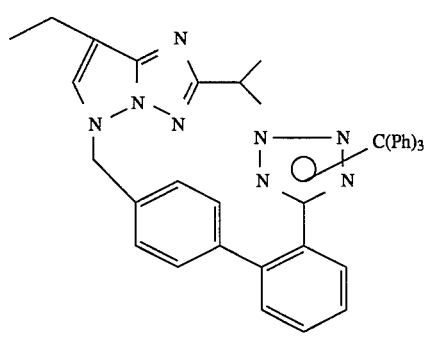

In the same manner as described in Example 38, 3.70 g of 7-ethyl-2-isopropyl-5-[[2'-(N-triphenylmethyl-tetrazol-5-yl)biphenyl-4-yl]methyl]-5H-pyrazolo[1,5-b][1,2,4]triazole was obtained from 1.20 g of 7-ethyl-2-isopropyl-1H-pyrazolo[1,5-b][1,2,4]triazole.

(1) Nuclear magnetic resonance spectrum (CDCl₃, TMS)

δ (ppm):

1.20 (3H, t), 1.42 (6H, d), 2.57 (2H, q), 3.19 (1H, m), 5.10 (2H, s)

(2) Mass spectrometric data (FAB): 655 (MH⁺)

Example 47

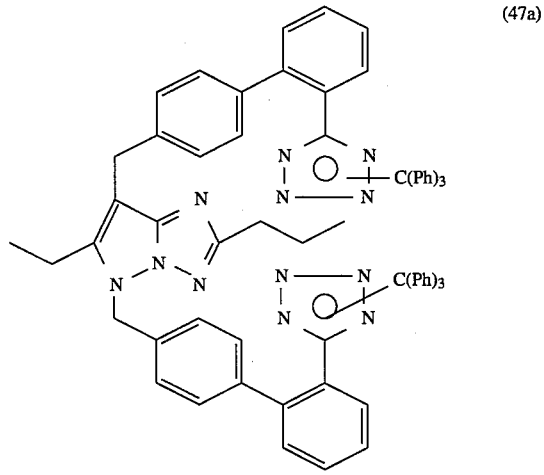

(47a)

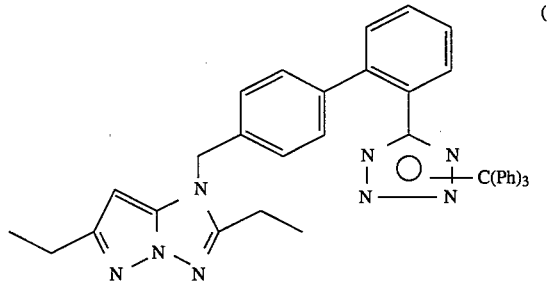

(47b)

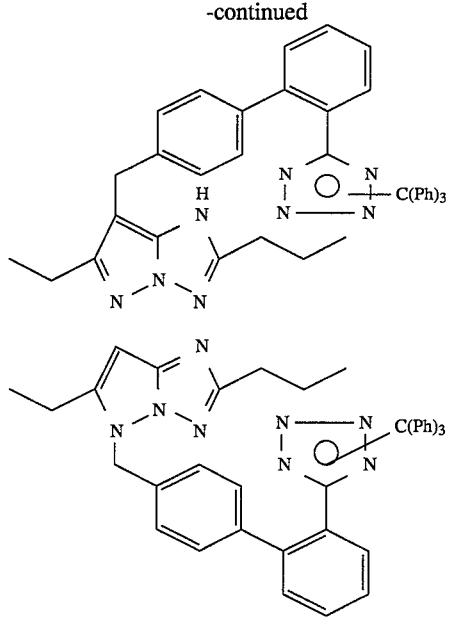

In the same manner as described in Example 38, 0.49 g of 5,7-bis[[2'-(N-triphenylmethyl-tetrazol-5 -yl)biphenyl-4-yl]methyl]-6-ethyl-2-propyl-5 H-pyrazolo[1,5-b][1,2,4]triazole (compound 47a), 2.30 g of 6-ethyl-2-propyl-1-[[2'-(N-triphenylmethyl-tetrazol-5 -yl)biphenyl-4-yl]methyl]-1H-pyrazolo[1,5-b][1,2,4]triazole (compound 47b), 0.18 g of 6-ethyl-2-propyl-7-[[2'-(N-triphenylmethyl-tetrazol- 5-yl)biphenyl-4-yl]methyl]-1H-pyrazolo[ 1,5-b][1,2,4]triazole (compound 47c) and 2.28 g of 6-ethyl-2-propyl-5-[[2'-(N-triphenylmethyl-tetrazol-5 -yl)biphenyl-4-yl]methyl]-5H-pyrazolo[1,5-b][1,2,4]triazole (compound 47d) were obtained from 2.17 g of 6-ethyl-2-propyl-1H-pyrazolo[1,5-b][1,2,4]triazole.

Compound 47a;
(1) Nuclear magnetic resonance spectrum (CDCl$_3$, TMS) δ (ppm):
0.92 (3H, t), 1.00 (3H, t), 1.84 (2H, m), 2.41 (2H, q), 2.79 (2H, t), 3.85 (2H, s), 5.20 (2H, s)
(2) Mass spectrometric data (FAB): 1131 (MH$^+$)

Compound 47b;
(1) Nuclear magnetic resonance spectrum (CDCl$_3$, TMS) δ (ppm):
0.98 (3H, t), 1.23 (3H, t), 1.75 (2H, m), 2.61 (2H, t), 2.68 (2H, q), 4.93 (2H, s), 5.23 (2H, s)
(2) Mass spectrometric data (FAB): 655 (MH$^+$)

Compound 47c;
(1) Nuclear magnetic resonance spectrum (CDCl$_3$, TMS) δ (ppm):
0.68 (3H, t), 1.33 (3H, t), 1.42 (2H, m), 2.22 (2H, t), 2.75 (2H, q), 3.81 (2H, s)
(2) Mass spectrometric data (FAB): 655 (MH$^+$)

Compound 47d;
(1) Nuclear magnetic resonance spectrum (CDCl$_3$, TMS) δ (ppm):
0.99 (3H, t), 1.21 (3H, t), 2.50 (2H, q), 2.75 (2H, t), 5.27 (2H, s), 5.89 (1H, s)
(2) Mass spectrometric data (FAB): 655 (MH$^+$)

Example 48

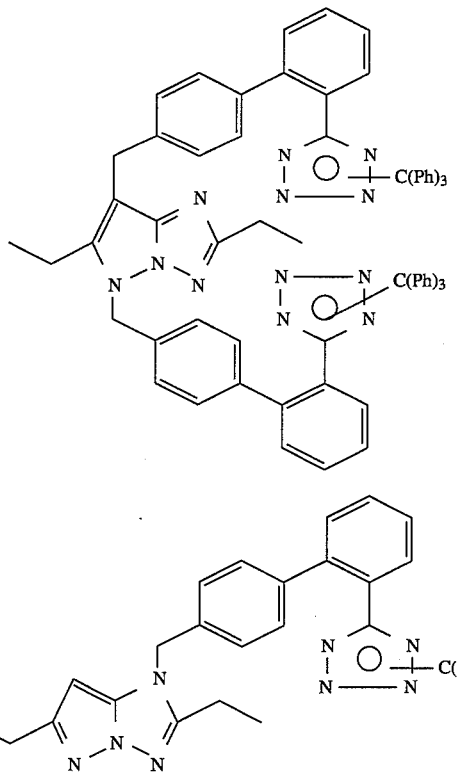

In the same manner as described in Example 38, 0.31 g of 5,7-bis[[2'-(N-triphenylmethyl-tetrazol-5 -yl)biphenyl-4-yl]methyl]-2,6-diethyl-5H-pyrazolo[ 1,5-b][1,2,4]triazole (compound 48a), 2.60 g of 2,6 -diethyl-1-[[2'-(N-triphenylmethyl-tetrazol-5-yl)biphenyl-4-yl] methyl]-1H-pyrazolo[1,5-b][1,2,4]triazole (compound 48b), 0.20 g of 2,6-diethyl-7-[[2'-(N-triphenylmethyl-tetrazol-5 -yl)biphenyl-4-yl]methyl]-1H-pyrazolo[1,5-b][1,2,4]triazole (compound 48c) and 2.04 g of 2,6-diethyl-5-[[2'-(N-triphenylmethyl-tetrazol-5-yl)biphenyl-4-yl]methyl]-5H-pyrazolo[ 1,5-b][1,2,4]triazole (compound 48d) were obtained from 2.00 g of 2,6-diethyl-1H-pyrazolo[1,5-b][1,2,4]triazole.

Compound 48a;

(1) Nuclear magnetic resonance spectrum (CDCl₃, TMS) δ (ppm):
0.92 (3H, t), 1.37 (3H, t), 2.41 (2H, q), 2.84 (2H, q), 3.86 (2H, s), 5.21 (2H, s)

(2) Mass spectrometric data (FAB): 1117 (MH⁺)

Compound 48b;

(1) Nuclear magnetic resonance spectrum (CDCl₃, TMS) δ (ppm):
1.24 (3H, t), 1.29 (3H, t), 2.64 (2H, 2.69 (2H, q), 4.92 (2H, s), 5.25 (1H, s)

(2) Mass spectrometric data (FAB): 641 (MH⁺)

Compound 48c;

(1) Nuclear magnetic resonance spectrum (CDCl₃, TMS) δ (ppm):
0.96 (3H, t), 1.32 (3H, t), 2.26 (2H, q), 2.74 (2H, q), 3.80 (2H, s)

(2) Mass spectrometric data (FAB): 641 (MH⁺)

Compound 48d;

(1) Nuclear magnetic resonance spectrum (CDCl₃, TMS) δ (ppm):
1.22 (3H, t), 1.38 (3H, t), 2.53 (2H, 2.85 (2H, q), 5.30 (2H, s), 5.98 (1H, s)

(2) Mass spectrometric data (FAB): 641 (MH⁺)

Example 49

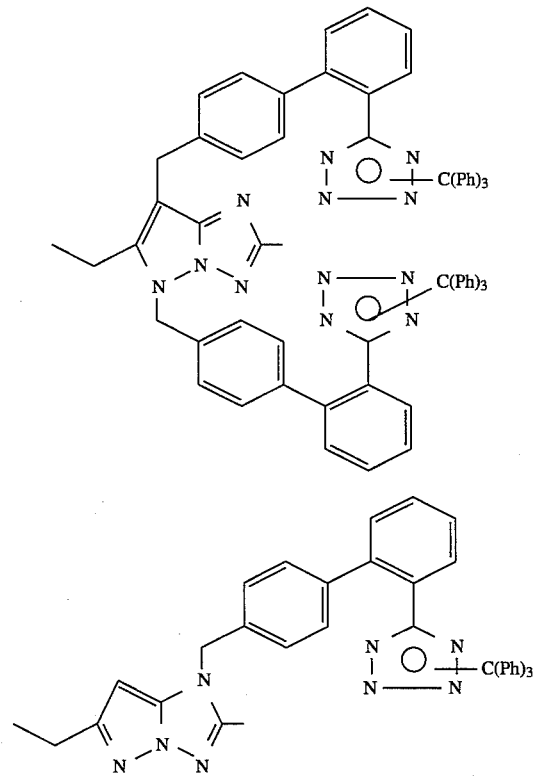

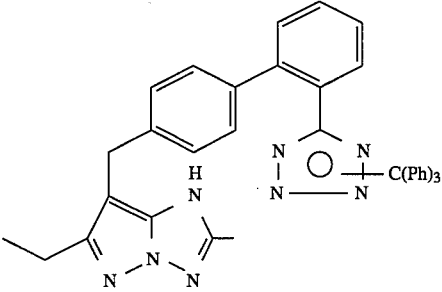

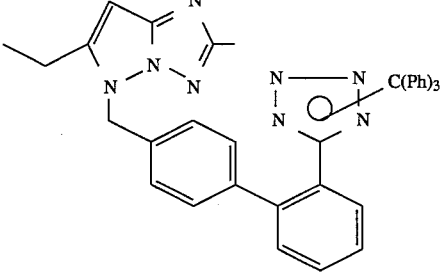

In the same manner as described in Example 38, 0.40 g of 5,7-bis[[2'-(N-triphenylmethyl-tetrazol-5-yl)biphenyl-4-yl]methyl]-6-ethyl-2-methyl-5H-pyrazolo[1,5-b][1,2,4]triazole (compound 49a), 2.96 g of 6-ethyl-2-methyl-1-[[2'-(N-triphenylmethyl-tetrazol-5-yl)biphenyl-4-yl]methyl]-1H-pyrazolo[1,5-b][1,2,4]triazole (compound 49b), 0.29 g of 6-ethyl-2-methyl-7-[[2'-(N-triphenylmethyl-tetrazol-5-yl)biphenyl-4-yl]methyl]-1H-pyrazolo[1,5-b][1,2,4]triazole (compound 49c) and 1.75 g of 6-ethyl-2-methyl-5-[[2'-(N-triphenylmethyl-tetrazol-5-yl)biphenyl-4-yl]methyl]-5H-pyrazolo[1,5-b][1,2,4]triazole (compound 49d) were obtained from 1.84 g of 6-ethyl-2-methyl-1H-pyrazolo[1,5-b][1,2,4]triazole.

Compound 49a;

(1) Nuclear magnetic resonance spectrum (CDCl₃, TMS) δ (ppm):
0.94 (3H, t), 2.43 (2H, q), 2.48 (3H, s), 3.84 (2H, s), 5.21 (2H, s)

(2) Mass spectrometric data (FAB): 1103 (MH⁺)

Compound 49b;

(1) Nuclear magnetic resonance spectrum (CDCl₃, TMS) δ (ppm):
1.24 (3H, t), 2.34 (3H, s), 2.69 (2H, q), 4.94 (2H, s), 5.28 (1H, s)

(2) Mass spectrometric data (FAB): 627 (MH⁺)

Compound 49c;

(1) Nuclear magnetic resonance spectrum (CDCl₃, TMS) δ (ppm):
1.33 (3H, t), 1.89 (3H, s), 2.75 (2H, q), 3.81 (2H, s)

(2) Mass spectrometric data (FAB): 627 (MH⁺)

Compound 49d;

(1) Nuclear magnetic resonance spectrum (CDCl₃, TMS) δ (ppm):
1.23 (3H, t), 2.48 (3H, s), 2.54 (2H, q), 5.29 (2H, s), 5.94 (1H, s)

(2) Mass spectrometric data (FAB): 627 (MH⁺)

Example 50

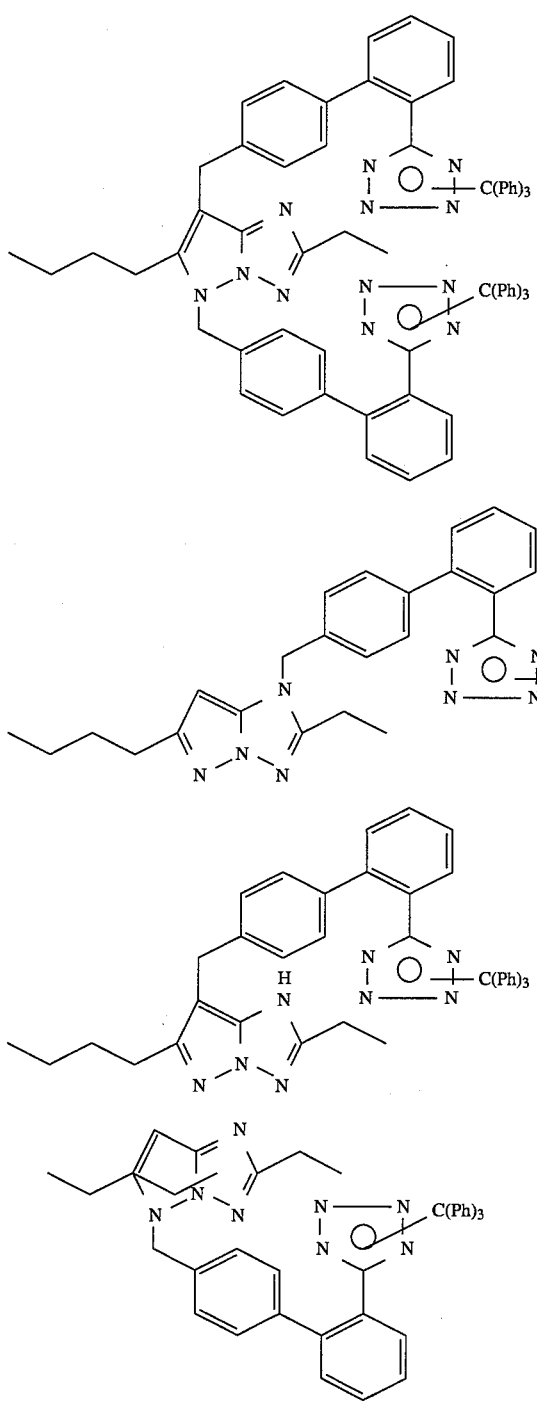

In the same manner as described in Example 38, 0.61 g of 5,7-bis[[2'-(N-triphenylmethyl-tetrazol-5-yl)biphenyl-4-yl]methyl]-6-butyl-2-ethyl-5H-pyrazolo[1,5-b][1,2,4]triazole (compound 50a), 2.52 g of 6-butyl-2-ethyl-1-[[2'-(N-triphenylmethyl-tetrazol-5-yl)biphenyl-4-yl]methyl]-1H-pyrazolo[1,5-b][1,2,4]triazole (compound 50b), and 2.31 g of a mixture consisting (about 1:8) of 6-butyl-2-ethyl-7-[[2'-(N-triphenylmethyl-tetrazol-5-yl)biphenyl-4-yl]methyl]-1H-pyrazolo[1,5-b][1,2,4]triazole (compound 50c) and 6-butyl-2-ethyl-5-[[2'-(N-triphenylmethyl-tetrazol-5-yl)biphenyl-4-yl]methyl]-5H-pyrazolo[1,5-b][1,2,4]triazole (compound 50d) were obtained from 2.34 g of 6-butyl-2-ethyl-1H-pyrazolo[1,5-b][1,2,4]triazole.

Compound 50a;

(1) Nuclear magnetic resonance spectrum (CDCl₃, TMS) δ (ppm):

0.79 (3H, t), 1.37 (3H, t), 2.42 (2H, t), 2.83 (2H, q), 3.85 (2H, s), 5.21 (2H, s)

(2) Mass spectrometric data (FAB): 1145 (MH⁺)

Compound 50b;

(1) Nuclear magnetic resonance spectrum (CDCl₃, TMS) δ (ppm):

0.91 (3H, t), 1.30 (3H, t), 1.38 (2H, m), 2.62–2.67 (4H, m), 4.92 (2H, s), 5.24 (1H, s)

(2) Mass spectrometric data (FAB): 669 (MH⁺)

Example 51

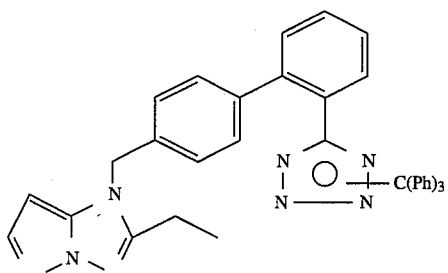

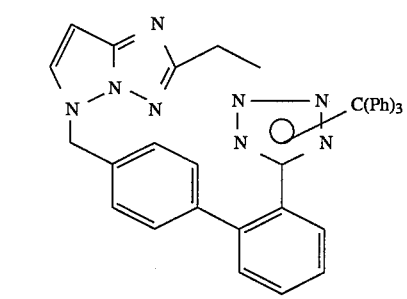

In the same manner as described in Example 38, 612 mg of 2-ethyl-1-[[2'-(N-triphenylmethyl-tetrazol-5-yl)biphenyl-4-yl]methyl]-1H-pyrazolo[1,5-b][1,2,4]triazole (compound 51a) and 449 mg of 2-ethyl-5-[[2'-(N-triphenylmethyl-tetrazol-5-yl)biphenyl-4-yl]methyl]-5H-pyrazolo[1,5-b][1,2,4]triazole (compound 51b) were obtained from 378 mg of 2-ethyl-1H-pyrazolo[1,5-b][1,2,4]triazole.

Compound 51a;

(1) Nuclear magnetic resonance spectrum (CDCl₃, TMS) δ (ppm):

1.34 (3H, t), 2.69 (2H, q), 5.00 (2H, s), 5.40 (1H, s)

(2) Mass spectrometric data (FAB): 613 (MH⁺)

Compound 51b;

(1) Nuclear magnetic resonance spectrum (CDCl₃, TMS) δ (ppm):

1.41 (3H, t), 2.90 (2H, q), 5.23 (2H, s), 6.07 (1H, d)

(2) Mass spectrometric data (FAB): 613 (MH⁺)

Example 52

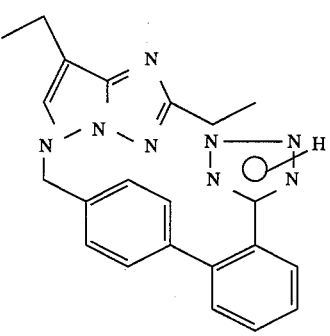

A mixture consisting of 5.8 g of 2,7-diethyl-5- [[2'-(N-triphenylmethyl-tetrazol-5-yl)biphenyl-4-yl]methyl]-5H-pyrazolo[1,5-b][1,2,4]triazole (compound 38a), 180 ml of ethanol and 20 ml of acetic acid was heated under reflux for 3 hours. After removing the solvent by distillation under a reduced pressure, the resulting residue was mixed with toluene and again subjected to distillation removal of the solvent under a reduced pressure. The thus obtained residue was mixed with ethyl acetate to give 3.3 g of crystals. By recrystallizing them from ethanol, 2.8 g of 2,7-diethyl-5-[[2'-(tetrazol-5-yl)biphenyl-4-yl]methyl]-5H-pyrazolo[1,5-b][1,2,4]triazole was obtained in the form of colorless crystals.

(1) Melting point: 184°–186° C.

(2) Elemental analysis data (for $C_{22}H_{22}N_8$)

|  | C (%) | H (%) | N (%) |
|---|---|---|---|
| calculated: | 66.31 | 5.56 | 28.12 |
| found: | 66.25 | 5.71 | 27.86 |

(3) Nuclear magnetic resonance spectrum (DMSO-$d_6$, TMS) δ (ppm):
1.21–1.27 (6H, m), 2.52 (2H, q), 2.65 (2H, q), 5.36 (2H, s), 7.07 (2H, d), 7.21 (2H, d)

(4) Mass spectrometric data (FAB): 399 (MH$^+$)

Example 53

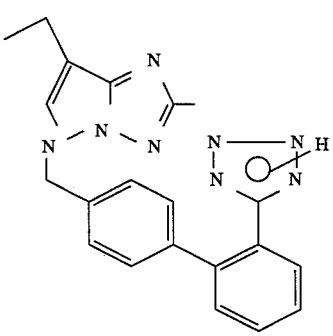

In the same manner as described in Example 12, 500 mg of 7-ethyl-2-methyl-5-[[2'-(tetrazol-5-yl)biphenyl-4-yl]methyl]-5H-pyrazolo[1,5-b][1,2,4]triazole was obtained in the form of colorless crystals from 1.1 g of 7-ethyl-2-methyl-5-[[2'-(N-triphenylmethyl-tetrazol-5-yl)biphenyl-4-yl] methyl]-5H-pyrazolo[1,5-b][1,2,4]triazole.

(1) Melting point: 215°–216° C.

(2) Elemental analysis data (for $C_{21}H_{20}N_8 \cdot 0.1H_2O$)

|  | C (%) | H (%) | N (%) |
|---|---|---|---|
| calculated: | 65.30 | 5.27 | 29.01 |
| found: | 65.49 | 5.29 | 28.85 |

(3) Nuclear magnetic resonance spectrum (DMSO-$d_6$, TMS) δ (ppm):
1.21 (3H, t), 2.28 (3H, s), 2.51 (2H, q), 5.36 (2H, s), 7.06 (2H, d), 7.19 (2H, d)

(4) Mass spectrometric data (FAB): 385 (MH$^+$)

Example 54

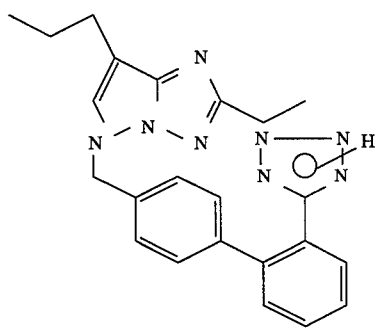

In the same manner as described in Example 12, 660 mg of 2-ethyl-7-n-propyl-5-[[2'-(tetrazol-5-yl)biphenyl-4-yl]methyl]-5H-pyrazolo[1,5-b][1,2,4]triazole was obtained in the form of colorless crystals from 1.5 g of 2-ethyl-7-n-propyl-5-[[2'-(N-triphenylmethyl-tetrazol-5-yl)biphenyl-4-yl] methyl]-5H-pyrazolo[1,5-b][1,2,4]triazole.

(1) Melting point: 134°–136° C.

(2) Elemental analysis data (for $C_{23}H_{24}N_8 \cdot 0.3H_2O$)

|  | C (%) | H (%) | N (%) |
|---|---|---|---|
| calculated: | 66.10 | 5.93 | 26.81 |
| found: | 66.10 | 5.84 | 26.59 |

(3) Nuclear magnetic resonance spectrum (DMSO-$d_6$, TMS) δ (ppm):
0.90 (3H, t), 1.21 (3H, t), 1.60–1.66 (2H, m), 2.47 (2H, t), 2.63 (2H, q), 5.35 (2H, s), 7.06 (2H, d), 7.18 (2H, d)

(4) Mass spectrometric data (FAB): 413 (MH$^+$)

Example 55

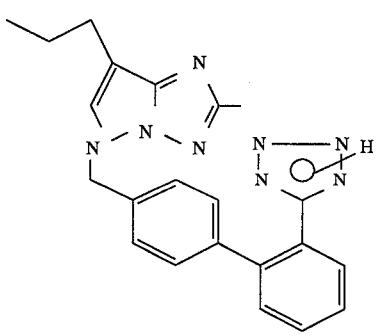

In the same manner as described in Example 12, 270 mg of 2-methyl-7-n-propyl-5-[[2'-(tetrazol-5-yl)biphenyl- 4-yl] methyl]-5H-pyrazolo[1,5-b][1,2,4]triazole was obtained in the form of colorless crystals from 1.7 g of 2-methyl-7-n-propyl- 5-[[2'-(N-triphenylmethyl-tetrazol-5-yl)biphenyl-4-yl] methyl]-5H-pyrazolo[1,5-b][1,2,4]triazole.

(1) Melting point: 124°–126° C.

(2) Elemental analysis data (for $C_{22}H_{22}N_8 \cdot 1H_2O$)

|  | C (%) | H (%) | N (%) |
| --- | --- | --- | --- |
| calculated: | 63.45 | 5.81 | 26.90 |
| found: | 63.28 | 5.37 | 26.89 |

(3) Nuclear magnetic resonance spectrum (DMSO-$d_6$, TMS) δ (ppm):
0.89 (3H, t), 1.63 (2H, m), 2.28 (3H, s), 2.46 (2H, t), 5.35 (2H, s), 7.06 (2H, d), 7.17 (2H, d)

(4) Mass spectrometric data (FAB): 399 (MH$^+$)

Example 56

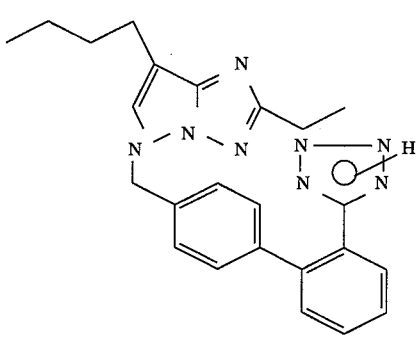

In the same manner as described in Example 12, 170 mg of 7-n-butyl-2-ethyl-5-[[2'-(tetrazol-5-yl)biphenyl-4-yl] methyl]-5H-pyrazolo[1,5-b][1,2,4]triazole was obtained in the form of colorless crystals from 440 mg of 7-n-butyl-2 -ethyl-5-[[2'-(N-triphenylmethyl-tetrazol-5-yl)biphenyl-4-yl] methyl]-5H-pyrazolo[1,5-b][1,2,4]triazole.

(1) Melting point: 137°–139° C.

(2) Elemental analysis data (for $C_{24}H_{26}N_8 \cdot 0.1H_2O$)

|  | C (%) | H (%) | N (%) |
| --- | --- | --- | --- |
| calculated: | 67.30 | 6.17 | 26.16 |
| found: | 67.26 | 6.01 | 26.15 |

(3) Nuclear magnetic resonance spectrum (DMSO-$d_6$, TMS) δ (ppm):
0.89 (3H, t), 1.21 (3H, t), 1.31 (2H, m), 1.60 (2H, m), 2.49 (2H, t), 2.64 (2H, q), 5.35 (2H, s), 7.06 (2H, d), 7.18 (2H, d)

(4) Mass spectrometric data (FAB): 427 (MH$^+$)

Example 57

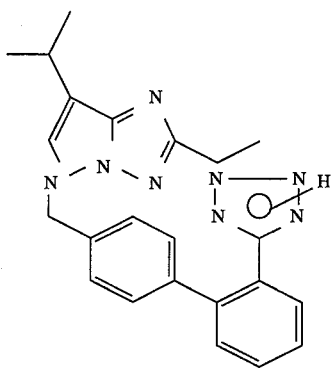

In the same manner as described in Example 12, 640 mg of 2-ethyl-7-isopropyl-5-[[2'-(tetrazol-5-yl)biphenyl- 4-yl] methyl]-5H-pyrazolo[1,5-b][1,2,4]triazole was obtained in the form of colorless crystals from 1.2 g of 2-ethyl-7 -isopropyl-5-[[2'-(N-triphenylmethyl-tetrazol-5-yl)biphenyl-4-yl] methyl]-5H-pyrazolo[1,5-b][1,2,4]triazole.

(1) Melting point: 143°–145° C.

(2) Elemental analysis data (for $C_{23}H_{24}N_8 \cdot 0.2CH_3CO_2C_2H_5$)

|  | C (%) | H (%) | N (%) |
| --- | --- | --- | --- |
| calculated: | 66.46 | 6.00 | 26.05 |
| found: | 66.65 | 5.97 | 25.87 |

(3) Nuclear magnetic resonance spectrum (DMSO-$d_6$, TMS) δ (ppm):
1.20–1.26 (9H, m), 2.64 (2H, q), 2.89 (2H, m), 5.35 (2H, s), 7.07 (2H, d), 7.20 (2H, d)

(4) Mass spectrometric data (FAB): 413 (MH$^+$)

Example 58

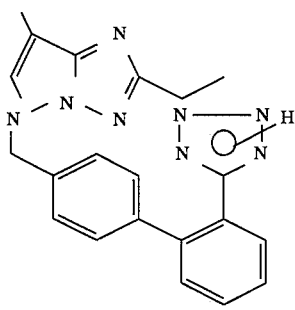

In the same manner as described in Example 12, 700 mg of 2-ethyl-7-methyl-5-[[2'-(tetrazol-5-yl)biphenyl-4-yl]methyl]-5H-pyrazolo[1,5-b][1,2,4]triazole was obtained in the form of colorless crystals from 1.5 g of 2-ethyl-7-methyl-5-[[2'-(N-triphenylmethyl-tetrazol-5-yl)biphenyl-4-yl] methyl]-5H-pyrazolo[1,5-b][1,2,4]triazole (compound 44a).

(1) Melting point: 178°–180° C.

(2) Elemental analysis data (for $C_{21}H_{20}N_8 \cdot 0.1H_2O$)

|  | C (%) | H (%) | N (%) |
|---|---|---|---|
| calculated: | 65.55 | 5.25 | 29.01 |
| found: | 65.15 | 5.34 | 29.12 |

(3) Nuclear magnetic resonance spectrum (DMSO-$d_6$, TMS) δ (ppm):
1.22 (3H, t), 2.09 (3H, s), 2.64 (2H, q), 5.35 (2H, s), 7.06 (2H, d), 7.19 (2H, d)

(4) Mass spectrometric data (FAB): 385 (MH$^+$)

Example 59

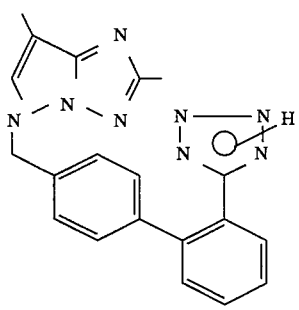

In the same manner as described in Example 12, 650 mg of 2,7-dimethyl-5-[[2'-(tetrazol-5-yl)biphenyl-4-yl] methyl]-5H-pyrazolo[1,5-b][1,2,4]triazole was obtained in the form of colorless crystals from 1.3 g of 2,7-dimethyl-5-[[2'-(N-triphenylmethyl-tetrazol-5-yl)biphenyl-4-yl]methyl]-5H-pyrazolo[1,5-b][1,2,4]triazole (compound 45a).

(1) Melting point: 261°–265° C.

(2) Elemental analysis data (for $C_{20}H_{18}N_8 \cdot 0.5H_2O$)

|  | C (%) | H (%) | N (%) |
|---|---|---|---|
| calculated: | 63.31 | 5.05 | 29.53 |
| found: | 63.67 | 5.13 | 29.14 |

(3) Nuclear magnetic resonance spectrum (DMSO-$d_6$, TMS) δ (ppm):
2.08 (3H, s), 2.28 (3H, s), 5.35 (2H, s), 7.06 (2H, d), 7.17 (2H, d)

(4) Mass spectrometric data (FAB): 371 (MH$^+$)

Example 60

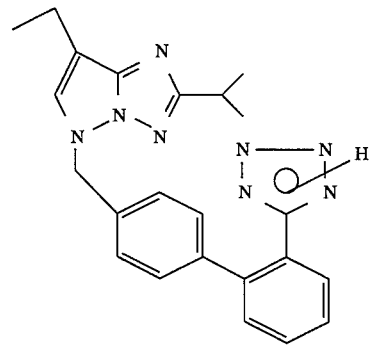

A mixture consisting of 2.38 g of 7-ethyl-2-isopropyl-5-[[2'-(N-triphenylmethyl-tetrazol-5-yl)biphenyl-4-yl]methyl]-5H-pyrazolo[1,5-b][1,2,4]triazole, 90 ml of methanol and 10 ml of acetic acid was heated under reflux for 2 hours. After removing the solvent by distillation under a reduced pressure, the thus obtained residue was subjected to silica gel column chromatography. Elution with methanol-chloroform (1:9, v/v) gave 1.43 g of 7-ethyl-2-isopropyl-5-[[2'-(tetrazol-5-yl)biphenyl-4-yl]methyl]-5H-pyrazolo[1,5-b][1,2,4]triazole in the form of colorless amorphous foamy material.

(1) Nuclear magnetic resonance spectrum (DMSO-$d_6$, TMS) δ (ppm):
1.21 (3H, t), 1.25 (6H, d), 2.96 (1H, m), 5.35 (2H, s), 7.07 (2H, d), 7.21 (2H, d)

(2) Mass spectrometric data (FAB): 413 (MH$^+$)

Example 61

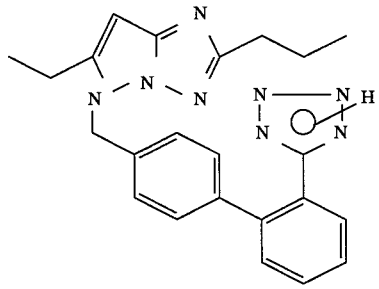

In the same manner as described in Example 12, 1.19 g of 6-ethyl-2-propyl-5-[[2'-(tetrazol-5-yl)biphenyl-4-yl]methyl]-5H-pyrazolo[1,5-b][1,2,4]triazole was obtained in the form of colorless crystals from 2.14 g of 6-ethyl-2-propyl-5-[[2'-(N-triphenylmethyl-tetrazol-5-yl)biphenyl-4-yl] methyl]-5H-pyrazolo[1,5-b][1,2,4]triazole (compound 47d).

(1) Melting point: 191°–193° C.

(2) Elemental analysis data (for $C_{23}H_{24}N_8$)

|  | C (%) | H (%) | N (%) |
|---|---|---|---|
| calculated: | 66.97 | 5.86 | 27.16 |
| found: | 66.97 | 5.92 | 26.98 |

(3) Nuclear magnetic resonance spectrum (DMSO-$d_6$, TMS) δ (ppm):

0.90 (3H, t), 1.21 (3H, t), 1.67 (2H, m) ! 2.58 (2H, t), 2.72 (2H, q), 5.48 (2H, s), 6.06 (1H, s), 7.05 (2H, d), 7.08 (2H, d)

(4) Mass spectrometric data (FAB): 413 (MH$^+$)

Example 62

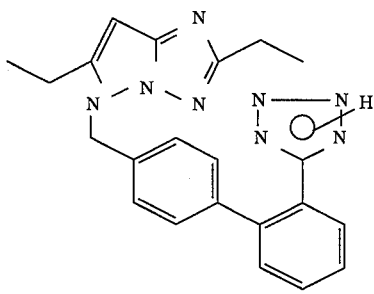

In the same manner as described in Example 12, 1.03 g of 2,6-diethyl-5-[[2'-(tetrazol-5-yl)biphenyl-4-yl] methyl]-5H-pyrazolo[1,5-b][1,2,4]triazole was obtained in the form of colorless crystals from 1.95 g of 2,6-diethyl-5 -[[2'-(N-triphenylmethyl-tetrazol-5-yl)biphenyl-4-yl]methyl] -5H-pyrazolo[1,5-b][1,2,4]triazole (compound 48d).

(1) Melting point: 180°–182° C.

(2) Elemental analysis data (for $C_{22}H_{22}N_8 \cdot 0.2H_2O$)

|  | C (%) | H (%) | N (%) |
|---|---|---|---|
| calculated: | 65.92 | 5.62 | 27.87 |
| found: | 65.68 | 5.48 | 27.80 |

(3) Nuclear magnetic resonance spectrum (DMSO-$d_6$, TMS) δ (ppm):

1.21 (3H, t), 1.22 (3H, t), 2.64 (2H, q), 2.72 (2H, q), 5.49 (2H, s), 6.06 (1H, s), 7.06 (2H, d), 7.09 (2H, d)

(4) Mass spectrometric data (FAB): 399 (MH$^+$)

Example 63

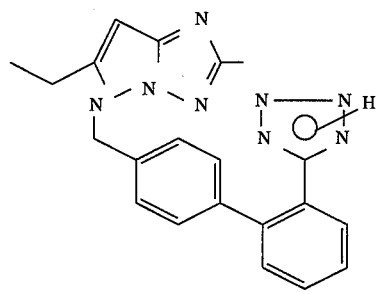

In the same manner as described in Example 12, 0.67 g of 6-ethyl-2-methyl-5-[[2'-(tetrazol-5-yl)biphenyl-4-yl] methyl]-5H-pyrazolo[1,5-b][1,2,4]triazole was obtained in the form of colorless crystals from 1.66 g of 6-ethyl-2 -methyl-5-[[2'-(N-triphenylmethyl-tetrazol-5-yl)biphenyl-4-yl] methyl]-5H-pyrazolo[1,5-b][1,2,4]triazole (compound 49d).

(1) Melting point: 217°–219° C. (decomposition)

(2) Elemental analysis data (for $C_{21}H_{20}N_8 \cdot 0.4\ H_2O$)

|  | C (%) | H (%) | N (%) |
|---|---|---|---|
| calculated: | 64.40 | 5.35 | 28.61 |
| found: | 64.56 | 5.28 | 28.16 |

(3) Nuclear magnetic resonance spectrum (DMSO-$d_6$, TMS) δ (ppm):

1.21 (3H, t), 2.28 (3H, s), 2.72 (2H, q), 5.47 (2H, s), 6.05 (1H, s), 7.06 (4H, s)

(4) Mass spectrometric data (FAB): 385 (MH$^+$)

Example 64

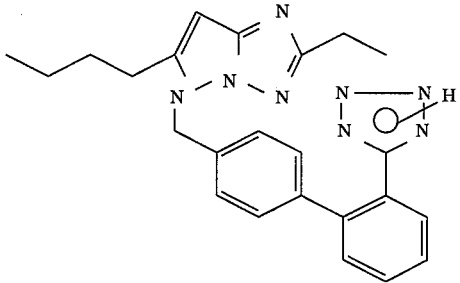

In the same manner as described in Example 12, 1.04 g of 6-butyl-2-ethyl-5-[[2'-(tetrazol-5-yl)biphenyl-4 -yl]methyl]-5H-pyrazolo[1,5-b][1,2,4]triazole was obtained in the form of colorless crystals from 2.00 g of a mixture consisting (about 1:8) of 6-butyl-2-ethyl-7-[[2'-(N-triphenylmethyl-tetrazol- 5-yl)biphenyl-4-yl]methyl]-1H-pyrazolo[ 1,5-b][1,2, 4]triazole (compound 50c) and 6-butyl-2 -ethyl-5-[[2'-(N-triphenylmethyl-tetrazol-5-yl)biphenyl-4-yl] methyl]-5H-pyrazolo[1,5-b][1,2,4]triazole (compound 50d).

(1) Melting point: 183°–184.5° C.

(2) Elemental analysis data (for $C_{24}H_{26}N_8$)

|  | C (%) | H (%) | N (%) |
|---|---|---|---|
| calculated: | 67.58 | 6.14 | 26.27 |
| found: | 67.52 | 6.10 | 26.15 |

(3) Nuclear magnetic resonance spectrum (DMSO-$d_6$, TMS) δ (ppm):
0.88 (3H, t), 1.21 (3H, t), 1.35 (2H, m), 1.57 (2H, m), 2.63 (2H, q), 2.70 (2H, t), 5.49 (2H, s), 6.06 (1H, s), 7.07 (4H, s)

(4) Mass spectrometric data (FAB): 427 (MH$^+$)

Example 65

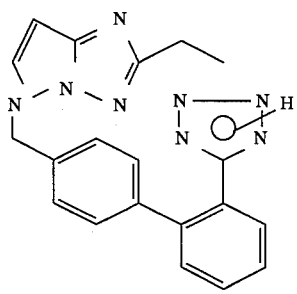

In the same manner as described in Example 12, 83 mg of 2-ethyl-5-[[2'-(tetrazol-5-yl)biphenyl-4-yl]methyl] -5H-pyrazolo[1,5-b][1,2,4]triazole was obtained in the form of colorless crystals from 200 mg of 2-ethyl-5-[[2'-(N-triphenylmethyl-tetrazol- 5-yl)biphenyl-4-yl]methyl]-5H-pyrazolo[ 1,5-b][1,2,4]triazole (compound 51b).

(1) Melting point: 180°–183° C. (decomposition)
(2) Elemental analysis data (for $C_{20}H_{18}N_8.0.1$ $CH_3COOCH_2CH_3$)

|  | C (%) | H (%) | N (%) |
|---|---|---|---|
| calculated: | 64.61 | 5.00 | 29.55 |
| found: | 64.19 | 5.03 | 29.33 |

(3) Nuclear magnetic resonance spectrum (DMSO-$d_6$, TMS) δ (ppm):
1.31 (3H, t), 2.74 (2H, q), 5.46 (2H, s), 6.10 (1H, d), 7.10 (2H, d), 7.26 (2H, d), 7.72 (1H, d)

(4) Mass spectrometric data (FAB): 371 (MH$^+$)

Reference Example 25 (Starting compound for use in Example 66)

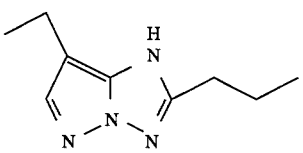

(A) A 3.97 g portion of 3-amino-4-ethyl-1H-pyrazole was dissolved in 60 ml of acetonitrile and, with cooling on an ice bath, 6.12 g of ethyl butylimidate hydrochloride was added to the solution. The thus prepared mixture was stirred for 1 hour at the same temperature and then overnight at room temperature.

The thus formed solid material was collected by filtration and dissolved in a methanol-chloroform (1:4, v/v) mixed solvent. Thereafter, insoluble materials were removed by filtration, the resulting filtrate was concentrated under a reduced pressure and then the thus obtained residue was subjected to silica gel column chromatography. Elution with methanol-chloroform (1:9–1:4, v/v) gave 3.27 g of N-(4-ethyl-1H-pyrazol-3-yl)butylamidine hydrochloride.

(1) Nuclear magnetic resonance spectrum (DMSO-$d_6$, TMS) δ (ppm):
0.97 (3H, t), 1.12 (3H, t), 1.77 (2H, m), 2.44–2.86 (4H, m), 7.68 (1H, s)

(2) Mass spectrometric data (EI): 180 (M$^+$)

(B) A 0.39 g portion of sodium was added to 15 ml of methanol to prepare a sodium methoxide solution. A 1.18 g portion of hydroxylamine hydrochloride was added to the above solution and the thus formed sodium chloride was removed by filtration to prepare a methanol solution of hydroxylamine. On the other hand, 3.18 g of N-(4-ethyl-1H-pyrazol-3-yl)butylamidine hydrochloride was dissolved in 20 ml of methanol and cooled on an ice bath.

To this was added dropwise the methanol solution of hydroxylamine prepared above, followed by overnight stirring at room temperature. The reaction mixture was concentrated under a reduced pressure, and the thus obtained residue was subjected to silica gel column chromatography. Elution with methanol-chloroform (1:9, v/v) gave 2.47 g of N-(4-ethyl-1 H-pyrazol-3-yl)butylamidoxime.

(1) Nuclear magnetic resonance spectrum (DMSO-$d_6$, TMS) δ (ppm):
0.77 (3H, t), 1.09 (3H, t), 2.18 (2H, t), 2.30 (2H, q), 7.40 (1H, s)

(2) Mass spectrometric data (EI): 196 (M$^+$)

(C) A 2.45 g portion of N-(4-ethyl-1H-pyrazol-3-yl)butylamidoxime was dissolved in 20 ml of N,N-dimethylacetamide. With cooling on an ice bath, to this were added 1.01 ml of pyridine and 2.38 g of p-toluenesulfonic acid chloride, followed by 30 minutes of stirring at the same temperature and additional 2 hours of stirring at room temperature.

The resulting reaction mixture was added to 100 ml of water and extracted with chloroform. After distilling off chloroform from the organic layer under a reduced pressure, the thus obtained residue was dissolved in 60 ml of methanol, mixed with 1.01 ml of pyridine and then heated under reflux for 2 hours.

Thereafter, the reaction mixture was concentrated under a reduced pressure, and the resulting residue was subjected to silica gel column chromatography. Elution with methanol-chloroform (3:97, v/v) gave 1.14 g of 7-ethyl-2 -propyl-1H-pyrazolo[1,5-b][1,2,4]triazole.

(1) Nuclear magnetic resonance spectrum (DMSO-$d_6$, TMS) δ (ppm):
0.95 (3H, t), 1.20 (3H, t), 1.74 (2H, m), 2.50 (2H, q), 2.70 (2H, t), 7.21 (1H, s), 12.33 (1H, brs)

(2) Mass spectrometric data (EI): 178 (M$^+$)

Reference Example 26 (Starting compound for use in Example 67)

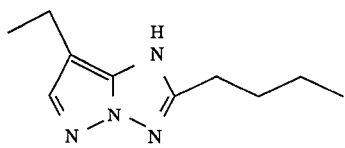

(A) A 4.92 g portion of 3-amino-4-ethyl-1H-pyrazole was dissolved in 25 ml of acetonitrile and, with cooling on an ice bath, 8.30 g of ethyl valerimidate hydrochloride was added to the solution. The thus prepared mixture was stirred for 1 hour at the same temperature and then overnight at room temperature.

Thereafter, the thus formed insoluble materials were removed by filtration, the resulting filtrate was concentrated under a reduced pressure and then the thus obtained residue was subjected to silica gel column chromatography. Elution with methanol-chloroform (1:9–1:4, v/v) gave 6.26 g of N-(4-ethyl-1H-pyrazol-3-yl)valeramidine hydrochloride.

(1) Nuclear magnetic resonance spectrum (DMSO-$d_6$, TMS) δ (ppm):
0.92 (3H, t), 1.12 (3H, t), 2.43–2.87 (4H, m), 7.69 (1H, s)

(2) Mass spectrometric data (EI): 194 ($M^+$)

(B) In the same manner as described in the step (B) of Reference Example 25, 2.84 g of N-(4-ethyl-1H-pyrazol-3-yl)valeramidoxime was obtained from 6.14 g of N-(4-ethyl-1H-pyrazol-3-yl)valeramidine hydrochloride.

(1) Nuclear magnetic resonance spectrum (DMSO-$d_6$, TMS) δ (ppm):
0.76 (3H, t), 2.12–2.43 (4H, m), 7.40 (1H, s)

(2) Mass spectrometric data (EI): 210 ($M^+$)

(C) In the same manner as the procedure of the step (C) of Reference Example 25, 0.97 g of 2-butyl-7-ethyl-1H-pyrazolo[1,5-b][1,2,4]triazole was obtained from 2.78 g of N-(4-ethyl-1H-pyrazol-3-yl)valeramidoxime.

(1) Nuclear magnetic resonance spectrum (DMSO-$d_6$, TMS) δ (ppm):
0.92 (3H, t), 1.20 (3H, t), 2.50 (2H, q), 2.72 (2H, t), 7.21 (1H, s), 12.34 (1H, brs)

(2) Mass spectrometric data (EI): 192 ($M^+$)

Reference Example 27 (Starting compound for use in Example 68)

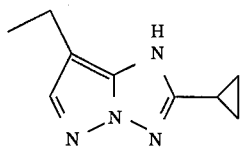

(A) A 15.1 g portion of 3-amino-4-ethyl-1H-pyrazole was dissolved in 80 ml of acetonitrile and, with cooling on an ice bath, 23.2 g of ethyl cyclopropanecarboxyimidate hydrochloride was added to the solution. The thus prepared mixture was stirred for 1 hour at the same temperature and then overnight at room temperature.

The thus formed solid material was collected by filtration and dissolved in a methanol-chloroform (1:4, v/v) mixed solvent. Thereafter, insoluble materials were removed by filtration and the resulting filtrate was concentrated under a reduced pressure to give 13.6 g of N-(4-ethyl-1H-pyrazol-3-yl)cyclopropanecarboxyamidine hydrochloride.

(1) Nuclear magnetic resonance spectrum (DMSO-$d_6$, TMS) δ (ppm):
1.04–1.36 (7H, m), 2.42–2.67 (3H, m), 7.70 (1H, s)

(2) Mass spectrometric data (EI): 178 ($M^+$)

(B) In the same manner as described in the step (B) of Reference Example 25, 12.1 g of N-(4-ethyl-1H-pyrazol-3-yl)cyclopropanecarboxyamidoxime was obtained from 15.2 g of N-(4-ethyl-1H-pyrazol-3-yl)cyclopropanecarboxyamidine hydrochloride.

(1) Nuclear magnetic resonance spectrum (DMSO-$d_6$, TMS) δ (ppm):
0.43–0.65 (4H, m), 1.11 (3H, t), 1.47 (1H, brm), 2.33 (2H, q), 7.42 (1H, s)

(2) Mass spectrometric data (EI): 194 ($M^+$)

(C) In the same manner as the procedure of the step (C) of Reference Example 25, 1.5 g of 2-cyclopropyl-7-ethyl-1H-pyrazolo[1,5-b][1,2,4]triazole was obtained from 17.9 g of N-(4-ethyl-1H-pyrazol-3-yl)cyclopropanecarboxyamidoxime.

(1) Nuclear magnetic resonance spectrum (DMSO-$d_6$, TMS) δ (ppm):
0.92–1.27 (7H, m), 2.03 (1H, m), 2.48 (2H, q), 7.19 (1H, s), 12.30 (1H, brs)

(2) Mass spectrometric data (EI): 176 ($M^+$)

Reference Example 28 (Starting compound for use in Example 69)

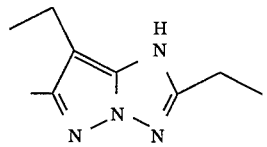

(A) A one liter capacity three neck flask was cooled using a dry ice-methanol mixture and then charged with about 300 ml of liquid ammonia. With mechanical vigorous agitation, 13.2 g of sodium amide was added at once and, after 5 minutes thereof, 29.6 ml of butyronitrile was added dropwise spending 5 minutes, followed by 5 minutes of reaction. To this was added dropwise 16.6 ml of ethyl acetate spending 5 minutes, followed by 1 hour of reaction at the same temperature. In a stream of argon, the reaction vessel was heated on a water bath of about 40° C. to distill off ammonia.

To the thus obtained white solid material were added 30 ml of ether and 100 ml of ice water, followed by neutralization of the resulting mixture with 6N hydrochloric acid aqueous solution. The resulting organic layer was collected and mixed with 50 ml of ethanol and 16.9 ml of hydrazine monohydrate. Ether was removed from the mixture by distillation under normal pressure and then the thus obtained ethanol solution was heated overnight under reflux.

The reaction solution was concentrated under a reduced pressure, and the resulting residue was subjected to silica gel column chromatography. Elution with methanol-chloroform (1:24, v/v) gave 12.2 g of 3-amino-4-ethyl-5-methyl-1H-pyrazole in the form of oily material.

(1) Nuclear magnetic resonance spectrum (CDCl$_3$-$d_6$, TMS) δ (ppm):

1.08 (3H, t), 2.13 (3H, s), 2.30 (2H, q), 5.53 (3H, brs)

(2) Mass spectrometric data (EI): 125 (M⁺)

(B) A 1.16 g portion of sodium was added to 50 ml of methanol to prepare a sodium mathoxide solution. A 3.50 g portion of hydroxylamine hydrochloride was added to the above solution and the thus formed sodium chloride was removed by filtration to prepare a methanol solution of hydroxylamine.

On the other hand, a mixture consisting of 6.00 g of 3-amino-4-ethyl-5-methyl-1H-pyrazole, 60 ml of toluene and 9.64 ml of triethyl orthopropionate was heated overnight under reflux, and the solvent was removed by distillation under a reduced pressure. The resulting residue was dissolved in 60 ml of methanol. With cooling on an ice bath, to this was added dropwise the methanol solution of hydroxylamine prepared above, followed by overnight stirring at room temperature.

The reaction mixture was concentrated under a reduced pressure, and the thus obtained residue was subjected to silica gel column chromatography. Elution with methanol-chloroform (1:9, v/v) gave 3.78 g of N-(4-ethyl-5-methyl-1 H-pyrazol-3-yl)propionamidoxime.

(1) Nuclear magnetic resonance spectrum (DMSO-$d_6$, TMS) δ (ppm):
0.88 (3H, t), 1.00 (3H, t), 2.00–2.39 (7H, m)

(2) Mass spectrometric data (EI): 196 (M⁺)

(C) In the same manner as the procedure of the step (C) of Reference Example 25, 1.27 g of 2,7-diethyl-6 -methyl-1H-pyrazolo[1,5-b][1,2,4]triazole was obtained from 3.74 g of N-(4-ethyl-5-methyl-1H-pyrazol-3-yl)propionamidoxime.

(1) Nuclear magnetic resonance spectrum (DMSO-$d_6$, TMS) δ (ppm):
1.16 (3H, t), 1.26 (3H, t), 2.15 (3H, s), 2.44 (2H, q), 2.71 (2H, q), 12.12 (1H, brs)

(2) Mass spectrometric data (EI): 178 (M⁺)

Reference Example 29 (Starting compound for use in Example 70)

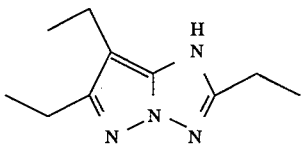

(A) In the same manner as described in the step (A) of Reference Example 28, 15.5 g of 3-amino-4-diethyl-1 H-pyrazole was obtained in the form of colorless solid from 26.6 ml of butyronitrile and 14.6 ml of methyl propionate.

(1) Nuclear magnetic resonance spectrum (CDCl₃, TMS) δ (ppm):
1.09 (3H, t), 1.20 (3H, t), 2.32 (2H, q), 2.54 (2H, q), 5.29 (3H, brs)

(2) Mass spectrometric data (EI): 139 (M⁺)

(B) N-(4,5-Diethyl-1H-pyrazol-3-yl)propionamidine hydrochloride intermediate obtained in the same manner as described in the step (A) of Reference Example 26 from 5.09 g of 3-amino-4,5-diethyl-1H-pyrazole was treated in the same manner as the step (B) of Reference Example 25 to give 4.53 of N-(4,5-diethyl-1H-pyrazol-3-yl)propionamidoxime.

(1) Nuclear magnetic resonance spectrum (DMSO-$d_6$, TMS) δ (ppm):
0.89 (3H, t), 1.01 (3H, t), 1.15 (3H, t), 2.10–2.64 (6H, m)

(2) Mass spectrometric data (EI): 210 (M⁺)

(C) In the same manner as the procedure of the step (C) of Reference Example 25, 2.25 g of 2,6,7-triethyl- 1H-pyrazolo[1,5-b][1,2,4]triazole was obtained from 4.41 g of N-(4, 5-diethyl-1H-pyrazol-3-yl)propionamidoxime.

(1) Nuclear magnetic resonance spectrum (DMSO-$d_6$, TMS) δ (ppm):
1.17 (3H, t), 1.18 (3H, t), 1.27 (3H, t), 2.33–2.85 (6H, m), 12.16 (1H, brs)

(2) Mass spectrometric data (EI): 192 (M⁺)

Reference Example 30 (Starting compound for use in Example 71)

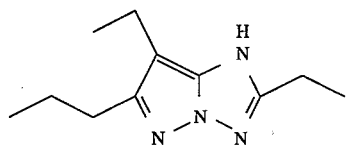

(A) In the same manner as described in the step (A) of Reference Example 28, 17.7 g of 3-amino-4-ethyl-5 -propyl-1H-pyrazole was obtained in the form of colorless solid from 32.5 ml of butyronitrile and 21.1 ml of methyl butanoate.

(1) Nuclear magnetic resonance spectrum (CDCl₃, TMS) δ (ppm):
0.94 (3H, t), 1.09 (3H, t), 1.60 (2H, m), 2.32 (2H, q), 2.49 (2H, t), 5.29 (3H, brs)

(2) Mass spectrometric data (EI): 153 (M⁺)

(B) In the same manner as described in the step (B) of Reference Example 28, 3.91 g of N-(4-ethyl-5-propyl-1H-pyrazol-3-yl)propionamidoxime was obtained from 6.02 g of 3-amino-4-ethyl-5-propyl-1H-pyrazole.

(1) Nuclear magnetic resonance spectrum (DMSO-$d_6$, TMS) δ (ppm):
0.87 (6H, t), 1.00 (3H, t), 1.55 (2H, m) , 2.09–2.55 (6H, m)

(2) Mass spectrometric data (EI): 224 (M⁺)

(C) In the same manner as the procedure of the step (C) of Reference Example 25, 0.97 g of 2,7-diethyl-6 -propyl-1H-pyrazolo[1,5-b][1,2,4]triazole was obtained from 3.89 g of N-(4-ethyl-5-propyl-1H-pyrazol-3-yl)propionamidoxime.

(1) Nuclear magnetic resonance spectrum (DMSO-$d_6$, TMS) δ (ppm):
0.90 (3H, t), 1.16 (3H, t), 1.26 (3H, t), 1.57 (2H, m), 2.32–2.84 (6H, m), 12.11 (1H, brs)

(2) Mass spectrometric data (EI): 206 (M⁺)

Reference Example 31 (Starting compound for use in Example 72)

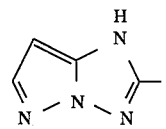

(A) N-(1H-Pyrazol-3-yl)acetamidine hydrochloride intermediate obtained in the same manner as described in the step (A) of Reference Example 25 from 11.0 g of 3-amino-1H-pyrazole was treated in the same manner as the step (B) of Reference Example 25 to give 5.50 g of N-(1H-pyrazol-3-yl)acetamidoxime.

(1) Nuclear magnetic resonance spectrum (CDCl$_3$, TMS) δ (ppm):
1.94 (3H, s), 5.96 (1H, d), 7.54 (1H, d)

(2) Mass spectrometric data (EI): 140 (M$^+$)

(B) In the same manner as described in the step (C) of Reference Example 25, 1.42 g of 2-methyl-1H-pyrazolo[1,5-b][1,2,4]triazole was obtained from 5.28 g of N-(1H-pyrazol-3-yl)acetamidoxime.

(1) Nuclear magnetic resonance spectrum (DMSO-d$_6$, TMS) δ (ppm):
2.40 (3H, s), 5.72 (1H, d), 7.38 (1H, d), 12.41 (1H, brs)

(2) Mass spectrometric data (EI): 122 (M$^+$)

Reference Example 32 (Starting compound for use in Example 73)

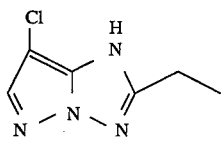

A 1.50 g portion of 2-ethyl-1H-pyrazolo[1,5-b][1,2,4]triazole was dissolved in a mixed solvent consisting of 75 ml of tetrahydrofuran and 150 ml of dichloromethane. This solution was mixed with 1.61 g of N-chlorosuccinimide and stirred for 30 minutes at room temperature, and the reaction mixture was washed twice with sodium bicarbonate aqueous solution and then once with water.

The organic layer was dried over anhydrous magnesium sulfate and the solvent was removed by distillation under a reduced pressure. Thereafter, the thus formed crystals were dispersed in diisopropyl ether and collected by filtration to give 1.34 g of 7-chloro-2-ethyl-1H-pyrazolo[1,5-b][1,2,4]triazole.

(1) Nuclear magnetic resonance spectrum (DMSO-d$_6$, TMS) δ (ppm):
1.29 (3H, t), 2.78 (2H, q), 7.49 (1H, s), 13.06 (1H, brs)

(2) Mass spectrometric data (EI): 170 (M$^+$)

Reference Example 33 (Starting compound for use in Example 74)

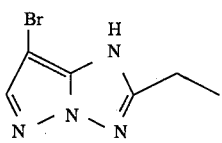

In the same manner as the procedure of Reference Example 32, 2.30 g of 7-bromo-2-ethyl-1H-pyrazolo[1,5-b][1,2,4]triazole was obtained from 2.52 g of 2-ethyl-1H-pyrazolo[1,5-b][1,2,4]triazole and 3.30 g of N-bromosuccinimide.

(1) Nuclear magnetic resonance spectrum (DMSO-d$_6$, TMS) δ (ppm):

1.29 (3H, t), 2.79 (2H, q), 7.50 (1H, s), 13.03 (1H, brs), (2) Mass spectrometric data (EI): 214 (M$^+$)

Reference Example 34 (Starting compound for use in Example 75)

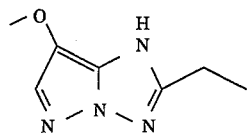

(A) A mixture consisting of 58.9 g of methoxyacetonitrile and one liter of ethyl formate was added, in a dropwise manner spending 1.5 hours, to 111.5 g of potassium t-butoxide which was cooled on an ice bath and stirred vigorously. After 3 hours of stirring at the same temperature, 600 ml of water was added to the reaction mixture. The resulting water layer was washed with 500 ml of ethyl acetate and then adjusted to pH 5.8 with 2N hydrochloric acid aqueous solution.

To this were added 250 ml of ethanol and 60 ml of hydrazine monohydrate (80% in purity), followed by overnight heating under reflux. The solvent was removed by distillation under a reduced pressure, and the resulting residue was mixed with 500 ml of a mixed solution of methanol and chloroform (1:9, v/v). Thereafter, insoluble materials were removed by filtration, the resulting filtrate was concentrated under a reduced pressure, and then the thus obtained residue was subjected to silica gel column chromatography. Elution with methanol-chloroform (3:47, v/v) gave 6.61 g of 3-amino-4-methoxy-1H-pyrazole in the form of grey solid.

(1) Nuclear magnetic resonance spectrum (DMSO-d$_6$, TMS) δ (ppm):
3.61 (3H, s), 4.17 (2H, brs), 7.16 (1H, s), 10.88 (1H, brs)

(2) Mass spectrometric data (EI): 113 (M$^+$)

(B) In the same manner as described in the step (B) of Reference Example 28, 8.61 g of N-(4-methoxy-1 H-pyrazol-3-yl)propionamidoxime was obtained from 7.92 g of 3-amino-4-methoxy-1H-pyrazole.

(1) Nuclear magnetic resonance spectrum (DMSO-d$_6$, TMS) δ (ppm):
0.91 (3H, t), 2.22 (2H, q), 3.68 (3H, s), 7.44 (1H, s)

(2) Mass spectrometric data (FAB): 185 (MH$^+$)

(C) In the same manner as the procedure of the step (C) of Reference Example 25, 0.85 g of 2-ethyl-7-methoxy-1H-pyrazolo[1,5-b][1,2,4]triazole was obtained from 8.48 g of N-(4-methoxy-1H-pyrazol-3-yl)propionamidoxime.

(1) Nuclear magnetic resonance spectrum (DMSO-d$_6$, TMS) δ (ppm):
1.27 (3H, t), 2.73 (2H, q), 3.75 (3H, s), 7.22 (1H, s), 12.54 (1H, brs)

(2) Mass spectrometric data (EI): 166 (M$^+$)

Reference Example 35 (Starting compound for use in Example 76)

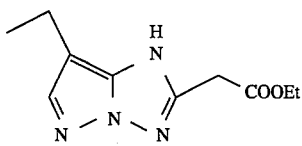

(A) In the same manner as described in the step (A) of Reference Example 26, 6.53 g of ethyl N-(4-ethyl-1 H-pyrazol-3-yl)-3-amino-3-imino-propanoate hydrochloride was obtained from 5.06 g of 3-amino-4-ethyl-1H-pyrazole and 9.80 g of ethyl 3-ethoxy-3-imino-propanoate hydrochloride.

(1) Nuclear magnetic resonance spectrum (DMSO-$d_6$, TMS) δ (ppm):
1.13 (3H, t), 1.23 (3H, t), 2.56 (2H, q), 4.12 (2H, s), 4.18 (2H, q), 7.72 (1H, s)

(2) Mass spectrometric data (EI): 224 ($M^+$)

(B) In the same manner as described in the step (B) of Reference Example 25, 3.31 g of ethyl N-hydroxy-N'-(4-ethyl-1H-pyrazol-3-yl)-3-amino-3-imino-propanoate was obtained from 6.44 g of ethyl N-(4-ethyl-1H-pyrazol-3-yl)-3-amino-3-imino-propanoate hydrochloride.

(1) Nuclear magnetic resonance spectrum (DMSO-$d_6$, TMS) δ (ppm):
1.05 (3H, t), 1.09 (3H, t), 2.29 (2H, q), 3.31 (2H, s), 3.90 (2H, q), 7.36 (1H, s)

(2) Mass spectrometric data (EI): 240 ($M^+$)

(C) In the same manner as the procedure of the step (C) of Reference Example 25, 1.44 g of ethyl [7-ethyl-1H-pyrazolo[1,5-b][1,2,4]triazole-2-yl]acetate was obtained from 3.26 g of ethyl N-hydroxy-N'-(4-ethyl-1H-pyrazol-3-yl)-3-amino-3-imino-propanoate.

(1) Nuclear magnetic resonance spectrum (DMSO-$d_6$, TMS) δ (ppm):
1.20 (3H, t), 1.22 (3H, t), 2.51 (2H, q), 3.93 (2H, s), 4.16 (2H, q), 7.27 (1H, s), 12.62 (1H, brs)

(2) Mass spectrometric data (EI): 222 ($M^+$)

Reference Example 36 (Starting compound for use in Example 77)

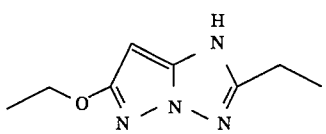

(A) In the same manner as described in the step (B) of Reference Example 28, 9.11 g of N-(5-ethoxy-1H-pyrazol-3-yl)propionamidoxime was obtained from 10.3 g of 3-amino-5-ethoxy-1H-pyrazole.

(1) Nuclear magnetic resonance spectrum (DMSO-$d_6$, TMS) δ (ppm):
0.94 (3H, t), 1.27 (3H, t), 2.11–2.39 (2H, m) 4.05 (2H, q), 5.35 (1H, s)

(2) Mass spectrometric data (EI): 198 ($M^+$)

(B) In the same manner as the procedure of the step (C) of Reference Example 25, 3.98 g of 6-ethoxy-2-ethyl-1H-pyrazolo[1,5-b][1,2,4]triazole was obtained from 9.04 g of N-(5-ethoxy-1H-pyrazol-3-yl)propionamidoxime.

(1) Nuclear magnetic resonance spectrum (DMSO-$d_6$, TMS) δ (ppm):
1.26 (3H, t), 1.29 (3H, t), 2.72 (2H, q), 4.11 (2H, q), 5.20 (1H, s), 12.30 (1H, brs)

(2) Mass spectrometric data (EI): 180 ($M^+$)

Reference Example 37 (Starting compound for use in Example 78)

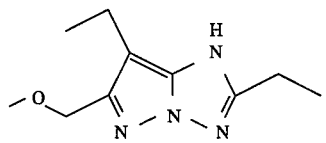

(A) In the same manner as described in the step (A) of Reference Example 28, 22.1 g of 3-amino-4-ethyl-5-methoxymethyl-1H-pyrazole was obtained from 17.5 g of n-butyronitrile and 26.3 g of methyl methoxy acetate.

(1) Nuclear magnetic resonance spectrum (CDCl$_3$, TMS) δ (ppm):
1.11 (3H, t), 2.36 (2H, t), 3.54 (3H, t), 4.41 (2H, s)

(2) Mass spectrometric data (EI): 155 ($M^+$)

(B) In the same manner as described in the step (B) of Reference Example 28, 12.3 g of N-(4-ethyl-5-methoxymethyl-1H-pyrazol-3-yl) propionamidoxime was obtained from 22 g of 3-amino-4-ethyl-5-methoxymethyl-1H-pyrazole.

(1) Nuclear magnetic resonance spectrum (DMSO-$d_6$, TMS) δ (ppm):
0.87 (3H, t), 1.02 (3H, t), 2.20 (2H, q), 2.33 (2H, q), 3.23 (3H, s), 3.33 (2H, s), 7.12 (1H, s), 9.40 (1H, s), 12.26 (1H, s)

(2) Mass spectrometric data (EI): 226 ($M^+$)

(C) In the same manner as the procedure of the step (C) of Reference Example 25, 1.2 g of 2,7-diethyl-6-methoxymethyl-1H-pyrazolo[1,5-b][1,2,4]triazole was obtained from 3.0 g of N-(4-ethyl-5-methoxymethyl-1H-pyrazol-3-yl)propionamidoxime.

(1) Nuclear magnetic resonance spectrum (DMSO-$d_6$, TMS) δ (ppm):
1.18 (3H, t), 1.28 (3H, t), 2.51 (2H, q), 2.74 (2H, q), 3.21 (3H, s), 4.34 (2H, s), 12.33 (1H, s)

(2) Mass spectrometric data (EI): 208 ($M^+$)

Reference Example 38 (Starting compound for use in Example 79)

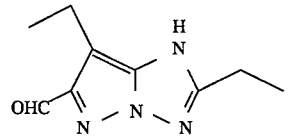

(A) In the same manner as described in the step (A) of Reference Example 28, 23.5 g of 3-amino-4-ethyl-5-diethoxymethyl-1H-pyrazole was obtained from 17 ml of n-butyronitrile and 25 ml of ethyl diethoxy acetate.

(1) Nuclear magnetic resonance spectrum (CDCl$_3$, TMS) δ (ppm):
1.10 (3H, t), 1.21 (6H, t), 2.40 (2H, q), 3.57 (4H, q), 5.61 (1H, s)

(2) Mass spectrometric data (EI): 213 (M⁺)

(B) In the same manner as described in the step (B) of Reference Example 28, 10.0 g of N-(4-ethyl-5-diethoxymethyl-1H-pyrazol-3-yl)propionamidoxime was obtained from 10.0 g of 3-amino-4-ethyl-5-diethoxymethyl-1H-pyrazole.

(1) Nuclear magnetic resonance spectrum (CDCl$_3$, TMS) δ (ppm):
1.04 (3H, t), 1.12 (3H, t), 1.24 (6H, t), 2.41– 2.48 (4H, m), 3.56–3.61 (4H, m), 5.67 (1H, s)

(2) Mass spectrometric data (FAB): 285 (MH⁺)

(C) In the same manner as the procedure of the step (C) of Reference Example 25, 1.3 g of 2,7-diethyl-1H-pyrazolo[1,5-b][1,2,4]triazole-6-carboxyaldehyde was obtained from 3.0 g of N-(4-ethyl-5-diethoxymethyl-1H-pyrazol-3-yl)propionamidoxime.

(1) Nuclear magnetic resonance spectrum (DMSO-d$_6$, TMS) δ (ppm):
1.21 (3H, t), 1.31 (3H, t), 2.82 (4H, q), 9.88 (1H, s), 12.89 (1H, brs)

(2) Mass spectrometric data (FAB): 193 (MH⁺)

Reference Example 39 (Starting compound for use in Example 80)

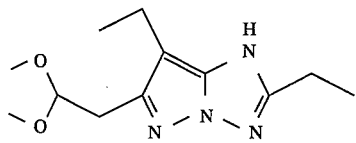

(A) In the same manner as described in the step (A) of Reference Example 28, 3.9 g of 3-amino-4-ethyl-5-(2,2-dimethoxyethyl)-1H-pyrazole was obtained from 23.4 g of n-butyronitrile and 25 g of methyl 3,3-dimethoxy propionate.

(1) Nuclear magnetic resonance spectrum (CDCl$_3$, TMS) δ (ppm):
1.09 (3H, t), 2.32 (2H, q), 2.82 (2H, d), 3.38 (6H, s), 4.50 (1H, t)

(2) Mass spectrometric data (EI): 199 (M⁺)

(B) In the same manner as described in the step (B) of Reference Example 28, 1.4 g of N-(4-ethyl-5-(2,2-dimethoxyethyl)-1H-pyrazol-3-yl)propionamidoxime was obtained from 3.8 g of 3-amino-4-ethyl-5-(2,2-dimethoxyethyl)-1H-pyrazole.

(1) Nuclear magnetic resonance spectrum (DMSO-d$_6$, TMS) δ (ppm):
0.87 (3H, t), 1.01 (3H, t), 2.21–2.23 (2H, br), 2.31 (2H, q), 2.77 (2H, d), 3.24 (6H, s), 4.51 (1H, t), 7.05 (1H, s), 9.39 (1H, s), 11.89 (1H, s)

(2) Mass spectrometric data (FAB): 271 (MH⁺)

(C) In the same manner as the procedure of the step (C) of Reference Example 25, 500 mg of 2,7-diethyl-6-(2,2-dimethoxyethyl)-1H-pyrazolo[1,5-b][1,2,4]triazole was obtained from 1.4 g of N-(4-ethyl-5-(2,2-dimethoxyethyl-1H-pyrazol-3-yl]propionamidoxime.

(1) Nuclear magnetic resonance spectrum (DMSO-d$_6$, TMS) δ (ppm):
1.16 (3H, t), 1.27 (3H, t), 2.45 (2H, q), 2.72 (2H, q), 2.78 (2H, d), 3.22 (6H, s), 4.58 (1H, t), 12.19 (1H, s)

(2) Mass spectrometric data (FAB): 253 (MH⁺)

Example 66

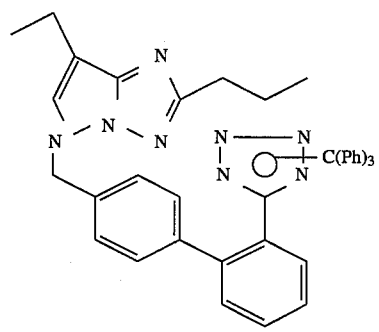

A 0.60 g portion of 7-ethyl-2-propyl-1H-pyrazolo[1,5-b][1,2,4]triazole was dissolved in 25 ml of N,N-dimethylformamide, and the resulting solution was mixed with 0.40 g of potassium t-butoxide and stirred for 15 minutes at room temperature. With cooling on an ice bath, to the reaction mixture was added 2.07 g of N-triphenylmethyl-5-[2-(4'-bromomethyl-biphenylyl)]tetrazole, followed by 1 hour of stirring at the same temperature and subsequent overnight stirring at room temperature.

After removing the solvent by distillation under a reduced pressure, the thus obtained residue was mixed with ethyl acetate and washed with water. The resulting ethyl acetate layer was dried over anhydrous magnesium sulfate and concentrated under a reduced pressure, and the thus obtained residue was subjected to silica gel column chromatography. Elution with ethyl acetate-n-hexane (9:11, v/v) gave 1.41 g of 7-ethyl-2-propyl-5-[[2'-(N-triphenylmethyl-tetrazol-5-yl)biphenyl-4-yl]methyl]-5H-pyrazolo[1,5-b][1,2,4]triazole.

(1) Nuclear magnetic resonance spectrum (CDCl$_3$, TMS) δ (ppm):
1.02 (3H, t), 1.21 (3H, t), 1.86 (2H, m), 2.55 (2H, q), 2.81 (2H, t), 5.11 (2H, s)

(2) Mass spectrometric data (FAB): 655 (MH⁺)

Example 67

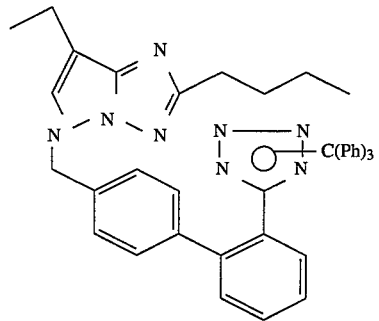

In the same manner as described in Example 66, 0.96 g of 2-butyl-7-ethyl-5-[[2'-(N-triphenylmethyl-tetrazol-5-yl)biphenyl-4-yl]methyl]-5H-pyrazolo[1,5-b][1,2,4]triazole was obtained from 0.61 g of 2-butyl-7-ethyl-1H-pyrazolo[1,5-b][1,2,4]triazole.

(1) Nuclear magnetic resonance spectrum (CDCl$_3$, TMS) δ (ppm):
0.96 (3H, t), 1.21 (3H, t), 1.45 (2H, m), 1.82 (2H, m), 2.56 (2H, q), 2.84 (2H, t), 5.11 (2H, s)

(2) Mass spectrometric data (FAB): 699 (MH⁺)

2.86 (2H, q), 5.24 (2H, s)

(2) Mass spectrometric data (FAB): 655 (MH⁺)

Example 68

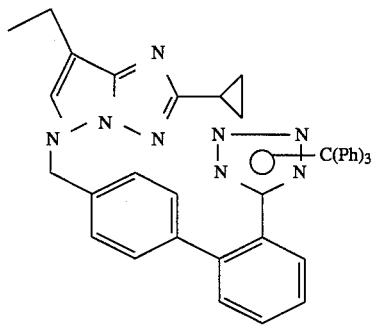

Example 70

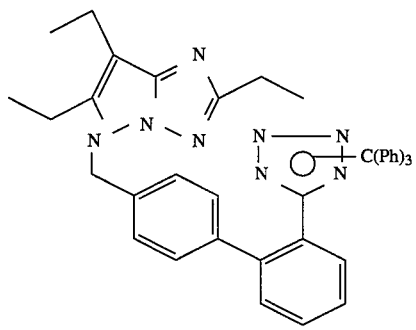

In the same manner as described in Example 66, 1.70 g of 2-cyclopropyl-7-ethyl-5-[[2'-(N-triphenylmethyl-tetrazol-5-yl)biphenyl-4-yl]methyl]-5 H-pyrazolo[1,5-b][1,2,4]triazole was obtained from 1.04 g of 2-cyclopropyl-7-ethyl-1H-pyrazolo[1,5-b][1,2,4]triazole.

(1) Nuclear magnetic resonance spectrum (CDCl₃, TMS) δ (ppm):
0.96–1.10 (4H, m), 1.19 (3H, t), 2.13 (1H, m), 2.53 (2H, q), 5.07 (2H, s)

(2) Mass spectrometric data (FAB): 653 (MH⁺)

In the same manner as described in Example 66, 2.50 g of 2,6,7-triethyl-5-[[2'-(N-triphenylmethyl-tetrazol-5-yl)biphenyl-4-yl]methyl]-5H-pyrazolo[1,5-b][1,2,4]triazole was obtained from 1.25 g of 2,6,7-triethyl-1H-pyrazolo[1,5-b][1,2,4]triazole.

(1) Nuclear magnetic resonance spectrum (CDCl₃, TMS) δ (ppm):
1.10 (3H, t), 1.29 (3H, t), 1.37 (3H, t), 2.50 (2H, q), 2.58 (2H, q), 2.84 (2H, q), 5.24 (2H, s)

(2) Mass spectrometric data (FAB): 669 (MH⁺)

Example 69

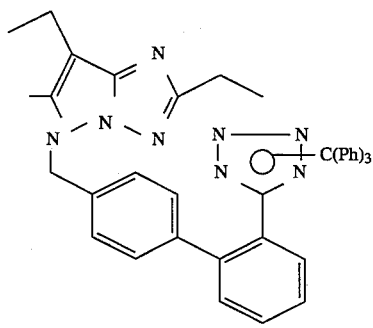

Example 71

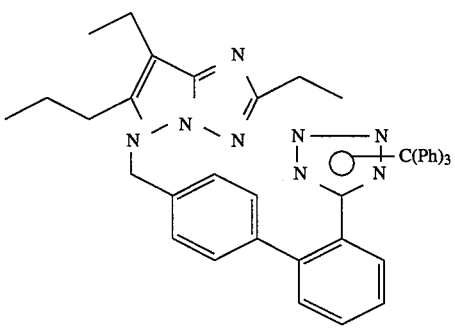

In the same manner as described in Example 66, 1.76 g of 2,7-diethyl-6-methyl-5-[[2'-(N-triphenylmethyl-tetrazol-5-yl)biphenyl-4-yl]methyl]-5H-pyrazolo[1,5-b][1,2,4]triazole was obtained from 0.70 g of 2,7-diethyl-6-methyl-1H-pyrazolo[1,5-b][1,2,4]triazole.

(1) Nuclear magnetic resonance spectrum (CDCl₃, TMS) δ (ppm):
1.27 (3H, t), 1.38 (3H, t), 2.12 (3H, s), 2.57 (2H, q), In the same manner as described in Example 66, 1.08 g of 2,7-diethyl-6-propyl-5-[[2'-(N-triphenylmethyl-tetrazol-5-yl)biphenyl-4-yl]methyl]-5 H-pyrazolo[1,5-b][1,2,4]triazole was obtained from 0.66 g of 2,7-diethyl-6-propyl-1H-pyrazolo[1,5-b][1,2,4]triazole.

(1) Nuclear magnetic resonance spectrum (CDCl₃, TMS) δ (ppm):
0.91 (3H, t), 1.31 (3H, t), 1.37 (3H, t), 1.51 (2H, m), 2.49 (2H, t), 2.58 (2H, q), 2.85 (2H, q), 5.24 (2H, s)

(2) Mass spectrometric data (FAB): 683 (MH⁺)

Example 72

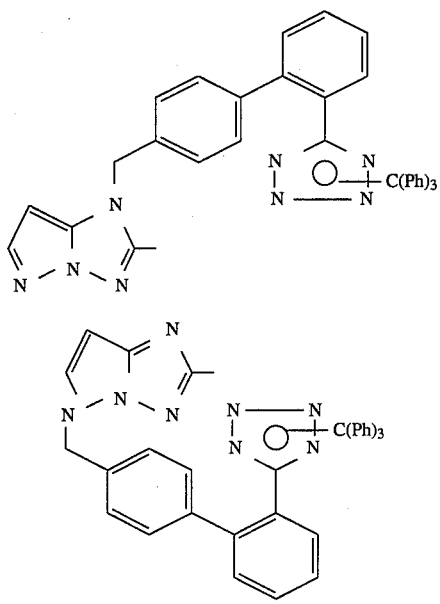

In the same manner as described in Example 66, 2.61 g of 2-methyl-1-[[2'-(N-triphenylmethyl-tetrazol-5-yl)biphenyl-4-yl]methyl]-1H-pyrazolo[1,5-b][1,2,4]triazole (compound 72a) and 1.15 g of 2-methyl-5-[[2'-(N-triphenylmethyl-tetrazol-5-yl)biphenyl-4-yl]methyl]-5H-pyrazolo[1,5-b][1,2,4]triazole (compound 72b) were obtained from 1.11 g of 2-methyl-1H-pyrazolo[1,5-b][1,2,4]triazole.

Compound 72a:

(1) Nuclear magnetic resonance spectrum (CDCl₃, TMS) δ (ppm):

2.37 (3H, s), 4.97 (2H, s), 5.43 (1H, d)

(2) Mass spectrometric data (FAB): 599 (MH⁺)

Compound 72b (1) Nuclear magnetic resonance spectrum (CDCl₃, TMS) δ (ppm):

2.51 (3H, s), 5.20 (2H, s), 6.01 (1H, d)

(2) Mass spectrometric data (FAB): 599 (MH⁺)

Example 73

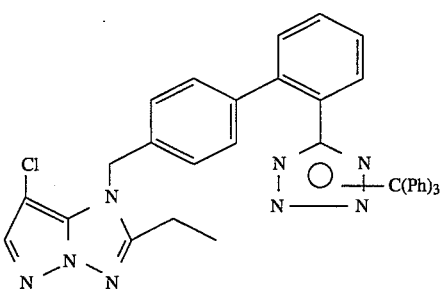

-continued

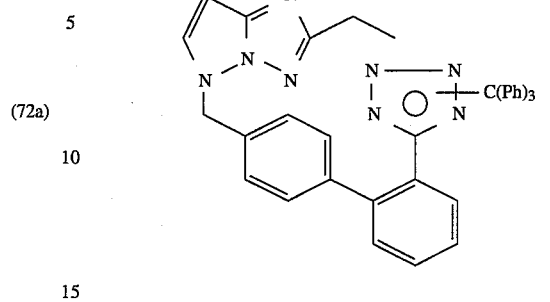

In the same manner as described in Example 66, 1.60 g of 7-chloro-2-ethyl-1-[[2'-(N-triphenylmethyl-tetrazol-5-yl)biphenyl-4-yl]methyl]-1H-pyrazolo[1,5-b][1,2,4]triazole (compound 73a) and 1.18 g of 7-chloro-2-ethyl-5-[[2'-(N-triphenylmethyl-tetrazol-5-yl)biphenyl-4-yl]methyl]-5H-pyrazolo[1,5-b][1,2,4]triazole (compound 73b) were obtained from 1.10 g of 7-chloro-2-ethyl-1H-pyrazolo[1,5-b][1,2,4]triazole.

Compound 73a:

(1) Nuclear magnetic resonance spectrum (CDCl₃, TMS) δ (ppm):

1.26 (3H, t), 2.58 (2H, q), 5.10 (2H, s)

(2) Mass spectrometric data (FAB): 647 (MH⁺)

Compound 73b (1) Nuclear magnetic resonance spectrum (CDCl₃, TMS) δ (ppm):

1.39 (3H, t), 2.86 (2H, q), 5.14 (2H, s)

(2) Mass spectrometric data (FAB): 647 (MH⁺)

Example 74

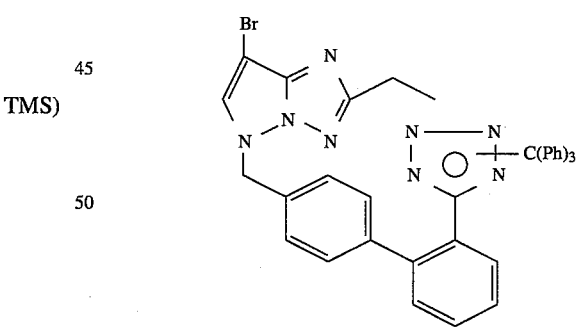

In the same manner as described in Example 66, 0.91 g of 7-bromo-2-ethyl-5-[[2'-(N-triphenylmethyl-tetrazol-5-yl)biphenyl-4-yl]methyl]-5H-pyrazolo[1,5-b][1,2,4]triazole was obtained from 1.00 g of 7-bromo-2-ethyl-1H-pyrazolo[1,5-b][1,2,4]triazole.

(1) Nuclear magnetic resonance spectrum (CDCl₃, TMS) δ (ppm):

1.40 (3H, t), 2.88 (2H, q), 5.17 (2H, s)

(2) Mass spectrometric data (FAB): 691 (MH⁺)

Example 75

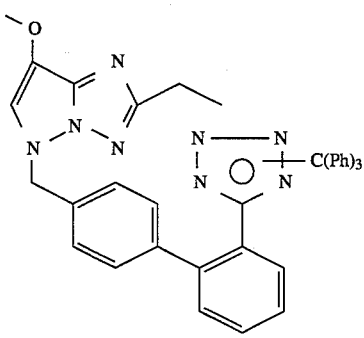

In the same manner as described in Example 66, 2.32 g of 2-ethyl-7-methoxy-5-[[2'-(N-triphenylmethyl-tetrazol- 5-yl-)biphenyl-4-yl]methyl]-5H-pyrazolo[ 1,5-b][1,2,4]triazole was obtained from 0.77 g of 2-ethyl-7-methoxy-1H-pyrazolo[1,5-b][1,2,4]triazole.

(1) Nuclear magnetic resonance spectrum (CDCl$_3$, TMS) δ (ppm):
1.39 (3H, t), 2.86 (2H, q), 3.78 (3H, s), 4.94 (2H, s), 6.49 (1H, s)

(2) Mass spectrometric data (FAB): 643 (MH$^+$)

Example 76

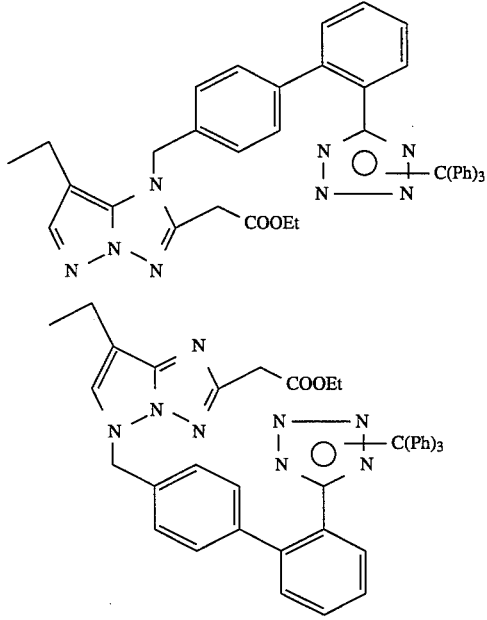

(76a)

(76b)

In the same manner as described in Example 66, 0.12 g of ethyl [7-ethyl-1-[[2'-(N-triphenylmethyl-tetrazol- 5-yl)biphenyl-4-yl]methyl]-1H-pyrazolo[1,5-b][1,2,4]triazol- 2-yl]acetate (compound 76a) and 1.11 g of ethyl [7-ethyl-5-[[ 2'-(N-triphenylmethyl-tetrazol-5-yl)biphenyl-4-yl]methyl]-5H-pyrazolo[1,5-b][1,2,4]triazol-2-yl]acetate (compound 76b) were obtained from 0.53 g of ethyl [7-ethyl-1H-pyrazolo[ 1,5-b][1,2,4]triazol-2-yl]acetate.

Compound 76a:

(1) Nuclear magnetic resonance spectrum (CDCl$_3$, TMS) δ (ppm):
1.04 (3H, t), 1.24 (3H, t), 2.29 ( 2H, q), 3.66 (2H, s), 4.15 (2H, q), 5.15 (2H, s)

(2) Mass spectrometric data (FAB): 699 (MH$^+$)

Compound 76b (1) Nuclear magnetic resonance spectrum (CDCl$_3$, TMS) δ (ppm):
1.20 (3H, t), 1.27 (3H, t), 2.54 (2H, q), 3.88 (2H, s), 4.21 (3H, q), 5.10 (2H, s)

(2) Mass spectrometric data (FAB): 699 (MH$^+$)

Example 77

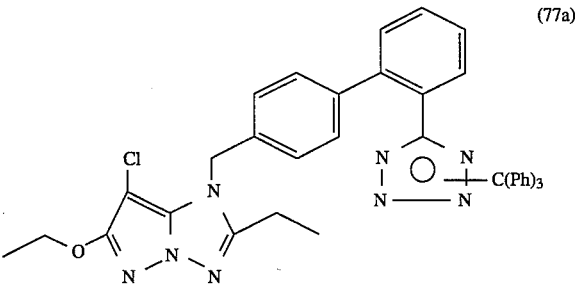

(77a)

(77b)

In the same manner as described in Example 66, 1.02 g of 6-ethoxy-2-ethyl-1-[[2'-(N-triphenylmethyl-tetrazol- 5-yl-)biphenyl-4-yl]methyl]-1H-pyrazolo[ 1,5-b][1,2,4]triazole (compound 77a) and 1.22 g of 6-ethoxy-2-ethyl-5-[[2'-(N-triphenylmethyl-tetrazol-5 -yl)biphenyl-4-yl]methyl]-5H-pyrazolo[1,5-b][1,2,4]triazole (compound 77b) were obtained from 1.80 g of 6-ethoxy-2-ethyl- 1H-pyrazolo[1, 5-b][1,2,4]triazole.

Compound 77a:

(1) Nuclear magnetic resonance spectrum (CDCl$_3$, TMS) δ (ppm):
1.29 (3H, t), 1.37 (3H, t), 2.62 (2H, q), 4.24 (2H, q), 4.89 (2H, s)

(2) Mass spectrometric data (FAB): 657 (MH$^+$)

Compound 77 b (1) Nuclear magnetic resonance spectrum (CDCl$_3$, TMS) δ (ppm):
1.36 (3H, t), 1.44 (3H, t), 2.82 (2H, q), 4.17 (2H, q), 5.12 (2H, s), 5.39 (1H, s)

(2) Mass spectrometric data (FAB): 657 (MH$^+$)

Example 78

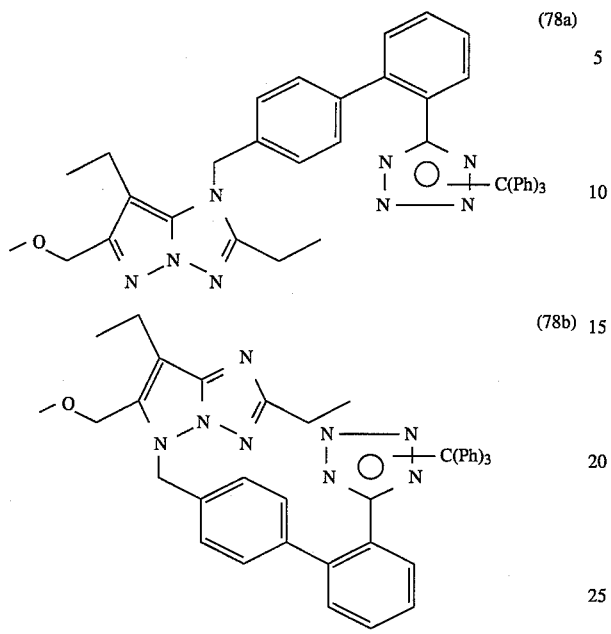

In the same manner as described in Example 66, 170 mg of 2,7-diethyl-6-methoxymethyl-1-[[2'-(N-triphenylmethyl tetrazol-5-yl)biphenyl-4-yl]methyl]-1H-pyrazolo[ 1,5-b][1, 2,4]triazole (compound 78a) and 2.5 g of 2,7-diethyl-6-methoxymethyl-5-[[2'-(N-triphenylmethyl-tetrazol- 5-yl)biphenyl-4-yl]methyl]-5H-pyrazolo[ 1,5-b][1,2,4]triazole (compound 78b) were obtained from 1.0 g of 2,7-diethyl-6-methoxymethyl-1H-pyrazolo[ 1,5-b][1,2,4]triazole.

Compound 78a:
(1) Nuclear magnetic resonance spectrum (DMSO-$d_6$, TMS) δ (ppm):
1.17 (3H, t), 1.21 (3H, t), 2.57 (2H, q), 2.71 (2H, q), 3.21 (3H, s), 4.37 (2H, s), 5.49 (2H, s)
(2) Mass spectrometric data (FAB): 685 (MH$^+$)

Compound 78b
(1) Nuclear magnetic resonance spectrum (DMSO-$d_6$, TMS) δ (ppm):
1.19–1.24 (6H, m), 2.56–2.67 (4H, m), 3.21 (3H, s), 4.45 (2H, s), 5.39 (2H, s)
(2) Mass spectrometric data (FAB): 685 (MH$^+$)

Example 79

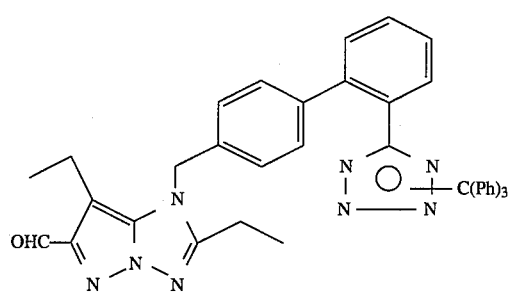

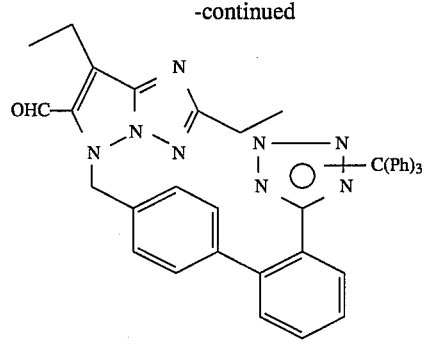

In the same manner as described in Example 66, 1.8 g of 2,7-diethyl-1-[[2'-(N-triphenylmethyl-tetrazol-5 -yl)biphenyl-4-yl]methyl]-1H-pyrazolo[1,5-b][1,2,4]triazole-6-carboxyaldehyde (compound 79a) and 2.8 g of 2,7-diethyl-5 -[[2'-(N-triphenylmethyl-tetrazol-5-yl)biphenyl-4-yl]methyl]-5H-pyrazolo[1,5-b][1,2,4]triazole-6-carboxyaldehyde (compound 79b) were obtained from 1.7 g of 2,7-diethyl-1H-pyrazolo[ 1,5-b][1,2,4]triazole-6-carboxyaldehyde.

Compound 79a:
(1) Nuclear magnetic resonance spectrum (CDCl$_3$, TMS) δ (ppm):
0.96 (3H, t), 1.32 (3H, t), 2.62–2.67 (4H, m), 5.09 (2H, s), 10.03 (1H, s)
(2) Mass spectrometric data (FAB): 669 (MH$^+$)

Compound 79b
(1) Nuclear magnetic resonance spectrum (CDCl$_3$, TMS) δ (ppm):
1.40–1.44 (6H, m), 2.93–3.00 (4H, m), 5.70 (2H, s), 9.97 (1H, s)
(2) Mass spectrometric data (FAB): 669 (MH$^+$)

Example 80

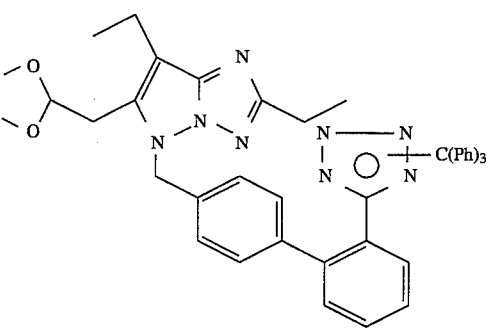

In the same manner as described in Example 66, 1.1 g of 2,7-diethyl-6-(2,2-dimethoxyethyl)-5-[[2'-(N-triphenylmethyl-tetrazol- 5-yl)biphenyl-4-yl]methyl]-5H-pyrazolo[ 1,5-b][1,2,4]triazole was obtained from 650 mg of 2,7-diethyl-6-(2,2-dimethoxyethyl)-1H-pyrazolo[ 1,5-b][1,2,4]triazole.

(1) Nuclear magnetic resonance spectrum (CDCl$_3$, TMS) δ (ppm):
1.34 (3H, t), 1.39 (3H, t), 2.62 (2H, q), 2.84 (2H, d), 2.89 (2H, q), 3.32 (6H, s), 4.35 (1H, t), 5.41 (2H, s)
(2) Mass spectrometric data (FAB): 729 (MH$^+$)

Example 81

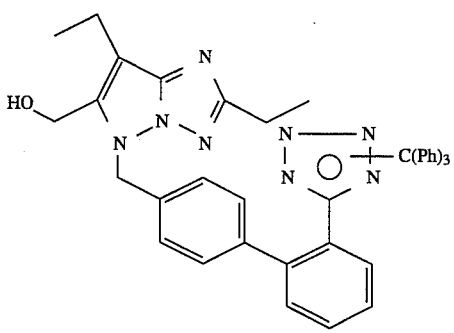

A 240 mg portion of 2,7-diethyl-5-[[2'-(N-triphenylmethyl-tetrazol- 5-yl)biphenyl-4-yl]methyl]-5H-pyrazolo[1,5-b][1,2,4]triazole-6-carboxyaldehyde was dissolved in 7 ml of an ethanol-tetrahydrofuran (1:6) mixed solvent to which, with cooling on an ice bath, was subsequently added 15 mg of sodium borohydride. With cooling on an ice bath, the mixture was stirred for 30 minutes, mixed with 5 ml of water and then adjusted to an acidic range with 1N of hydrochloric acid. After removing the solvent by distillation under a reduced pressure, the resulting residue was dissolved in ethyl acetate and washed with water and saturated sodium chloride aqueous solution in that order, and the resulting organic layer was dried over anhydrous magnesium sulfate.

Thereafter, the solvent was removed by distillation under a reduced pressure to obtain 240 mg of 2,7-diethyl-6-hydroxymethyl- 5-[[2'-(N-triphenylmethyl-tetrazol-5-yl)biphenyl- 4-yl]methyl]-5H-pyrazolo[1,5-b][1,2,4]triazole.

(1) Nuclear magnetic resonance spectrum (CDCl$_3$, TMS) δ (ppm):
1.22 (3H, t), 1.39 (3H, t), 2.54 (2H, br), 2.90 (2H, q), 4.55 (2H, s), 5.49 (2H, s)

(2) Mass spectrometric data (FAB): 671 (MH$^+$)

Example 82

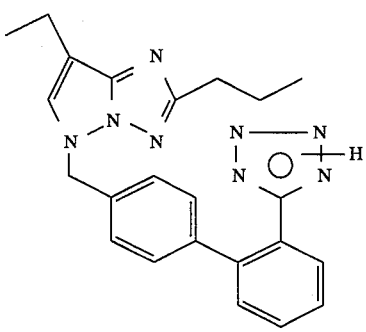

A mixture consisting of 1.11 g of 7-ethyl-2-propyl- 5-[ [2'-(N-triphenylmethyl-tetrazol-5-yl)biphenyl-4-yl] methyl] -5H-pyrazolo[1,5-b][1,2,4]triazole, 63 ml of methanol and 7 ml of acetic acid was heated for 3 hours under reflux.

After removing the solvent by distillation under a reduced pressure, the thus obtained residue was mixed with toluene and again subjected to distillation under a reduced pressure. Thereafter, the resulting residue was crystallized from ethyl acetate to give 0.64 g of 7-ethyl-2-propyl-5-[[2' -(tetrazol-5-yl)biphenyl-4-yl]methyl]-5H-pyrazolo[ 1,5-b][1,2,4]triazole in the form of colorless crystals.

(1) Melting point: 169°–170.5° C.

(2) Elemental analysis data (for C$_{23}$H$_{24}$N$_8$·0.1CH$_3$COOCH$_2$CH$_3$)

|  | C (%) | H (%) | N (%) |
|---|---|---|---|
| calculated: | 66.71 | 5.93 | 26.60 |
| found: | 66.74 | 5.98 | 26.56 |

(3) Nuclear magnetic resonance spectrum (DMSO-d$_6$, TMS) δ (ppm):
0.90 (3H, t), 1.21 (3H, t), 1.67 (2H, m), 2.58 (2H, t), 5.35 (2H, s), 7.05 (2H, d), 7.19 (2H, d)

(4) Mass spectrometric data (FAB): 413 (MH$^+$)

Example 83

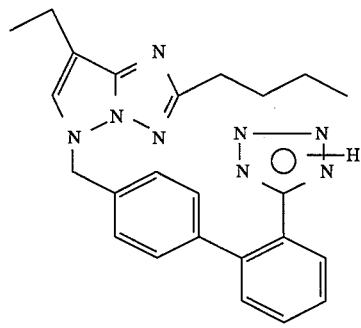

In the same manner as the procedure of Example 82, 0.49 g of 2-butyl-7-ethyl-5-[[2'-(tetrazol-5-yl)biphenyl-4-yl] methyl]-5H-pyrazolo[1,5-b][1,2,4]triazole was obtained in the form of colorless crystals from 0.80 g of 2-butyl-7 -ethyl-5-[[2'-(N-triphenylmethyl-tetrazol-5-yl)biphenyl-4-yl] methyl]-5H-pyrazolo[1,5-b][1,2,4]triazole.

(1) Melting point: 167°–169° C.

(2) Elemental analysis data (for C$_{24}$H$_{26}$N$_8$)

|  | C (%) | H (%) | N (%) |
|---|---|---|---|
| calculated: | 67.58 | 6.14 | 26.27 |
| found: | 67.33 | 6.14 | 25.98 |

(3) Nuclear magnetic resonance spectrum (DMSO-d$_6$, TMS) δ (ppm):
0.88 (3H, t), 1.21 (3H, t), 1.32 (2H, m), 1.64 (2H, m), 2.61 (2H, t), 5.35 (2H, s), 7.06 (2H, d), 7.19 (2H, d)

(4) Mass spectrometric data (FAB): 427 (MH⁺)

Example 84

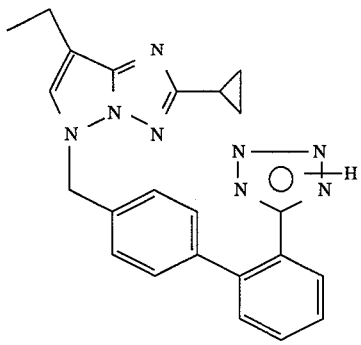

In the same manner as the procedure of Example 82, 0.64 g of 2-cyclopropyl-7-ethyl-5-[[2'-(tetrazol-5 -yl)biphenyl-4-yl]methyl]-5H-pyrazolo[1,5-b][1,2,4]triazole was obtained in the form of colorless crystals from 1.20 g of 2-cyclopropyl-7-ethyl-5-[[2'-(N-triphenylmethyl-tetrazol-5 -yl)biphenyl-4-yl]methyl]-5H-pyrazolo[1,5-b][1,2,4]triazole.

(1) Melting point: 139.5°–141° C.

(2) Elemental analysis data (for $C_{23}H_{22}N_8 \cdot 0.3H_2O$)

|  | C (%) | H (%) | N (%) |
|---|---|---|---|
| calculated: | 66.43 | 5.48 | 26.94 |
| found: | 66.59 | 5.48 | 26.70 |

(3) Nuclear magnetic resonance spectrum (DMSO-d₆, TMS) δ (ppm):
0.80–0.90 (4H, m), 1.19 (3H, t), 1.94 (1H, m), 5.34 (2H, s), 7.07 (2H, d), 7.19 (2H, d)

(4) Mass spectrometric data (FAB): 411 (MH⁺)

Example 85

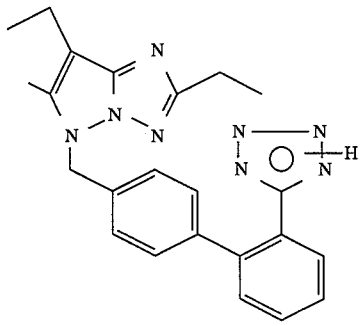

In the same manner as the procedure of Example 82, 0.77 g of 2,7-diethyl-6-methyl-5-[[2'-(tetrazol-5 -yl)biphenyl-4-yl]methyl]-5H-pyrazolo[1,5-b][1,2,4]triazole was obtained in the form of colorless crystals from 1.30 g of 2,7-diethyl-6-methyl-5-[[2'-(N-triphenylmethyl-tetrazol-5 -yl)biphenyl-4-yl]methyl]-5H-pyrazolo[1,5-b][1,2,4]triazole.

(1) Melting point: 149°–152° C.

(2) Elemental analysis data (for $C_{23}H_{24}N_8 \cdot 0.2CH_3COOCH_2CH_3$)

|  | C (%) | H (%) | N (%) |
|---|---|---|---|
| calculated: | 66.46 | 6.00 | 26.05 |
| found: | 66.53 | 5.99 | 26.06 |

(3) Nuclear magnetic resonance spectrum (DMSO-d₆, TMS) δ (ppm):
1.18 (3H, t), 1.22 (3H, t), 2.30 (3H, s), 2.49 (2H, q), 2.63 (2H, q), 5.41 (2H, s), 7.05 (2H, d), 7.08 (2H, d)

(4) Mass spectrometric data (FAB): 413 (MH⁺)

Example 86

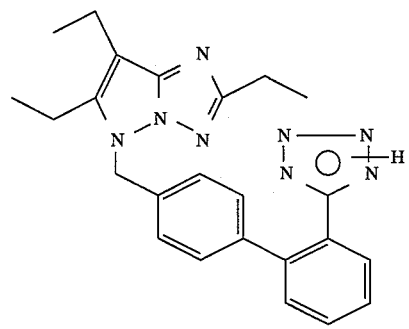

In the same manner as the procedure of Example 82, 0.71 g of 2,6,7-triethyl-5-[[2'-(tetrazol-5-yl)biphenyl-4-yl]methyl]-5H-pyrazolo[1,5-b][1,2,4]triazole was obtained in the form of colorless crystals from 1.20 g of 2,6,7-triethyl-5-[[2'-(N-triphenylmethyl-tetrazol-5-yl)biphenyl-4-yl]methyl]-5H-pyrazolo[1,5-b][1,2,4]triazole.

(1) Melting point: 207°–209° C. (decomposition)

(2) Elemental analysis data (for $C_{24}H_{26}N_8$)

|  | C (%) | H (%) | N (%) |
|---|---|---|---|
| calculated: | 67.58 | 6.14 | 26.27 |
| found: | 67.85 | 6.21 | 26.13 |

(3) Nuclear magnetic resonance spectrum (DMSO-d₆, TMS) δ (ppm):
1.06 (3H, t), 1.20 (3H, t), 1.22 (3H, t), 2.51 (2H, q), 2.63 (2H, q), 2.72 (2H, q), 5.43 (2H, s), 7.05 (4H, s)

(4) Mass spectrometric data (FAB): 427 (MH⁺)

Example 87

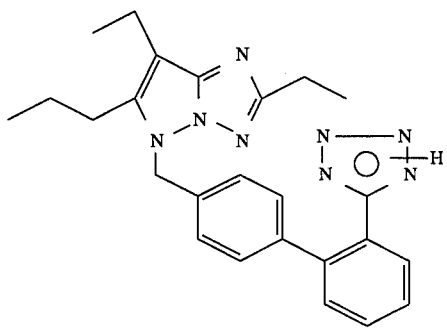

In the same manner as the procedure of Example 82, 0.50 g of 2,7-diethyl-6-propyl-5-[[2'-(tetrazol-5 -yl)biphenyl-4-yl]methyl]-5H-pyrazolo[1,5-b][1,2,4]triazole was obtained in the form of colorless crystals from 0.80 g of 2,7-diethyl-6-propyl-5-[[2'-(N-triphenylmethyl-tetrazol-5 -yl)biphenyl-4-yl]methyl]-5H-pyrazolo[1,5-b][1,2,4]triazole.

(1) Melting point: 212°–213° C. (decomposition)

(2) Elemental analysis data (for $C_{25}H_{28}N_8$)

|  | C (%) | H (%) | N (%) |
| --- | --- | --- | --- |
| calculated: | 68.16 | 6.41 | 25.43 |
| found: | 68.20 | 6.50 | 25.21 |

(3) Nuclear magnetic resonance spectrum (DMSO-$d_6$, TMS) δ (ppm):

0.89 (3H, t), 1.20 (3H, t), 1.22 (3H, t), 1.46 (2H, m), 2.60–2.70 (4H, m), 5.41 (2H, s), 7.04 (4H, t)

(4) Mass spectrometric data (FAB): 441 (MH⁺)

Example 88

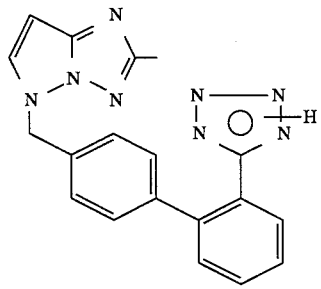

In the same manner as the procedure of Example 82, 0.41 g of 2-methyl-5-[[2'-(tetrazol-5-yl)biphenyl-4-yl] methyl]-5H-pyrazolo[1,5-b][1,2,4]triazole was obtained in the form of colorless crystals from 0.70 g of 2-methyl-5 -[[2'-(N-triphenylmethyl-tetrazol-5-yl)biphenyl-4-yl]methyl] -5H-pyrazolo[1,5-b][1,2,4]triazole.

(1) Melting point: 225°–228° C. (decomposition)

(2) Elemental analysis data (for $C_{19}H_{16}N_8 \cdot 0.2CH_3COOCH_2CH_3$)

|  | C (%) | H (%) | N (%) |
| --- | --- | --- | --- |
| calculated: | 63.59 | 4.74 | 29.96 |
| found: | 63.73 | 4.69 | 30.18 |

(3) Nuclear magnetic resonance spectrum (DMSO-$d_6$, TMS) δ (ppm):

2.29 (3H, S), 5.47 (2H, s), 6.20 (1H, d), 7.07 (2H, d), 7.19 (2H, d), 7.93 (1H, d)

(4) Mass spectrometric data (FAB): 357 (MH⁺)

Example 89

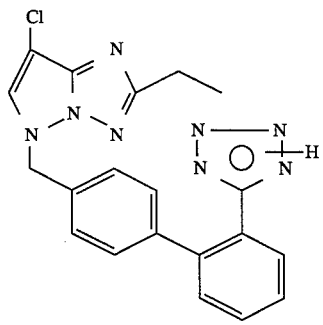

In the same manner as the procedure of Example 82, 0.61 g of 7-chloro-2-ethyl-5-[[2'-(tetrazol-5-yl)biphenyl-4-yl] methyl]-5H-pyrazolo[1,5-b][1,2,4]triazole was obtained in the form of colorless crystals from 1.05 g of 7-chloro-2 -ethyl-5-[[2'-(N-triphenylmethyl-tetrazol-5-yl)biphenyl-4-yl] methyl]-5H-pyrazolo[1,5-b][1,2,4]triazole.

(1) Melting point: 181°–182.5° C. (decomposition)

(2) Elemental analysis data (for $C_{20}H_{17}ClN_8$)

|  | C (%) | H (%) | N (%) | Cl (%) |
| --- | --- | --- | --- | --- |
| calculated: | 59.33 | 4.23 | 27.68 | 8.76 |
| found: | 59.30 | 4.20 | 27.83 | 8.99 |

(3) Nuclear magnetic resonance spectrum (DMSO-$d_6$, TMS) δ (ppm):

1.23 (3H, t), 2.67 (2H, q), 5.46 (2H, s), 7.09 (2H, d), 7.24 (2H, d), 8.22 (1H, s)

(4) Mass spectrometric data (FAB): 405 (MH⁺)

Example 90

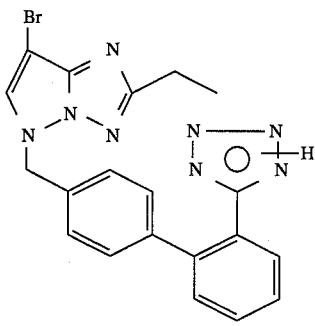

In the same manner as the procedure of Example 82, 0.40 g of 7-bromo-2-ethyl-5-[[2'-(tetrazol-5-yl)biphenyl-4-yl]methyl]-5H-pyrazolo[1,5-b][1,2,4]triazole was obtained the form of colorless crystals from 0.70 g of 7-bromo-2-ethyl-5-[[2'-(N-triphenylmethyl-tetrazol-5-yl)biphenyl-4-yl]methyl]-5H-pyrazolo[1,5-b][1,2,4]triazole.

(1) Melting point: 186°–188° C. (decomposition)

(2) Elemental analysis data (for $C_{20}H_{17}BrN_8$)

|  | C (%) | H (%) | N (%) | Br (%) |
|---|---|---|---|---|
| calculated: | 53.46 | 3.81 | 24.94 | 17.78 |
| found: | 53.19 | 3.82 | 24.82 | 17.88 |

(3) Nuclear magnetic resonance spectrum (DMSO-$d_6$, TMS) δ (ppm):
1.23 (3H, t), 2.67 (2H, q), 5.47 (2H, s), 7.10 (2H, d), 7.25 (2H, d), 8.22 (1H, s)

(4) Mass spectrometric data (FAB): 449 (MH$^+$)

Example 91

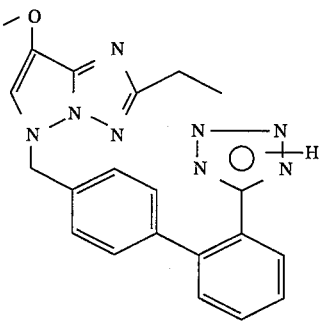

In the same manner as the procedure of Example 82, 0.47 g of 2-ethyl-7-methoxy-5-[[2'-(tetrazol-5-yl)biphenyl-4-yl]methyl]-5H-pyrazolo[1,5-b][1,2,4]triazole was obtained in the form of colorless crystals from 1.81 g of 2-ethyl-7-methoxy-5-[[2'-(N-triphenylmethyl-tetrazol-5-yl)biphenyl-4-yl]methyl]-5H-pyrazolo[1,5-b][1,2,4]triazole.

(1) Elemental analysis data (for $C_{21}H_{20}N_8O$)

|  | C (%) | H (%) | N (%) |
|---|---|---|---|
| calculated: | 62.99 | 5.03 | 27.98 |
| found: | 62.91 | 5.01 | 27.87 |

(2) Nuclear magnetic resonance spectrum (DMSO-$d_6$, TMS) δ (ppm):
1.22 (3H, t), 2.65 (2H, q), 3.81 (3H, s), 5.20 (2H, s), 7.05 (2H, d), 7.21 (2H, d)

(3) Mass spectrometric data (FAB): 401 (MH$^+$)

Example 92

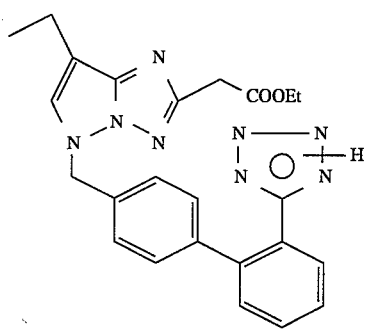

A mixture consisting of 1.02 g of ethyl [7-ethyl-5-[[2'-(N-triphenylmethyl-tetrazol-5-yl)biphenyl-4-yl]methyl]-5H-pyrazolo[1,5-b][1,2,4]triazol-2-yl]acetate, 45 ml of methanol and 5 ml of acetic acid was heated for 2 hours under reflux. The solvent was removed by distillation under a reduced pressure, the thus obtained residue was mixed with toluene, and the mixture again subjected to distillation under a reduced pressure.

Thereafter, the resulting residue was subjected to silica gel column chromatography. Elution with a gradient from chloroform only to methanol-chloroform (1:9, v/v) gave 0.62 g of ethyl [7-ethyl-5-[[2'-(tetrazol-5-yl)biphenyl-4-yl]methyl]-5H-pyrazolo[1,5-b][1,2,4]triazol-2-yl]acetate in the form of colorless amorphous foamy material.

(1) Nuclear magnetic resonance spectrum (DMSO-$d_6$, TMS) δ (ppm):
1.17 (3H, t), 1.22 (3H, t), 2.53 (2H, q), 3.72 (2H, s), 4.08 (2H, q), 5.39 (2H, s), 7.06 (2H, d), 7.20 (2H, d), 7.73 (1H, s)

(2) Mass spectrometric data (FAB): 457 (MH⁺)

Example 93

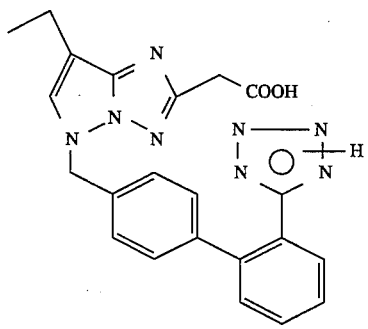

A mixture consisting of 0.44 g of ethyl [7-ethyl-5-[[2'-(tetrazol-5-yl)biphenyl-4-yl]methyl]-5H-pyrazolo[1,5-b][1,2,4]triazol-2-yl]acetate, 27 ml of ethanol and 3 ml of 1N sodium hydroxide aqueous solution was heated for 2 hours under reflux. The reaction mixture was concentrated under a reduced pressure and the resulting residue was dissolved in 10 ml of water.

With cooling on an ice bath, the thus prepared solution was adjusted to pH 2 with 0.5N hydrochloric acid aqueous solution, and the thus precipitated solid material was collected by filtration to give 0.37 g of [7-ethyl-5-[[2'-(tetrazol-5-yl)biphenyl-4-yl]methyl]-5H-pyrazolo[1,5-b][1,2,4]triazol-2-yl]acetic acid in the form of colorless amorphous solid.

(1) Elemental analysis data (for $C_{22}H_{20}N_8O_2 \cdot 0.7H_2O$)

|  | C (%) | H (%) | N (%) |
|---|---|---|---|
| calculated: | 59.91 | 4.89 | 25.41 |
| found: | 59.84 | 4.56 | 25.48 |

(2) Nuclear magnetic resonance spectrum (DMSO-$d_6$, TMS) δ (ppm):
1.22 (3H, t), 2.54 (2H, q), 3.65 (2H, s), 5.40 (2H, s), 7.07 (2H, d), 7.21 (2H, d), 7.75 1H, s)

(3) Mass spectrometric data (FAB): 429 (MH⁺)

Example 94

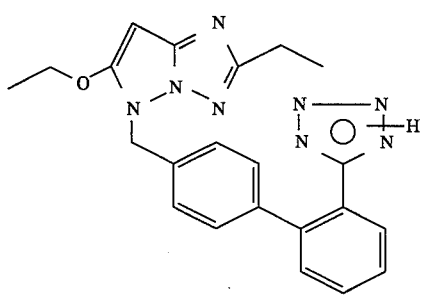

In the same manner as the procedure of Example 92, 0.59 g of 6-ethoxy-2-ethyl-5-[[2'-(tetrazol-5-yl)biphenyl-4-yl]methyl]-5H-pyrazolo[1,5-b][1,2,4]triazole was obtained in the form of colorless amorphous foamy material from 1.08 g of 6-ethoxy-2-ethyl-5-[[2'-(N-triphenylmethyl-tetrazol-5-yl)biphenyl-4-yl]methyl]-5H-pyrazolo[1,5-b][1,2,4]triazole.

(1) Nuclear magnetic resonance spectrum (DMSO-$d_6$, TMS) δ (ppm):
1.20 (3H, t), 1.36 (3H, t), 2.60 (2H, q), 4.23 (2H, q) 5.17 (2H, s) 5.68 (1H, s) 7.05 (2H, d), 7.13 (2H, d)

(2) Mass spectrometric data (EI): 414 (M⁺)

Example 95

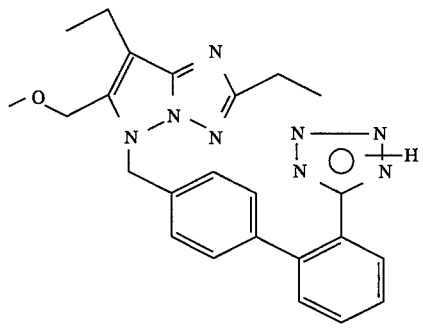

In the same manner as the procedure of Example 82, 480 mg of 2,7-diethyl-6-methoxymethyl-5-[[2'-(tetrazol-5-yl)biphenyl-4-yl]methyl]-5H-pyrazolo[1,5-b][1,2,4]triazole was obtained from 1.0 g of 2,7-diethyl-6-methoxymethyl-5-[[2'-(N-triphenylmethyl-tetrazol-5-yl)biphenyl-4-yl]methyl]-5H-pyrazolo[1,5-b][1,2,4]triazole.

(1) Melting point: 192°–194° C.

(2) Elemental analysis data (for $C_{24}H_{26}N_8O$)

|  | C (%) | H (%) | N (%) |
|---|---|---|---|
| calculated: | 65.14 | 5.92 | 25.32 |
| found: | 65.16 | 5.97 | 25.33 |

(3) Nuclear magnetic resonance spectrum (DMSO-$d_6$, TMS) δ (ppm):
1.22 (6H, t), 2.60 (2H, q), 2.65 (2H, q), 3.24 (3H, s), 4.56 (2H, s), 5.44 (2H, s), 7.05 (2H, d), 7.14 (2H, d)

(4) Mass spectrometric data (FAB): 443 (MH⁺)

Example 96

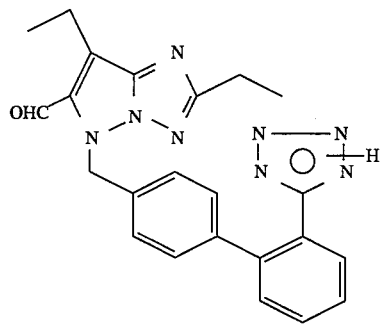

In the same manner as the procedure of Example 82, 300 mg of 2,7-diethyl-5-[[2'-(tetrazol-5-yl)biphenyl-4-yl]methyl]-5H-pyrazolo[1,5-b][1,2,4]triazole-6 -carboxyaldehyde was obtained from 800 mg of 2,7-diethyl-5 -[[2'-(N-triphenylmethyl-tetrazol-5-yl)biphenyl-4-yl]methyl] -5H-pyrazolo[1,5-b][1,2,4]triazole-6-carboxyaldehyde.

(1) Melting point: 193°–195° C.

(2) Elemental analysis data (for $C_{23}H_{22}N_8O \cdot 0.2AcOEt$)

|  | C (%) | H (%) | N (%) |
|---|---|---|---|
| calculated: | 64.37 | 5.36 | 25.23 |
| found: | 64.54 | 5.40 | 25.42 |

(3) Nuclear magnetic resonance spectrum (DMSO-$d_6$, TMS) δ (ppm):
1.26 (3H, t), 1.33 (3H, t), 2.74 (2H, q), 2.98 (2H, q), 5.72 (2H, s), 7.04 (2H, d), 7.13 (2H, d), 10.09 (1H, s)

(4) Mass spectrometric data (FAB): 427 (MH$^+$)

Example 97

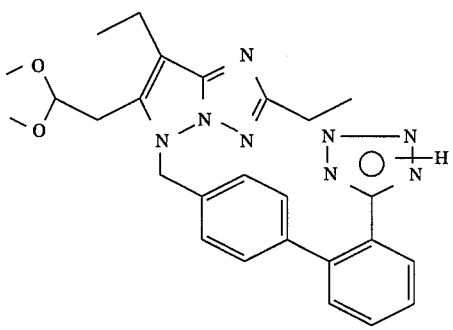

In the same manner as the procedure of Example 82, 420 mg of 2,7-diethyl-6-(2,2-dimethoxyethyl)-5-[[2' -(tetrazol-5-yl)biphenyl-4-yl]methyl]-5H-pyrazolo[ 1,5-b][1,2,4]triazole was obtained from 1.1 g of 2,7-diethyl-6-(2,2-dimethoxyethyl)-5-[[2'-(N-triphenylmethyl-tetrazol-5-yl)biphenyl-4-yl]methyl]-5H-pyrazolo[ 1,5-b][1,2,4]triazole.

(1) Melting point: 185°–187° C.

(2) Elemental analysis data (for $C_{26}H_{30}N_8O_2 \cdot 0.1H_2O$)

|  | C (%) | H (%) | N (%) |
|---|---|---|---|
| calculated: | 63.94 | 6.23 | 22.94 |
| found: | 63.95 | 6.22 | 22.93 |

(3) Nuclear magnetic resonance spectrum (DMSO-$d_6$, TMS) δ (ppm):
1.22 (6H, t), 2.53 (2H, q), 2.64 (2H, q), 3.00 (2H, d), 3.21 (6H, s), 4.36 (1H, t), 5.45 (2H, s), 7.02 (2H, d), 7.06 (2H, d)

(4) Mass spectrometric data (FAB): 486 (MH$^+$)

Example 98

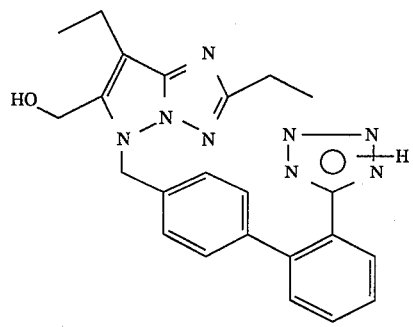

In the same manner as the procedure of Example 82, 100 mg of 2,7-diethyl-6-hydroxyethyl-5-[[2'-(tetrazol-5 -yl)biphenyl-4-yl]methyl]-5H-pyrazolo[1,5-b][1,2,4]triazole was obtained from 800 mg of 2,7-diethyl-6-hydroxymethyl-5 -[[2'-(N-triphenylmethyl-5-yl)biphenyl-4-yl]methyl]-5H-pyrazolo[ 1,5-b][1,2,4]triazole.

(1) Melting point: 182°–184° C.

(2) Elemental analysis data (for $C_{23}H_{24}N_8O \cdot 0.1H_2O$)

|  | C (%) | H (%) | N (%) |
|---|---|---|---|
| calculated: | 64.20 | 5.67 | 26.04 |
| found: | 64.23 | 5.65 | 26.02 |

(3) Nuclear magnetic resonance spectrum (DMSO-$d_6$, TMS) δ (ppm):
1.21 (3H, t), 1.22 (3H, t), 2.58 (2H, q), 2.63 (2H, q), 4.57 (2H, s), 5.46 (2H, s), 7.04 (2H, d), 7.16 (2H, d)

(4) Mass spectrometric data (FAB): 429 (MH$^+$)

Example 99

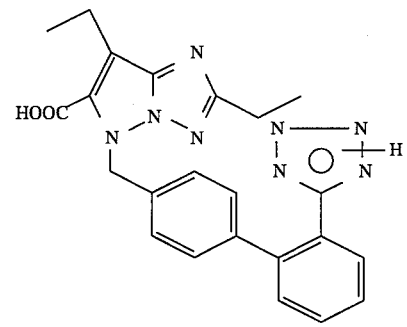

A 630 mg portion of 2,7-diethyl-5-[[2'-(tetrazol-5 -yl)biphenyl-4-yl]methyl]-5H-pyrazolo[1,5-b][1,2,4]triazole-6-carboxyaldehyde was suspended in 20 ml of ethanol. Next, 240 mg of sodium hydroxide was allowed to react with 500 mg of silver nitrate in 2 ml of water which was cooled on an ice bath, and the thus prepared solution was added to the above reaction solution to carry out 1 hour of heating under reflux. After spontaneous cooling of the thus obtained reaction solution, insoluble materials were removed by filtration and the resulting filtrate was evaporated to dryness under a reduced pressure.

The thus obtained residue was dissolved in 2 ml of water, and the solution was adjusted to an acidic range with 1N hydrochloric acid and then subjected to extraction with ethyl acetate. The organic layer was dried over anhydrous magnesium sulfate, and the solvent was removed by distillation under a reduced pressure to give 190 mg of 2,7-diethyl-5-[[2'-(tetrazol-5-yl)biphenyl-4-yl]methyl]-5H-pyrazolo[1,5-b][1,2,4]triazole-6-carbonic acid.

(1) Melting point: 171°–174° C.
(2) Nuclear magnetic resonance spectrum (DMSO-$d_6$, TMS) δ (ppm):
1.24 (3H, t), 1.26 (3H, t), 2.71 (2H, q), 2.91 (2H, q), 5.73 (2H, s), 7.04 (2H, d), 7.09 (2H, d)
(3) Mass spectrometric data (FAB): 443 (MH$^+$)

Example 100

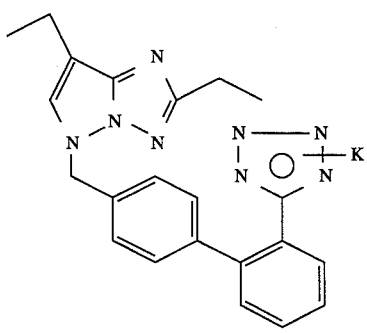

(1) A 150 ml portion of methanol was added to a mixture consisting of 8.39 g of 2,7-diethyl-5-[[2'-(tetrazol-5-yl)biphenyl-4-yl]methyl]-5H-pyrazolo[1,5-b][1,2,4]triazole and 1.46 g of potassium carbonate, and the mixture was heated until solid materials were dissolved. The solvent was removed by distillation under a reduced pressure, and the resulting residue was crystallized from ethyl acetate to give 8.96 g of crude crystals of 2,7-diethyl-5-[[2'-(tetrazol-5 -yl)biphenyl-4-yl]methyl]-5H-pyrazolo[1,5-b][1,2,4]triazole potassium salt.

(2) A 11.8 g portion of the crude crystal of 2,7 -diethyl-5-[[2'-(tetrazol-5-yl)biphenyl-4-yl]methyl]-5H-pyrazolo[1,5-b][1,2,4]triazole potassium salt was dissolved in 90 ml of ethyl acetate with heating, followed by filtration while hot. A 0.49 nil portion of water was added to the resulting filtrate which was stirred vigorously. Thereafter, the thus precipitated crystals were collected by filtration to give 11.5 g of 2,7-diethyl-5-[[2'-(tetrazol-5 -yl)biphenyl-4-yl]methyl]-5H-pyrazolo[1,5-b][1,2,4]triazole potassium salt.

(1) Elemental analysis data (for $C_{22}H_{21}N_8K \cdot H_2O$)

|  | C (%) | H (%) | N (%) |
|---|---|---|---|
| calculated: | 58.13 | 5.10 | 24.65 |
| found: | 58.29 | 5.13 | 24.81 |

(2) Nuclear magnetic resonance spectrum (DMSO-$d_6$, TMS) δ (ppm):
1.20–1.24 (6H, m), 2.52 (2H, q), 2.65 (2H, q), 5.32 (2H, s), 7.07 (2H, d), 7.10 (2H, d), 7.65 (1H, s)
(3) Mass spectrometric data (FAB): 475 (M+K)$^+$ Example 101

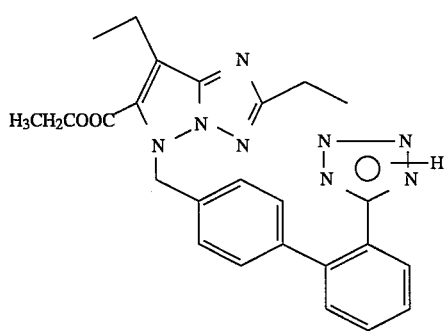

A mixture consisting of 1.13 g of 2,7-diethyl-5 -[[2'-(tetrazol-5-yl)biphenyl-4-yl]methyl]-5H-pyrazolo[1,5-b][1,2,4]triazole-6-carboxyaldehyde, 30 ml of ethanol, 0.65 g of sodium cyanide, 5.30 g of manganese dioxide and 0.23 ml of acetic acid was stirred overnight at room temperature. The reaction mixture was filtered through celite and the resulting filtrate was concentrated under a reduced pressure. The thus obtained residue was mixed with chloroform and again passed through celite. The resulting filtrate was concentrated under a reduced pressure, and subjected to silica gel column chromatography. Elution was conducted with an ethanol-chloroform (2:23, v/v) mixed solvent. Fractions containing the compound of interest were concentrated under a reduced pressure, and the thus obtained residue was dissolved in an appropriate volume of a mixed solution consisting of diluted sodium bicarbonate aqueous solution and ethanol, thereby adjusting the resulting solution to weak alkaline side. After removing the solvent by distillation under a reduced pressure, the resulting residue was dissolved in 40 ml of water, and the solution was adjusted to pH 2 with 1N hydrochloric acid. Thereafter, the solid material thus precipitated was collected by filtration to give 0.56 g of ethyl 2,7-diethyl-5-[[2'-(tetrazol-5 -yl)biphenyl-4-yl]methyl]-5H-pyrazolo[1,5-b][1,2,4]triazole-6-carboxylate in the form of amorphous solid.

(1) Elemental analysis data (for $C_{25}H_{26}N_8O_2$)

|  | C (%) | H (%) | N (%) |
|---|---|---|---|
| calculated: | 63.82 | 5.57 | 23.81 |
| found: | 63.63 | 6.64 | 23.80 |

(2) Nuclear magnetic resonance spectrum (DMSO-$d_6$, TMS) δ (ppm):
1.24–1.30 (9H, m), 2.73 (2H, q), 2.90 (2H, q), 4.36 (2H, q), 5.68 (2H, s), 7.05 (2H, d), 7.10 (1H, d)

(3) Mass spectrometric data (FAB): 471 (MH⁺)

Example 102

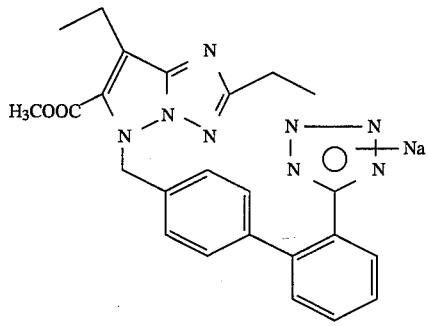

A mixture consisting of 1.13 g of 2,7-diethyl-5-[ [2'-(tetrazol-5-yl)biphenyl-4-yl]methyl]-5H-pyrazolo[ 1,5-b][1, 2,4]triazole-6-carboxyaldehyde, 20 ml of methanol, 0.65 g of sodium cyanide, 5.30 g of manganese dioxide and 0.23 ml of acetic acid was stirred for 3 days at room temperature. The reaction mixture was filtered through celite and the resulting filtrate was concentrated under a reduced pressure. The thus obtained residue was mixed with chloroform and again passed through celite. The resulting filtrate was concentrated under a reduced pressure, and subjected to silica gel column chromatography. Elution was conducted with a methanol-chloroform (3:17, v/v) mixed solvent. Fractions containing the compound of interest were concentrated under a reduced pressure, and the thus obtained residue was dissolved in 4 ml of ethyl acetate. Thereafter, the thus prepared solution was stirred overnight while cooling on an ice bath, and the solid material thus precipitated was collected by filtration to give 0.48 g of methyl 2,7-diethyl-5-[ [2'-(tetrazol-5-yl)biphenyl-4-yl] methyl]-5H-pyrazolo[1,5-b][1,2,4]triazole-6-carboxylate sodium salt in the form of amorphous solid.

(1) Elemental analysis data (for C$_{24}$H$_{23}$N$_8$O$_2$Na.0.7H$_2$O)

|  | C (%) | H (%) | N (%) |
| --- | --- | --- | --- |
| calculated: | 58.70 | 5.01 | 22.82 |
| found: | 58.83 | 5.09 | 22.79 |

(2) Nuclear magnetic resonance spectrum (DMSO-d$_6$, TMS) δ (ppm):
1.24–1.27 (6H, m), 2.74 (2H, q), 2.89 (2H, q), 3.91 (3H, s), 5.67 (2H, s), 7.04 (2H, d), 7.06 (2H, d)

(3) Mass spectrometric data (FAB): 501 (M+Na)⁺

Example 103

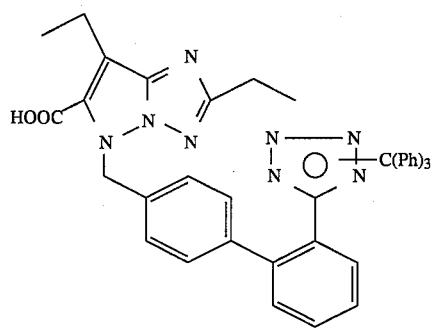

A mixture consisting of 8.83 g of 2,7-diethyl-5 -[[2'-(tetrazol-5-yl)biphenyl-4-yl]methyl]-5H-pyrazolo[ 1,5-b][1, 2,4]triazole-6-carboxylic acid, 60 ml of N,N-dimethylformamide, 2.82 ml of triethylamine and 5.66 g of triphenylmethyl chloride was stirred overnight at room temperature. After removing the solvent by distillation under a reduced pressure, the thus obtained residue was mixed with 250 ml of ethyl acetate and then washed with 150 ml of water. Thereafter, the ethyl acetate layer was stirred overnight at room temperature, and the solid material thus precipitated was collected by filtration to give 6.98 g of 2,7-diethyl-5-[[2'-(N-triphenylmethyl-tetrazol-5-yl)biphenyl- 4-yl]methyl]-5H-pyrazolo[1,5-b][1,2,4]triazole-6-carboxylic acid.

(1) Nuclear magnetic resonance spectrum DMSO-d$_6$, TMS) δ (ppm):
1.21–1.25 (6H, m), 2.70 (2H, q), 2.91 (2H, q), 5.68 (2H, s), 6.85 (6H, d), 7.01 (2H, d), 7.04 (2H, d)

(2) Mass spectrometric data (FAB): 683 (M—H)⁻

Example 104

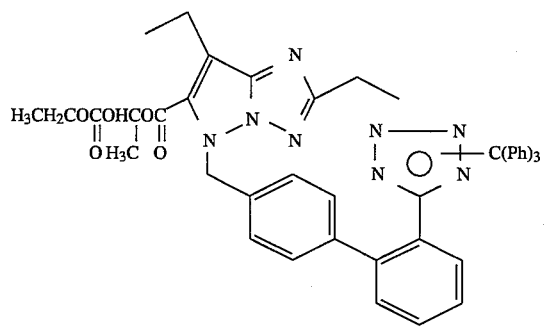

A mixture consisting of 4.50 g of ethyl 1-chloroethylcarbonate, 13.2 g of sodium iodide and 100 ml of acetonitrile was stirred for 45 minutes at an external temperature of 60° to 70° C. The solvent was removed by distillation under a reduced pressure, and the thus obtained residue was mixed with ether, followed by the removal of the formed salt by filtration. The resulting filtrate was concentrated under a reduced pressure and mixed with 40 ml of acetone to prepare an acetone solution of ethyl 1-iodoethylcarbonate.

On the other hand, 6.73 g of 2,7-diethyl-5-[[2'-(N-triphenylmethyl-tetrazol- 5-yl)biphenyl-4-yl]methyl]-5H-pyrazolo[ 1,5-b][1,2,4]triazole-6-carboxylic acid was dissolved in 0.1N ethanolic potassium hydroxide solution. The solvent was removed by distillation under a reduced pressure and the resulting residue was dissolved in 250 ml of acetone to which, with cooling on an ice bath, was subsequently added the previously prepared ethyl 1-iodoethylcarbonate in a dropwise manner spending 10 minutes. The resulting reaction mixture was stirred for 2 days at room temperature and, after removing the solvent by distillation under a reduced pressure, subjected to silica gel column chromatography. Elution was conducted with an ethyl acetate-n-hexane (3:7, v/v) mixed solvent to give 5.75 g of 1-ethoxycarbonyloxyethyl 2,7-diethyl-5-[[2'-(N-triphenylmethyl-tetrazol- 5-yl)biphenyl-4-yl]methyl]-5H-pyrazolo[ 1,5-b][1,2,4]triazole-6-carboxylate.

(1) Nuclear magnetic resonance spectrum (CDCl$_3$, TMS) δ (ppm):
1.28 (6H, t), 1.39 (3H, t), 1.63 (3H, d), 2.90 (2H, q), 2.97 (2H, q), 4.20–4.24 (2H, m), 5.64 (1H, d), 5.68 (1H, d), 6.91 (6H, d), 6.92–7.07 (5H, m)

(2) Mass spectrometric data (FAB): 801 (MH$^+$)

Example 105

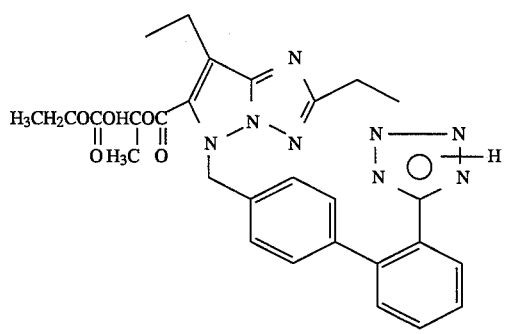

A mixture consisting of 5.64 g of 1-ethoxycarbonyloxyethyl 2,7-diethyl-5-[[2'-(N-triphenylmethyl-tetrazol- 5-yl)biphenyl-4-yl]methyl]-5H-pyrazolo[ 1,5-b][1,2,4]triazole-6-carboxylate, 230 ml of methanol and 12 ml of acetic acid was heated under reflux for 3 hours. After removing the solvent by distillation under a reduced pressure, the resulting residue was subjected to silica gel column chromatography. Elution was conducted with a methanol-chloroform (1:19, v/v) mixed solvent to give 3.76 g of 1-ethoxycarbonyloxyethyl 2,7-diethyl-5-[[2' -(tetrazol-5-yl)biphenyl-4-yl]methyl]-5H-pyrazolo[ 1,5-b][1,2,4]triazole-6-carboxylate in the form of amorphous foamy material.

(1) Elemental analysis data (for C$_{28}$H$_{30}$N$_8$O$_5$·0.3H$_2$O)

|  | C (%) | H (%) | N (%) |
|---|---|---|---|
| calculated: | 59.63 | 5.47 | 19.87 |
| found: | 59.64 | 5.43 | 19.85 |

(2) Nuclear magnetic resonance spectrum (CDCl$_3$, TMS) δ (ppm):
1.09 (3H, t), 1.24–1.28 (6H, m), 1.63 (3H, d), 2.64–2.72 (4H, m), 4.14–4.20 (2H, m), 5.72 (1H, d), 5.77 (1H, d), 6.90–7.00 (5H, m)

(3) Mass spectrometric data (FAB): 559 (MH$^+$)

Compounds shown in Table 3 can be produced in the same manner as described in Examples 104 and 105 using corresponding alkylating agents.

TABLE 3

| R$^5$ | R$^{16}$ |
|---|---|
| —COOCHOCO—cyclohexyl<br>CH$_3$ O | —C(Ph)$_3$ |
| —COOCHOCO—cyclohexyl<br>CH$_3$ O | —H |
| —COOCH$_2$OCC(CH$_3$)$_3$<br>O | —C(Ph)$_3$ |
| —COOCH$_2$OCC(CH$_3$)$_3$<br>O | —H |
| —COOCH$_2$-(dioxolone with CH$_3$) | —C(Ph)$_3$ |
| —COOCH$_2$-(dioxolone with CH$_3$) | —H |
| —COO-(phthalide) | —C(Ph)$_3$ |
| —COO-(phthalide) | —H |
| —COOCHOCCH$_3$<br>CH$_3$ O | —C(Ph)$_3$ |

TABLE 3-continued

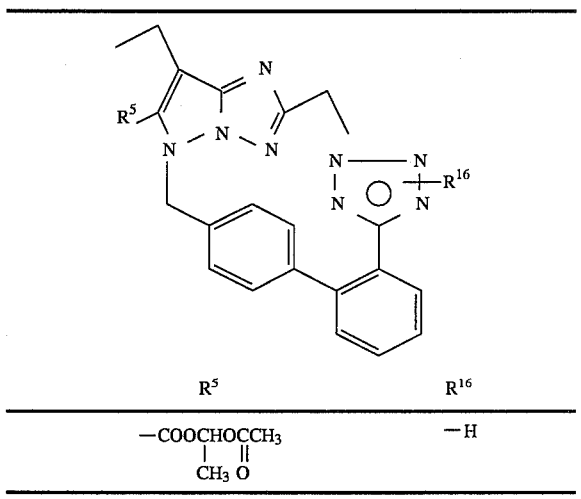

| R⁵ | R¹⁶ |
|---|---|
| —COOCHOCCH₃<br>　　　\|　\|\|<br>　CH₃ O | —H |

We claim:

1. A pyrazolotriazole derivative represented by the general formula:

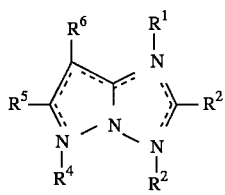

wherein each symbol means as follows;

$R^1$, $R^3$ and $R_4$: one of them represents a hydrogen atom, a biphenylmethyl group having a tetrazolyl group which may be substituted by aralkyl, or a lower alkyl group, and each of the remaining two has no substituent, $R_2$: a hydrogen atom, a biphenylmethyl group having a tetrazolyl group which may be substituted by aralkyl, a cycloalkyl group, or a lower alkyl group which may be substituted by hydroxyl, lower alkoxy, carboxyl or lower alkoxycarbonyl, and $R^5$ and $R_6$: these may be the same or different from each other, and each represents a hydrogen atom, a halogen atom, a biphenylmethyl group having a tetrazolyl group which may be substituted by aralkyl, a formyl group, a carboxyl group, an esterified carboxyl group, a cycloalkyl group, a lower alkoxy group, or a lower alkyl group which may be substituted by hydroxyl, formyl, carboxyl, lower alkoxy or lower alkoxycarbonyl, provided that at least one of $R^1$ to $R^6$ is a biphenylmethyl group having a tetrazolyl group which may be substituted by aralkyl, and the broken lines mean that the pyrazolotriazole ring forms three double bonds; or a pharmaceutically acceptable salt thereof.

2. A pyrazolotriazole derivative of claim 1 represented by the general formula:

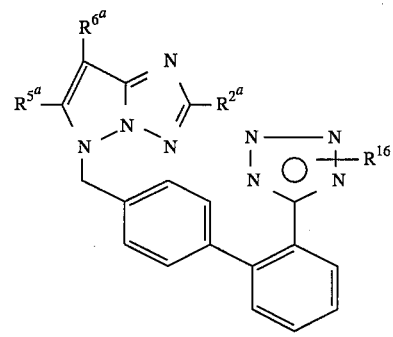

wherein each symbol means as follows;

$R^{2a}$: a lower alkyl group or a cycloalkyl group, $R^{5a}$: a hydrogen atom, a formyl group, a carboxyl group, an esterified carboxyl group or a lower alkyl group which may be substituted by hydroxyl, lower alkoxy or carboxyl, $R^{6a}$: a lower alkyl group, and $R^{16}$: a hydrogen atom or an aralkyl group; or a salt thereof.

3. A pyrazolotriazole derivative of claim 1 which is 2,7-Diethyl-5-[ [2'-(tetrazol-5-yl)biphenyl-4-yl]methyl]-5H-pyrazolo[1,5-b][1,2,4]triazole or a potassium salt thereof.

4. A pyrazolotriazole derivative of claim 1 which is 2,7-Diethyl-5-[ [2'-(tetrazol-5-yl)biphenyl-4-yl]methyl]-5H-pyrazolo[1,5-b][1,2,4]triazole-6 -carboxylic acid or an ester thereof.

5. A pyrazolotriazole derivative of claim 1 which is 2,7-Diethyl-5-[ [2'-(tetrazol-5-yl)biphenyl-4-yl]methyl]-5H-pyrazolo[1,5-b][1,2,4]triazole-6 -carboxyaldehyde.

6. A pyrazolotriazole derivative of claim 1 which is 2,7-Diethyl-6 -hydroxymethyl-5-[[2'-(tetrazol-5-yl)biphenyl-4-yl]methyl]-5H-pyrazolo[1,5-b] [1,2,4]triazole.

7. A pharmaceutical composition which comprises a pharmacologically effective amount of the pyrazolotriazole derivative or a pharmaceutically acceptable salt thereof of claim 1 and a pharmaceutically acceptable carrier.

8. A pharmaceutical composition containing as the active ingredient a pyrazoiotriazole derivative represented by the general formula:

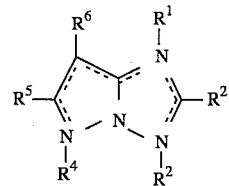

wherein each symbol means as follows;

$R^1$, $R^3$ and $R^4$: one of them represents a hydrogen atom, a biphenylmethyl group having a tetrazolyl group which may be substituted by aralkyl, or a lower alkyl group, and each of the remaining two has no substituent, $R^2$: a hydrogen atom, a biphenylmethyl group having a tetrazolyl group which may be substituted by aralkyl, a cycloalkyl group, or a lower alkyl group which may be substituted by hydroxyl group, lower alkoxy, carboxyl or lower alkoxycarbonyl, and $R^5$ and $R^6$: these may be the same or different from each other, and each represents a hydrogen atom, a halogen atom, a biphenylmethyl group having a tetrazolyl group which may be substituted by aralkyl, a formyl group, a carboxyl group, an esterified carboxyl group, a cycloalkyl group, a lower alkoxy group, a lower alkoxycarbonyl group, or a lower alkyl group which may be substituted by hydroxyl, formyl, carboxyl, lower alkoxy or lower alkoxycarbonyl, provided that at least one of $R^1$ to $R^6$ is a biphenylmethyl group having a tetrazolyl group which may be substituted by aralkyl, and the broken lines mean that the pyrazolotriazole ring forms three double bonds, or a pharmaceutically acceptable salt thereof.

9. A pharmaceutically composition according to claim 8 wherein the active material is a therapeutic agent for treating hypertension or chronic heart failure.

10. A pharmaceutical composition containing according to claim 8 which comprises as an active ingredient 2,7-diethyl-5-[[2'-(tetrazol-5 -yl)biphenyl-4-yl]methyl]-5H-pyrazolo[1,5-b][1,2,4]triazole or a potassium salt thereof.

11. A pharmaceutical composition containing as the active active ingredient 2,7-diethyl-5-[[2'-(tetrazol-5 -yl)biphenyl-4-yl]methyl]-5H-pyrazolo[1,5-b][1,2,4]triazole-6-carboxylic acid or an ester thereof.

12. A pharmaceutical composition of claim 7 which comprises as an active component 2,7-diethyl-5-[[2'-(tetrazol-5 -yl)biphenyl-4-yl]methyl]-5H-pyrazolo[1,5-b][1,2,4]triazole or a potassium salt thereof.

13. A method for imparting an AII receptor-blocking activity to a patient in need of such treatment which comprises administering to said patient an AII receptor-blocking effective amount of the pharmaceutical composition of claim 7.

* * * * *